United States Patent
Carleton et al.

(10) Patent No.: US 11,572,405 B2
(45) Date of Patent: Feb. 7, 2023

(54) COMBINATION THERAPY WITH ANTI-IL-8 ANTIBODIES AND ANTI-PD-1 ANTIBODIES FOR TREATING CANCER

(71) Applicant: BRISTOL-MYERS SQUIBB COMPANY, Princeton, NJ (US)

(72) Inventors: Michael Carleton, Churchville, PA (US); David Feltquate, Belle Mead, NJ (US); Olivier De Henau, Brussels (BE); Timothy Patrick Reilly, New Hope, PA (US); Tian Chen, Princeton, NJ (US); Ye Feng, Princeton, NJ (US); Shu-Pang Ben Huang, Newtown, PA (US); Ming Zhou, Pennington, NJ (US); Ramachandran Suresh, Monroe Township, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 67 days.

(21) Appl. No.: 16/768,838

(22) PCT Filed: Jan. 11, 2019

(86) PCT No.: PCT/US2019/013134
§ 371 (c)(1),
(2) Date: Jun. 1, 2020

(87) PCT Pub. No.: WO2019/140150
PCT Pub. Date: Jul. 18, 2019

(65) Prior Publication Data
US 2021/0054063 A1    Feb. 25, 2021

Related U.S. Application Data

(60) Provisional application No. 62/679,412, filed on Jun. 1, 2018, provisional application No. 62/650,047, filed on Mar. 29, 2018, provisional application No. 62/616,716, filed on Jan. 12, 2018.

(51) Int. Cl.
| | |
|---|---|
| *C07K 16/24* | (2006.01) |
| *A61P 35/04* | (2006.01) |
| *A61P 35/00* | (2006.01) |
| *A61K 39/395* | (2006.01) |
| *C07K 16/28* | (2006.01) |
| *G01N 33/68* | (2006.01) |
| *A61K 39/00* | (2006.01) |

(52) U.S. Cl.
CPC ........ *C07K 16/244* (2013.01); *A61K 39/3955* (2013.01); *A61P 35/00* (2018.01); *A61P 35/04* (2018.01); *C07K 16/2818* (2013.01); *G01N 33/6869* (2013.01); *A61K 2039/507* (2013.01); *A61K 2039/54* (2013.01); *A61K 2039/545* (2013.01); *C07K 2317/21* (2013.01); *C07K 2317/56* (2013.01); *C07K 2317/565* (2013.01); *G01N 2333/5421* (2013.01); *G01N 2800/52* (2013.01)

(58) Field of Classification Search
CPC ... C07K 16/244; C07K 16/2818; A61P 35/04; A61K 39/3955
See application file for complete search history.

(56) References Cited

U.S. PATENT DOCUMENTS

| | | |
|---|---|---|
| 5,175,384 A | 12/1992 | Krimpenfort et al. |
| 5,204,244 A | 4/1993 | Fell et al. |
| 5,306,627 A | 4/1994 | Yamada et al. |
| 5,401,643 A | 3/1995 | Yamada et al. |
| 5,434,340 A | 7/1995 | Krimpenfort et al. |
| 5,440,021 A | 8/1995 | Chuntharapai et al. |
| 5,543,503 A | 8/1996 | Chuntharapai et al. |
| 5,552,284 A | 9/1996 | Lee et al. |
| 5,571,702 A | 11/1996 | Lee et al. |
| 5,633,141 A | 5/1997 | Lee et al. |
| 5,652,338 A | 7/1997 | Matsushima et al. |
| 5,677,426 A | 10/1997 | Fong et al. |
| 5,686,070 A | 11/1997 | Doerschuk et al. |
| 5,698,196 A | 12/1997 | Matsushima et al. |
| 5,702,946 A | 12/1997 | Doerschuk et al. |
| 5,707,621 A | 1/1998 | Matsushima et al. |
| 5,707,622 A | 1/1998 | Fong et al. |
| 5,767,063 A | 6/1998 | Lee et al. |
| 5,769,269 A | 6/1998 | Peters |

(Continued)

FOREIGN PATENT DOCUMENTS

| | | |
|---|---|---|
| EP | 0315062 B1 | 5/1989 |
| EP | 0955060 A1 | 11/1999 |

(Continued)

OTHER PUBLICATIONS

Tartari et al., Economic sustainability of anti-PD-1 agents nivolumab and pembrolizumab in cancer patients: Recent insights and future challenges, Cancer Treatment Reviews, 48(2016), 20-24, Publication Date: Jun. 7, 2016 (Year: 2016).*

(Continued)

*Primary Examiner* — Peter J Reddig
*Assistant Examiner* — Cheng Lu
(74) *Attorney, Agent, or Firm* — Nelson Mullins Riley & Scarborough LLP; Jane E. Remillard, Esq.; Jeanne M. DiGiorgio, Esq.

(57) ABSTRACT

Provided herein are methods for the clinical treatment of tumors (e.g., advanced solid tumors) in patients having certain levels of serum IL-8 using an anti-IL-8 antibody in combination with an anti-PD-1 antibody.

28 Claims, 23 Drawing Sheets

Specification includes a Sequence Listing.

(56) References Cited

U.S. PATENT DOCUMENTS

| | | | |
|---|---|---|---|
| 5,776,457 | A | 7/1998 | Lee et al. |
| 5,783,415 | A | 7/1998 | Lee et al. |
| 5,831,032 | A | 11/1998 | Schraufstatter et al. |
| 5,840,856 | A | 11/1998 | Chuntharapai et al. |
| 5,856,457 | A | 1/1999 | Lee et al. |
| 5,874,080 | A | 2/1999 | Hebert et al. |
| 5,874,543 | A | 2/1999 | Chuntharapai et al. |
| 5,892,017 | A | 4/1999 | Lee et al. |
| 5,919,896 | A | 7/1999 | Lee et al. |
| 5,922,541 | A | 7/1999 | Lee et al. |
| 5,925,352 | A | 7/1999 | Matsushima et al. |
| 5,939,598 | A | 8/1999 | Kucherlapati et al. |
| 6,015,557 | A | 1/2000 | Tobinick et al. |
| 6,075,181 | A | 6/2000 | Kucherlapati et al. |
| 6,087,475 | A | 7/2000 | Lee et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,177,077 | B1 | 1/2001 | Tobinick |
| 6,300,129 | B1 | 10/2001 | Lonberg et al. |
| 6,376,659 | B1 | 4/2002 | Matsushima et al. |
| 6,379,660 | B1 | 4/2002 | Saavedra et al. |
| 6,419,934 | B1 | 7/2002 | Tobinick |
| 6,419,944 | B2 | 7/2002 | Tobinick |
| 6,423,321 | B2 | 7/2002 | Tobinick |
| 6,428,787 | B1 | 8/2002 | Tobinick |
| 6,436,390 | B1 | 8/2002 | Tekamp-Olson et al. |
| 6,680,209 | B1 | 1/2004 | Buechler et al. |
| 6,682,736 | B1 | 1/2004 | Hanson et al. |
| 6,984,720 | B1 | 1/2006 | Korman et al. |
| 7,282,568 | B2 | 10/2007 | Teeling et al. |
| 7,622,559 | B2 | 11/2009 | Teeling et al. |
| 8,105,588 | B2 | 1/2012 | Teeling et al. |
| 8,603,469 | B2 | 12/2013 | Teeling et al. |
| 10,066,012 | B2 | 9/2018 | Teeling et al. |
| 10,253,093 | B2 | 4/2019 | Teeling et al. |
| 2001/0006637 | A1 | 7/2001 | Akahoshi et al. |
| 2002/0006405 | A1 | 1/2002 | Kitajima et al. |
| 2004/0208873 | A1 | 10/2004 | Teeling et al. |
| 2008/0118517 | A1 | 5/2008 | Teeling et al. |
| 2010/0303823 | A1 | 12/2010 | Teeling et al. |
| 2012/0164143 | A1 | 6/2012 | Teeling et al. |
| 2014/0170156 | A1 | 6/2014 | Teeling et al. |
| 2016/0280780 | A1 | 9/2016 | Teeling et al. |
| 2016/0347849 | A1 | 12/2016 | Cai et al. |
| 2018/0251540 | A1 | 9/2018 | Teeling et al. |
| 2019/0248883 | A1 | 8/2019 | Teeling et al. |

FOREIGN PATENT DOCUMENTS

| | | | |
|---|---|---|---|
| EP | 0966971 A1 | 12/1999 | |
| EP | 0991423 B1 | 4/2000 | |
| WO | 89/08665 A1 | 9/1989 | |
| WO | 89/10962 A1 | 11/1989 | |
| WO | 90/02178 A1 | 3/1990 | |
| WO | 90/04036 A1 | 4/1990 | |
| WO | 90/12878 A1 | 11/1990 | |
| WO | 91/00906 A1 | 1/1991 | |
| WO | 91/10741 A1 | 7/1991 | |
| WO | 92/03918 A1 | 3/1992 | |
| WO | 92/04372 A1 | 3/1992 | |
| WO | 92/17497 A1 | 10/1992 | |
| WO | 94/02602 A1 | 2/1994 | |
| WO | 94/25585 A1 | 11/1994 | |
| WO | 94/28931 A1 | 12/1994 | |
| WO | 95/23865 A1 | 9/1995 | |
| WO | 96/02576 A1 | 2/1996 | |
| WO | 96/22785 A1 | 8/1996 | |
| WO | 96/33735 A1 | 10/1996 | |
| WO | 97/01354 A1 | 1/1997 | |
| WO | 97/13852 A1 | 4/1997 | |
| WO | 97/39772 A1 | 10/1997 | |
| WO | 97/39775 A1 | 10/1997 | |
| WO | 97/49426 A1 | 12/1997 | |
| WO | 98/17312 A1 | 4/1998 | |
| WO | 98/24884 A1 | 6/1998 | |
| WO | 98/58671 A1 | 12/1998 | |
| WO | 00/50079 A1 | 8/2000 | |
| WO | 00/57902 A1 | 10/2000 | |
| WO | 01/25492 A1 | 4/2001 | |
| WO | 01/32879 A2 | 5/2001 | |
| WO | 01/40306 A1 | 6/2001 | |
| WO | 01/49321 A1 | 7/2001 | |
| WO | 01/57056 A1 | 8/2001 | |
| WO | 02/24217 A1 | 3/2002 | |
| WO | 2004/058797 A2 | 7/2004 | |
| WO | WO-2004058797 A2 * | 7/2004 | ............... A61P 1/04 |
| WO | 2016/196228 A1 | 12/2016 | |
| WO | 2017/152085 A1 | 9/2017 | |
| WO | 2017/210453 A1 | 12/2017 | |
| WO | 2017/210473 A1 | 12/2017 | |
| WO | 2017/210637 A1 | 12/2017 | |
| WO | WO-2017210637 A1 * | 12/2017 | ............. A61P 35/00 |
| WO | 2019140150 A1 | 7/2019 | |

OTHER PUBLICATIONS

Bai et al., Regulation of PD-1/PD-L1 pathway and resistance to PD-1/PDL1 blockade, Oncotarget, 8(66): 110693-110707, Publication Date: Nov. 25, 2017 (Year: 2017).*

CXCL8 Genecards, retrieved from https://www.genecards.org/cgi-bin/carddisp.pl?gene=CXCL8 on Apr. 6, 2022 (Year: 2022).*

Wang et al., Association between serum cytokines and progression of breast cancer in Chinese population, Medicine (2017) 96:49(e8840), Publication Date: Dec. 2017 (Year: 2017).*

Raedler et al., Opdivo (Nivolumab): Second PD-1 inhibitor Receives FDA Approval for Unresectable or Metastatic Melanoma, American Health & Drug Benefits, Publication Date: Mar. 2015 (Year: 2015).*

Alt, Frederick W. et al., "Immunoglobulin genes in transgenic mice," TIG, vol. 1:231-236 (1985).

Attwood, Teresa K., "The Babel of Bioinformatics," Science, vol. 290:471-473 (2000).

Berman, Jeffrey E. et al., "Content and organization of the human Ig VH locus: definition of three new VH families and linkage to the Ig CH locus," The EMBO Journal, vol. 7(3):727-738 (1988).

Berton, Michael T. et al., "Synthesis of germ-line g1 immunoglobulin heavy-chain transcripts in resting B cells: Induction by interleukin 4 and inhibition by interferon g," Proc. Natl. Acad. Sci. USA, vol. 86:2829-2833 (1989).

Bollag, Roni J. et al., "Homologous Recombination in Mammalian Cells," Annu. Rev. Genet., vol. 23:199-225 (1989).

Brüuggemann, Marianne et al., "A repertoire of monoclonal antibodies with human heavy chains from transgenic mice," Proc. Natl. Acad. Sci. USA, vol. 86:6709-6713 (1989).

Brüggemann, Marianne et al., "Human antibody production in transgenic mice: expression from 100 kb of the human IgH locus," Eur. J. Immunol., vol. 21:1323-1326 (1991).

Bucchini, D. et al., "Rearrangement of a chicken immunoglobulin gene occurs in the lymphoid lineage of transgenic mice," Nature, vol. 326:409-411 (1987).

Buttin, G., "Exogenous Ig gene rearrangement in transgenic mice: a new strategy for human monoclonal antibody production?" TIG, vol. 3(8):205-206 (1987).

Capecchi, Mario R., "Altering the Genome by Homologous Recombination," Science, vol. 244:1288-1292 (1989).

Capecchi, Mario R., "The New Mouse Genetics: Altering the Genome by Gene Targeting," TIG, vol. 5(3):70-76 (1989).

Chen, Pojen P. et al., "Characterization of Two Immunoglobulin VH Genes that are Homologous to Human Rheumatoid Factors," Arthritis and Rheumatism, vol. 32(1):72-76 (1989).

Coffman, Robert L. et al., "A Mouse T Cell Product that Preferentially Enhances IgA Production, I. Biologic Characterization," The Journal of Immunology, vol. 139(11):3685-3690 (1987).

Coffman, Robert L. et al., "A T Cell Activity that Enhances Polyclonal IgE Production and its Inhibition by Interferon-g," The Journal of Immunology, vol. 136(3):949-954 (1986).

Doetschman, Thomas et al., "Targetted correction of a mutant HPRT gene in mouse embryonic stem cells," Nature, vol. 330:576-578 (1987).

(56) References Cited

OTHER PUBLICATIONS

Durdik, Jeannine et al., "Isotype switching by a microinjected m immunoglobulin heavy chain gene in transgenic mice," Proc. Natl. Acad. Sci. USA, vol. 86:2346-2350 (1989).
Esser, Charlotte et al., "Rapid induction of transcription of unrearranged sg1 switch regions in activated murine B cells by interleukin 4," The EMBO Journal, vol. 8(2):483-488 (1989).
Ferrier, Pierre et al., "Separate elements control DJ and VDJ rearrangement in a transgenic recombination substrate," The EMBO Journal, vol. 9(1):117-125 (1990).
Fishwild, Dianne M. et al., "High-avidity human IgGk monoclonal antibodies from a novel strain of minilocus transgenic mice," Nature Biotechnology, vol. 14(7):845-851 (1996).
Forni, Luciana et al., "Extensive splenic B cell activation in IgM-transgenic mice," Eur. J. Immunol., vol. 20:983-989 (1990).
Gerstein, Rachel M. et al., "Isotype Switching of an Immunoglobulin Heavy Chain Transgene Occurs by DNA Recombination between Different Chromosomes," Cell, vol. 63:537-548 (1990).
Goodhardt, M. et al., "Rearrangement and expression of rabbit immunoglobulin k light chain gene in transgenic mice," Proc. Natl. Acad. Sci. USA, vol. 84:4229-4233 (1987).
Gordon, Jon W., "Transgenic Mice in Immunology," The Mount Sinai Journal of Medicine, vol. 53(3):223-231 (1986).
Geeen, L.L. et al., "Antigen-specific human monoclonal antibodies from mice engineered with human Ig heavy and light chain YACs," Nature Genetics, vol. 7:13-21 (1994).
Hagman, James et al., "Inhibition of Immunoglobulin Gene Rearragement by the Expression of a I2 Transgene," J. Exp. Med., vol. 169:1911-1929 (1989).
Hofker, Marten H. et al., "Complete physical map of the human immunoglobulin heavy chain constant region gene complex," Proc. Natl. Acad. Sci. USA, vol. 86:5567-5571 (1989).
Huang, Suyun e a., "Fully Humanized Neutralizing Antibodies to Interieukin-8 (ABX-IL8) Inhibit Angiogenesis, Tumor Growth, and Metastasis of Human Melanoma," American Journal of Pathology, vol. 161(1):125-134 (2002).
Humphries, C.G. et al., "A new human immunoglobulin VH family preferentially rearranged in immature B-cell tumours," Nature, vol. 331:446-449 (1988).
Ichihara, Y. et al., "Organization of human immunoglobulin heavy chain diversity gene loci," The EMBO Journal, vol. 7(13):4141-4150 (1988).
Iglesias, Antonio et al., "Expression of immunoglobulin delta chain causes allelic exclusion in transgenic mice," Nature, vol. 330:482-484 (1987).
International Preliminary Report on Patentability, PCT/US2019/013134, dated Jul. 14, 2020, 9 pages.
International Search Report and Written Opinion, PCT/US2019/013134, dated Apr. 17, 2019, 13 pages.
Jaenisch, Rudolf, "Transgenic Animals," Science, vol. 240:1468-1474 (1988).
Jakobovits, Aya et al., "Analysis of homozygous mutant chimeric mice: Deletion of the immunoglobulin heavy-chain joining region blocks B-cell development and antibody production," Proc. Natl. Acad. Sci. USA, vol. 90:2551-2555 (1993).
James, Keith et al., "Human monoclonal antibody production, Current status and future prospects," Journal of Immunological Methods, vol. 100:5-40 (1987).
Janeway, Charles A. Jr., Immunobiology, Third Edition, pp. 3:7-3:11 (1997).
Jasin, Maria et al., "Homologous integration in mammalian cells without target gene selection," Genes & Development, vol. 2:1353-1363 (1988).
Ji, Yong-yong et al., "Flow Cytometry Analysis of the Neutralization Effect of Anti-iL-8 MCABS on IL-8-Activated Human Granulocytes," Shi yan sheng wu xue bao, vol. 28(3):257-261 (1995).
Jonker, M. et al., "In vivo treatment with a monoclonal chimeric anti-CD4 antibody results in prolonged depletion of circulating CD4+ cells in chimpanzees," Clin. Exp. Immunol., vol. 93:301-307 (1993).
Jung, Steffen et al., "Shutdown of Class Switch Recombination by Deletion of a Switch Region Control Element," Science, vol. 259:984-987 (1993).
Kenny, James J. et al., "Alteration of the B Cell Surface Phenotype, Immune Response to Phosphocholine and the B Cell Repertoire in M167 m Plus k Transgenic Mice," The Journal of Immunology, vol. 142(12):4466-4474 (1989).
Kitamura, Daisuke et al., "A B cell-deficient mouse by targeted disruption of the membrane exon of the mmunoglobulin m chain gene," Nature, vol. 350:423-426 (1991).
Knox, Susan J. et al., "Observation on the Effect of Chimeric Anti-CD4 Monoclonal Antibody in Patients With Mycosis Fungoides," Blood, vol. 77(1):20-30 (1991).
Koller, Beverly H. et al., "Inactivating the b2-microglobulin locus in mouse embryonic stem cells by homologous recombination," Proc. Natl. Acad. Sci. USA, vol. 86:8932-8935 (1989).
Kurdowska, A. et al., "An Anti-Interleukin 8 Monoclonal Antibody That Interferes with the Binding of Interleukin 8 to Cellular Receptors and the Activation of Human Blood Neutrophils," Hybridoma, vol. 14(3):225-233 (1995).
Lin, F.-L. et al., "Recombination in mouse L cells between DNA introduced into cells and homologous chromosomal sequences," Proc. Natl. Acad. Sci. USA, vol. 82:1391-1395 (1985).
Linton, Phyllis-Jean et al., "Primary Antibody-Forming Cells and Secondary B Cells Are Generated from Separate Precursor Cell Subpopulations," Cell, vol. 59:1049-1059 (1989).
Lo, David et al., "Expression of mouse IgA by transgenic mice, pigs and sheep," Eur. J. Immunol., vol. 21:1001-1006 (1991).
Lonberg, Nils et al., "Antigen-specific human antibodies from mice comprising four distinct genetic modifications," Nature, vol. 368:856-859 (1994).
Lorenz, Wulfing et al., "Physical map of the human immunoglobulin K locus and its implications for the mechanism of VK-JK rearrangement," Nucleic Acids Research, vol. 15(23):9667-9676 (1987).
Supplementary European Search Report for Application No. EP03799925,2 pages, dated Sep. 25, 2008.
Szurek, Paul et al., "Complete Nucleotide Sequence of the Murine g3 Switch Region and Analysis of Switch Recombination Sites in Two g3-Expressing Hybridomas," The Journal of Immunology, vol. 135(1):620-626 (1985).
Tahara, Tohru et al., "HLA antibody responses in HLA class I transgenic mice," Immunogenetics, vol. 32:351-360 (1990).
Taki, Shinsuke et al., "Targeted Insertion of a Variable Region Gene into the Immunoglobulin Heavy Chain Locus," Science, vol. 262:1268-1271 (1993).
Tanaka, Toshio et al., "An Antisense Oligonucleotide Complementary to a Sequence in Ig2b Increases g2b Germline Transcripts, Stimulates B Cell DNA Synthesis, and Inhibits Immunoglobulin Secretion," The Journal of Experimental Medicine, vol. 175:597-607 (1992).
Taussig, Michael J. et al., "Regulation of immunoglobulin gene rearrangement and expression," Immunology Today, vol. 10(5):143-146 (1989).
Taylor, Lisa D. et al., "Human immunoglobulin transgenes undergo rearrangement, somatic mutation and class switching in mice that lack endogenous IgM," International Immunology, vol. 6(4):579-591 (1994).
Thomas, Kirk R. et al., "High Frequency Targeting of Genes to Specific Sites in the Mammalian Genome," Cell, vol. 44:419-428 (1986).
Thomas, Kirk R. et al., "Site-Directed Mutagenesis by Gene Targeting in Mouse Embryo-Derived Stem Cells," Cell, vol. 51:503-512 (1987).
Tomlinson, Ian M. et al., "The Repertoire of Human Germline VH Sequences Reveals about Fifty Groups of VH Segments with Different Hypervariable Loops," J. Mol. Biol., vol. 22:776-798 (1992).
Uhlmann, Eugen et al., "Antisense Oligonucleotides: A New Therapeutic Principle," Chemical Reviews, vol. 90(4):544-584 (1990).
Vlasov, V.V. et al., "Arrest of immunoglobulin G mRNA translation in vitro with an alkylating antisense oligonucleotide derivative," Chemical Abstracts, vol. 112:28 (1990).

(56) References Cited

OTHER PUBLICATIONS

Weaver, David et al., "A Transgenic Immunoglobulin Mu Gene Prevents -Rearrangement of Endogenous Genes," Dell, vol. 42:117-127 (1985).
Weiss, Rick, "Mice Making Human-Like Antibodies: Medical Implications Called Stupendous," The Washington Post, Apr. 28, 1994.
Wofsy, David et al., "Reversal of Advanced Murine Lupus in NZB/NZW F1 Mice by Treatment with Monoclonal Antibody to L3T4," The Journal of Immunology, vol. 138(10):3247-3253 (1987).
Yamamura, Ken-Ichi et al., "Cell-type-specific and regulated expression of a human g1 heavy-chain immunoglobulin gene in transgenic mice," Proc. Natl. Acad. Sci. USA, vol. 83:2152-2156 (1986).
Yancopoulos, George D. et al., "Developmentally Controlled and Tissue-Specific Expression of Unrearranged VH Gene Segments," Cell, vol. 40:271-281 (1985).
Yancopoulos, George D. et al., "Regulation of the Assembly and Expression of Variable-Region Genes," Annual Reviews, vol. 4:339-368 (1986).
Yang, Xiao-Dong et al., "Fully human anti-interleukin-8 monoclonal antibodies: potential therapeutics for the treatment of inflammatory disease states," Journal of Leukocyte Biology, vol. 66:401-410 (1999).
Yasui, Hisashi et al., "Class switch from m to d is mediated by homologous recombination between sm and Sm sequences in human immunoglobulin gene loci," Eur. J. Immunol., vol. 19:1399-1403 (1989).
Zijlstra, Maarten et al., "Germ-line transmission of a disrupted b2-microglobulin gene produced by homologous recombination in embryonic stem cells," Nature, vol. 342:435-438 (1989).
Zimmer, Andreas et al., "Production of chimaeric mice containing embryonic stem (ES) cells carrying a homoeobox Hox 11 allele mutated by homologous recombination," Nature, vol. 338:150-153 (1989).
Lutzker, Stuart et al., "Structure and Expression of Germ Line Immunoglobulin g2b Transcripts," Molecular and Cellular Biology, vol. 8(4):1849-1852 (1988).
Mansour, Suzanne L. et al., "Disruption of the proto-oncogene int-2 in mouse embryo-derived stem cells: a general strategy for targeting mutations to non-selectable genes," Nature, vol. 336:348-352 (1988).
Metzler, W.J. et al., "Solution structure of human CTLA-4 and delination of the CD80/CD86 binding site conserved in CD28," Nature Structural Biology, vol. 4(7):527-531 (1997).
Miller, Jim et al., "Structural alterations in J regions of mouse immunoglobulin I genes are associated with differential gene expression," Nature, vol. 295:428-430 (1982).
Mills, Frederick C. et al., "DNase I hypersensitive sites in the chromatin of human m immunoglobulin heavy-chain genes," Nature, vol. 306:809-812 (1983).
Mills, Frederick C. et al., "Sequences of human immunoglobulin switch regions: implications for recombination and transcription," Nucleic Acid Research, vol. 18(24):7305-7316 (1990).
Morrison, Sherie L., "Success in specification," Nature, vol. 368:812-813 (1994).
Mowatt, Michael R. et al., "DNA Sequence of the Murine g1 Switch Segment Reveals Novel Structural Elements," The Journal of Immunology, vol. 136(7):2674-2683 (1986).
Murray, Andrew W. et al., "Construction of artificial chromosomes in yeast," Nature, vol. 305:189-193 (1983).
Müller, Werner et al., "Membrane-bound IgM obstructs B cell development in transgenic mice," Eur. J. Immunol., vol. 19:923-928 (1989).
Neuberger, M.S. et al., "Isotype exclusion and transgene down-regulation in immunoglobulin-I transgenic mice," Nature, vol. 338:350-352 (1989).
Neuberger, Michael, "Generating high-avidity human Mabs in mice," Nature Biotechnology, vol. 14:826 (1996).
Mewman, Roland et al., "'Primatization' of Recombinant Antibodies for Immunotherapy of Human Diseases: a Macaque/Human Chimeric Antibody Against Human CD4," Biotechnology, vol. 10:1455-1460 (1992).

Nikaido, Toshio et al., "Nucleotide Sequences of Switch Regions of Immunoglobulin Ce and Cg Genes and Their Comparison," The Journal of Biological Chemistry, vol. 257(13):7322-7329 (1982).
Nikaido, Toshio et al., "Switch region of immunoglobulin Cm gene is composed of simple tandem repetitive sequences," Nature, vol. 292:845-848 (1981).
Nussenzweig, Michel C. et al., "A human immunoglobulin gene reduces the incidence of lymphomas in c-Myc-bearing transgenic mice," Nature, vol. 336:446-450 (1988).
Nussenzweig, Michel C. et al., "Allelic Exclusion in Transgenic Mice Carrying Mutant Human IgM Genes," J. Exp. Med., vol. 167:1969-1974 (1988).
Oettinger, Marjorie A. et al., "RAG-1 and RAG-2, Adjacent Genes That Synergistically Activate V(D)J Recombination," Science, vol. 248:1517-1523 (1990).
Paul, William P., Fundamental Immunology, Third Edition, p. 292-295 (1993).
Petters, R.M., "Transgenic Mice in Immunological Research," Veterinary Immunology and Immunopathology, vol. 17:267-278 (1987).
Pettersson, Sven et al., "A second B cell-specific enhancer 3' of the immunoglobulin heavy-chain locus," Nature, vol. 344:165-168 (1990).
Portolano, Stefano et al., "Lack of Promiscuity in Autoantigen-Specific H and L Chain Combinations as Revealed by Human H and L Chain 'Roulette'," The Journal of Immunology, vol. 150(3):880-887 (1993).
Powelson, John A. et al., "CDR-Grafted OKT4A Monoclonal Antibody in Cynomolgus Renal Allograft Recipients," Transplantation, vol. 57(6):788-793 (1994).
Rabbitts, T.H. et al., "Human immunoglobulin heavy chain genes: evolutionary comparisons of Cm, Cd and Cg genes and associated switch sequences," Nucleic Acids Research, vol. 9(18):4509-4524 (1981).
Rath, Satyajit et al., "B Cell Abnormalities Induced by A m Ig Transgene Extend to L Chain Isotype Usage," The Journal of Immunology, vol. 146(8):2841-2847 (1991).
Rath, Satyajit et al., "Quantitative Analysis of Idotypic Mimicry and Alelic Exclusion in Mice with A m Ig Transgene," The Journal of Immunology, vol. 143(6):2074-2080 (1989).
Ravetch, J.V. et al., "Evolutionary approach to the question of immunoglobulin heavy chain switching: Evidence from cloned human and mouse genes," Proc. Natl. Acad. Sci. USA, vol. 77(11):6734-6738 (1980).
Reid, Laurence E. et al., "A single DNA response element can confer inducibility by both a- and g-interferons," Proc. Natl. Acad. Sci. USA, vol. 86:840-844 (1989).
Ritchie, Kindred A. et al., "Allelic exclusion and control of endogenous immunoglobulin gene rearrangement in k transgenic mice," Nature, vol. 312:517-520 (1984).
Rothman, Paul et al., "Structure and expression of germline immunoglobulin g3 heavy chain gene transcripts: implications for mitogen and lymphokine directed class-switching," International Immunology, vol. 2(7):621-627 (1990).
Rudikoff, Stuart et al., "Single amino acid substitution altering antigen-binding specificity," Proc. Natl. Acad. Sci USA, vol. 79:1979-1983 (1982).
Rusconi, Sandro et al., "Transmission and expression of a specific pair of rearranged immunoglobulin m and k genes in a transgenic mouse line," Nature, vol. 314:330-334 (1985).
Salcedo, Rosalba et al., "Combined Administration of Antibodies to Human Interleukin 8 and Epidermal Growth Factor Receptor Results in Increased Antimetastatic Effects on Human Breast Carcinoma-Xenografts," Clinical Cancer Reseasrch, vol. 8:2655-2665 (2002).
Sato, Takayuki et al., "Physical linkage of a variable region segment adn the joining region segment of the human immunoglobulin heavy chain locus," Biochemical and Biophysical Research Communications, vol. 154(1):265-271 (1988).
Scangos, George et al., "Gene Transfer into Mice," Advances in Genetics, vol. 24:285-322 (1987).
Sedivy, John M. et al., "Positive genetic selection for gene disruption in mammalian cells by homologous recombination," Proc. Natl. Acad. Sci. USA, vol. 86:227-231 (1989).

(56) References Cited

OTHER PUBLICATIONS

Sekido, Nobuaki et al., "Prevention of lung reperfusion injury in rabbits by a monoclonal antibody against interleukin-8," Nature, vol. 365:654-657 (1993).

Shimizu, Akira et al., "Immunoglobulin double-isotype expression by trans-mRNA in a human immunoglobulin transgenic mouse," Proc. Natl. Acad. Sci. USA, vol. 86:8020-8023 (1989).

Shimizu, Akira et al., "Trans-Splicing as a Possible Molecular Mechanism for the Multiple Isotype Expression of the Immunoglobulin Gene," J. Exp. Med., vol. 173:1385-1393 (1991).

Sideras, Paschalis et al., "Production of sterile transcripts of Cg genes in an IgM-producing human neoplastic B cell line that switches to IgG-producing cells," International Immunology, vol. 1(6):631-642 (1989).

Siebenlist, U. et al., "Human immunoglobulin D segments encoded in tandem multigenic families," Nature, vol. 294:631-635 (1981).

Skolnick, Jeffrey et al., "From genes to protein structure and function: novel applications of computational approaches in the genomic era," Trends Biotechnol., vol. 18(1):34-39 (2000).

Smithies, Oliver et al., "Insertion of DNA sequences into the human chromosomal b-globin locus by homologous recombination," Nature, vol. 317:230-234 (1985).

Snapper, Clifford M. et al., "Interferon-g and B Cell Stimulatory Factor-1 Reciprocally Regulate Ig Isotype Production," Science, vol. 236:944-947 (1987).

Song, Kyu-Young et al., "Accurate modification of a chromosomal plasmid by homologous recombination in human cells," Proc. Natl. Acad. Sci. USA, vol. 84:6820-6824 (1987).

Soriano, Philippe et al., "Targeted Disruption of the c-src Proto-Oncogene Leads to Osteopetrosis in Mice," Cell, vol. 64:693-702 (1991).

Stavnezer, Janet et al., "Immunoglobulin heavy-chain switching may be directed by prior induction of transcripts from constant-region genes," Proc. Natl. Acad. Sci. USA, vol. 85:7704-7708 (1988).

Stites, Daniel P. et al., "Immunoglobulins II: Gene Organization & Assembly," Basic & Clinical Immunology, Chpt. 5, p. 50 (1984).

Storb, Ursula et al., "Expression, Allelic Exclusion and Somatic Mutation of Mouse Immunoglobulin Kappa Genes," Immunological Reviews, vol. 89:85-102 (1986).

Storb, Ursula, "Immunoglobulin Gene Analysis in Transgenic Mice," Immunoglobulin Genes, Chpt. 16, pp. 303-326 (1989).

Benoy IH, et al., "Increased serum interleukin-8 in patients with early and metastatic breast cancer correlates with early dissemination and survival," Clin Cancer Res., vol. 10(21):7157-7162 (2004).

\* cited by examiner

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Synthetic: HuMax-IL-8 VHCDR1
```

```
<400> SEQUENCE: 1

His Tyr Gly Met Tyr
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic: HuMax-IL-8 VHCDR2

<400> SEQUENCE: 2

Val Ile Trp Tyr Asp Gly Ser Tyr Glu Tyr Asn Ala Asp Ser Val Lys
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Synthetic: HuMax-IL-8 VHCDR3

<400> SEQUENCE: 3

Asp Arg Val Gly Leu Phe Asp Tyr
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic: HuMax-IL-8 VLCDR1

<400> SEQUENCE: 4

Arg Ala Ser Gln Ser Ile Ser Ser Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic: HuMax-IL-8 VLCDR2

<400> SEQUENCE: 5

Gly Pro Ser Ser Arg Ala Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic: HuMax-IL-8 VLCDR3

<400> SEQUENCE: 6

Gln Gln Tyr Ala Gly Ser Leu Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Synthetic: HuMax-IL-8 VH
```

<400> SEQUENCE: 7

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser His Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Tyr Glu Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Gly Leu Phe Asp Tyr Trp Gly Gln Gly Thr Leu
            100                 105                 110

Val Thr Val Ser Ser
            115

<210> SEQ ID NO 8
<211> LENGTH: 107
<212> TYPE: PRT
<213> ORGANISM: Artificial Sequence
<220> FEATURE:
<223> OTHER INFORMATION: Synthetic: HuMax-IL-8 VL

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Leu
                85                  90                  95

Thr Phe Gly Pro Gly Thr Lys Val Asp Ile Lys
            100                 105

<210> SEQ ID NO 9
<211> LENGTH: 447
<212> TYPE: PRT
<213> ORGANISM: Artificial Sequence
<220> FEATURE:
<223> OTHER INFORMATION: Synthetic: HuMax-IL-8 HC

<400> SEQUENCE: 9

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser His Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Tyr Glu Tyr Asn Ala Asp Ser Val
    50                  55                  60

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 10
<211> LENGTH: 214
<212> TYPE: PRT
<213> ORGANISM: Artificial Sequence
<220> FEATURE:
<223> OTHER INFORMATION: Synthetic: HuMax-IL-8 LC -continued

```
<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Leu
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 5
<212> TYPE: PRT
<213> ORGANISM: Artificial Sequence
<220> FEATURE:
<223> OTHER INFORMATION: Synthetic: Nivolumab VHCDR1

<400> SEQUENCE: 11

Asn Ser Gly Met His
1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic: Nivolumab VHCDR2

<400> SEQUENCE: 12

Val Ile Trp Tyr Asp Gly Ser Lys Arg Tyr Tyr Ala Asp Ser Val Lys
1               5                   10                  15

Gly

<210> SEQ ID NO 13
<211> LENGTH: 4
<212> TYPE: PRT
<213> ORGANISM: Artificial Sequence
<220> FEATURE:
```

<223> OTHER INFORMATION: Synthetic: Nivolumab VHCDR3

<400> SEQUENCE: 13

Asn Asp Asp Tyr
1

<210> SEQ ID NO 14
<211> LENGTH: 11
<212> TYPE: PRT
<213> ORGANISM: Artificial Sequence
<220> FEATURE:
<223> OTHER INFORMATION: Synthetic: Nivolumab VLCDR1

<400> SEQUENCE: 14

Arg Ala Ser Gln Ser Val Ser Ser Tyr Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic: Nivolumab VLCDR2

<400> SEQUENCE: 15

Asp Ala Ser Asn Arg Ala Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic: Nivolumab VLCDR3

<400> SEQUENCE: 16

Gln Gln Ser Ser Asn Trp Pro Arg Thr
1               5

<210> SEQ ID NO 17
<211> LENGTH: 113
<212> TYPE: PRT
<213> ORGANISM: Artificial Sequence
<220> FEATURE:
<223> OTHER INFORMATION: Synthetic: Nivolumab VH

<400> SEQUENCE: 17

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 18
<211> LENGTH: 107
<212> TYPE: PRT
<213> ORGANISM: Artificial Sequence
<220> FEATURE:
<223> OTHER INFORMATION: Synthetic: Nivolumab VL

<400> SEQUENCE: 18

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                 55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105
```

<210> SEQ ID NO 19
<211> LENGTH: 440
<212> TYPE: PRT
<213> ORGANISM: Artificial Sequence
<220> FEATURE:
<223> OTHER INFORMATION: Synthetic: Nivolumab HC

<400> SEQUENCE: 19

```
Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
 50                 55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205
```

```
Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 20
<211> LENGTH: 214
<212> TYPE: PRT
<213> ORGANISM: Artificial Sequence
<220> FEATURE:
<223> OTHER INFORMATION: Synthetic: Nivolumab LC

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys
    210
```

COMBINATION THERAPY WITH ANTI-IL-8 ANTIBODIES AND ANTI-PD-1 ANTIBODIES FOR TREATING CANCER

CROSS-REFERENCE TO RELATED APPLICATIONS

This application is a 35 U.S.C. 371 national stage filing of International Application No. PCT/US2019/013134, filed Jan. 11, 2019, which claims priority to U.S. Provisional Application 62/679,412, filed Jun. 1, 2018, U.S. Provisional Application 62/650,047, filed Mar. 29, 2018 and U.S. Provisional Application 62/616,716, filed Jan. 12, 2018. The contents of the aforementioned applications are hereby incorporated by reference in their entirety.

SEQUENCE LISTING

The instant application contains a Sequence Listing which has been submitted in ASCII format via EFS-Web, and is hereby incorporated by reference in its entirety. Said ASCII copy, created on Jun. 1, 2020, is named MXI-610US.txt and is 18,799 bytes in size.

BACKGROUND

Recent advances in the development of several immune checkpoint pathway inhibitors have provided new immunotherapeutic approaches to treat cancer. Antibodies of these new class of inhibitors include, e.g., ipilimumab (YERVOY®), which binds to and inhibits Cytotoxic T-Lymphocyte Antigen-4 (CTLA-4), and nivolumab and pembrolizumab (formerly lambrolizumab; USAN Council Statement, 2013), which bind specifically to the Programmed Death-1 (PD-1) receptor and block the inhibitory PD-1/PD-1 ligand pathway. Despite the remarkable success of these agents, however, a certain population of cancer patients are refractory to or relapse following treatment with these antibodies. Accordingly, novel therapies that target this patient population are desired.

SUMMARY

Provided herein are methods of treating a subject having cancer, e.g., advanced solid tumors, by administering an anti-IL-8 antibody in combination with an anti-PD-1 antibody.

In one aspect, provided herein is a method of treating a solid tumor in a human subject, the method comprising administering to the subject an effective amount of each of:
(a) an anti-IL-8 antibody comprising CDR1, CDR2, and CDR3 domains of the heavy chain variable region having the sequence set forth in SEQ ID NO: 7, and CDR1, CDR2, and CDR3 domains of the light chain variable region having the sequence set forth in SEQ ID NO: 8,
(b) an anti-PD-1 antibody comprising CDR1, CDR2, and CDR3 domains of the heavy chain variable region having the sequence set forth in SEQ ID NO: 17, and CDR1, CDR2, and CDR3 domains of the light chain variable region having the sequence set forth in SEQ ID NO: 18.

In some embodiments, the method comprises at least one administration cycle, wherein the cycle is a period of 4 weeks or 28 days, wherein for each of the at least one cycles, one dose of the anti-IL-8 antibody is administered at a fixed dose of 2400 mg, 1200 mg, or 600 mg, or a fixed dose of about 2400 mg, 1200 mg, or 600 mg, and one dose of the anti-PD-1 antibody is administered at a dose of 240 mg, 360 mg, or 480 mg, or a dose of about 240 mg, 360 mg, or 480 mg. In some embodiments, the anti-IL-8 antibody and anti-PD-1 antibody are administered at the following doses: (a) 2400 mg anti-IL-8 antibody and 240 mg, 360 mg, or 480 mg of anti-PD-1 antibody; (b) 1200 mg anti-IL-8 antibody and 240 mg, 360 mg, or 480 mg of anti-PD-1 antibody; or (c) 600 mg anti-IL-8 antibody and 240 mg, 360 mg, or 480 mg of anti-PD-1 antibody. In some embodiments, the treatment consists of up to 26 cycles. In some embodiments, the anti-IL-8 antibody, or anti-IL-8 antibody and anti-PD-1 antibody, are administered on Day 1 of each cycle.

In some embodiments, the baseline serum IL-8 level in the subject is above the lower limit of quantitation, for example, at least or greater than 10 pg/mL, 9 pg/mL, 8 pg/mL, 7 pg/mL, 6 pg/mL, 5 pg/mL, 4 pg/mL, 3 pg/mL, g2 pg/mL, or 1 pg/mL, as assessed by, e.g., ELISA (e.g., sandwich ELISA). In some embodiments, the baseline serum IL-8 level in the subject is >10 pg/mL. In some embodiments, the baseline serum IL-8 level in the subject is >5 pg/mL. In some embodiments, the cancer has progressed or relapsed after anti-PD-1 or anti-PD-L1 therapy.

In some embodiments, the anti-IL-8 antibody, or anti-IL8 antibody and anti-PD-1 antibody, are formulated (together or separately) for intravenous administration. In some embodiments, the anti-IL-8 antibody is administered prior to administration of the anti-PD-1 antibody, e.g., within about 30 minutes prior to administration of the anti-PD-1 antibody.

In some embodiments, the methods described herein produce at least one therapeutic effect chosen from a reduction in size of a tumor, reduction in number of metastatic lesions over time, complete response, partial response, and stable disease. In some embodiments, the methods described herein produce at least one therapeutic effect chosen from prolonged survival, such as progress free survival or overall survival, optionally compared to another therapy or placebo.

In some embodiments, the methods described herein are used to treat a solid tumor (e.g., a metastatic, recurrent, and/or unresectable tumor) is associated with a cancer selected from the group consisting of: melanoma, non-small cell lung carcinoma, renal cell carcinoma, triple negative breast cancer, colorectal cancer, pancreatic ductal adenocarcinoma, and hepatocellular carcinoma.

In some embodiments, the anti-IL-8 antibody comprises heavy chain and light chain variable region CDRs comprising the amino acid sequences set forth in SEQ ID NOs: 1-3 and 4-6, respectively; heavy and light chain variable region sequences set forth in SEQ ID NOs: 7 and 8, respectively; or heavy and light chain sequences set forth in SEQ ID NOs: 9 and 10, respectively. In some embodiments, the anti-PD-1 antibody comprises heavy chain and light chain variable region CDRs comprising the amino acid sequences set forth in SEQ ID NOs: 11-13 and 14-16, respectively; heavy and light chain variable region sequences set forth in SEQ ID NOs: 17 and 18, respectively; or heavy and light chain sequences set forth in SEQ ID NOs: 19 and 20, respectively.

In another aspect, provided herein is a method of treating a solid tumor in a human subject, the method comprising (i) determining the baseline serum IL-8 level in the human subject; (ii) if the human subject has a baseline serum IL-8 level of at least 5 pg/mL, administering to the subject an effective amount of each of an anti-IL-8 antibody comprising CDR1, CDR2, and CDR3 domains of the heavy chain variable region having the sequence set forth in SEQ ID NO: 7, and CDR1, CDR2, and CDR3 domains of the light chain variable region having the sequence set forth in SEQ ID NO: 8, (b) an anti-PD-1 antibody comprising CDR1, CDR2, and CDR3 domains of the heavy chain variable region having the sequence set forth in SEQ ID NO: 17, and CDR1, CDR2, and CDR3 domains of the light chain variable region having the sequence set forth in SEQ ID NO: 18. In some embodiments, the human subject has a baseline serum IL-8 level of at least 10 pg/mL. In some embodiments, the human subject has a baseline serum IL-8 level between 10 pg/mL and 50 pg/mL, between 10 pg/mL and 25 pg/mL, or less than or equal to 23 pg/mL. In another aspect, provided herein is a method of determining likelihood of response of a human subject having a solid tumor to a therapy containing an anti-PD-1 antibody, comprising determining the baseline serum IL-8 level of the human subject; herein the human subject is likely to respond to the therapy if the baseline serum IL-9 level is between 10 pg/mL and 50 pg/mL. In some embodiments, the human subject is likely to respond to the therapy if the baseline serum IL-9 level is between 10 pg/mL and 25 pg/mL. In some embodiments, the human subject is likely to respond to the therapy if the baseline serum IL-9 level is less than or equal to 23 pg/mL.

In another aspect, provided herein is a kit for treating a solid tumor in a human subject, the kit comprising a dose of an anti-IL-8 antibody comprising CDR1, CDR2, and CDR3 domains of the heavy chain variable region having the sequence set forth in SEQ ID NO: 7, and CDR1, CDR2, and CDR3 domains of the light chain variable region having the sequence set forth in SEQ ID NO: 8, and a dose of an anti-PD-1 antibody comprising CDR1, CDR2, and CDR3 domains of the heavy chain variable region having the sequence set forth in SEQ ID NO: 17, and CDR1, CDR2, and CDR3 domains of the light chain variable region having the sequence set forth in SEQ ID NO: 18, and instructions for use. In some embodiments, the anti-IL-8 antibody in the kit comprises heavy chain and light chain variable region CDRs comprising the amino acid sequences set forth in SEQ ID NOs: 1-3 and 4-6, respectively, and the anti-PD-1 antibody in the kit comprises heavy chain and light chain variable region CDRs comprising the amino acid sequences set forth in SEQ ID NOs: 11-13 and 14-16, respectively.

DETAILED DESCRIPTION

Figure 1A:
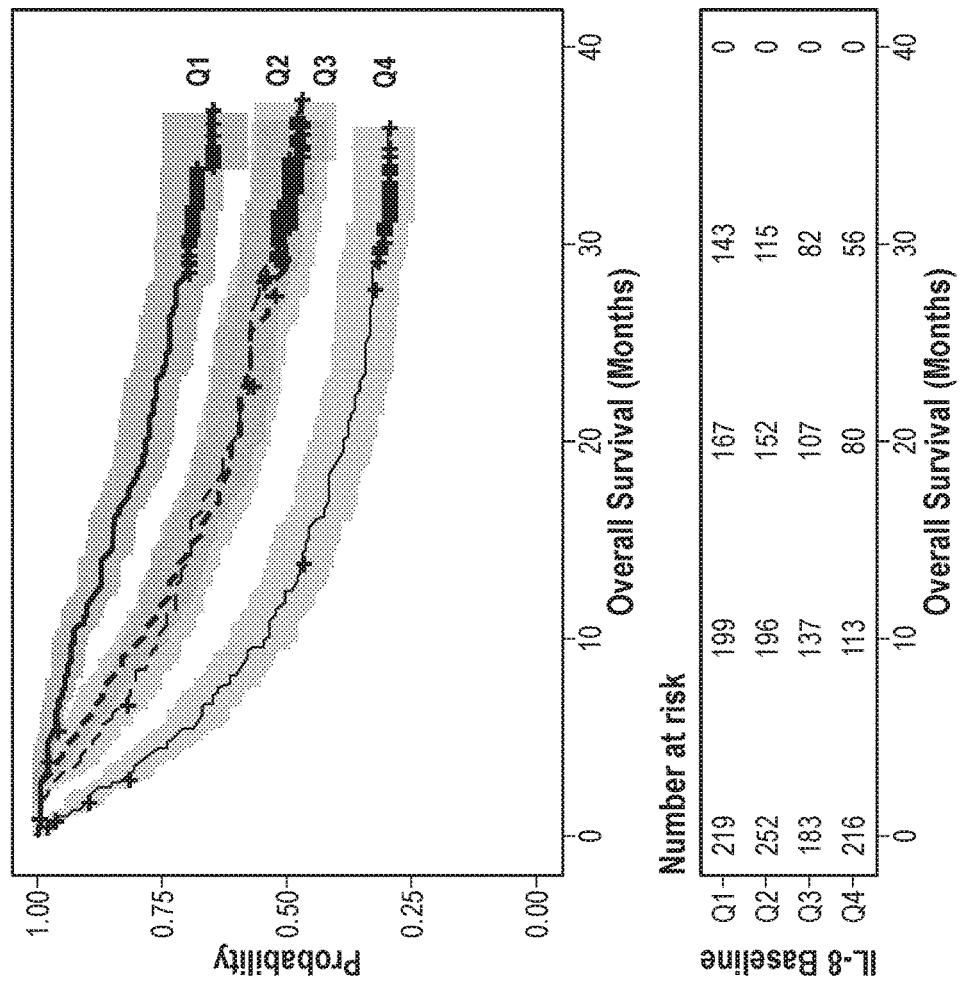
FIGS. 1A-1D are KM-Plots of overall survival (OS) by IL-8 baseline quartiles (Q1 being the lowest quartile by serum IL-8 baseline level) in study CA209-067, for all treated subjects (FIG. 1A), subjects treated with nivolumab (FIG. 1B), subjects treated with ipilimumab (FIG. 1C), and subjects treated with a combination of nivolumab and ipilimumab (FIG. 1D). The analysis shows that baseline IL-8 is prognostic for OS.
Figure 1B:
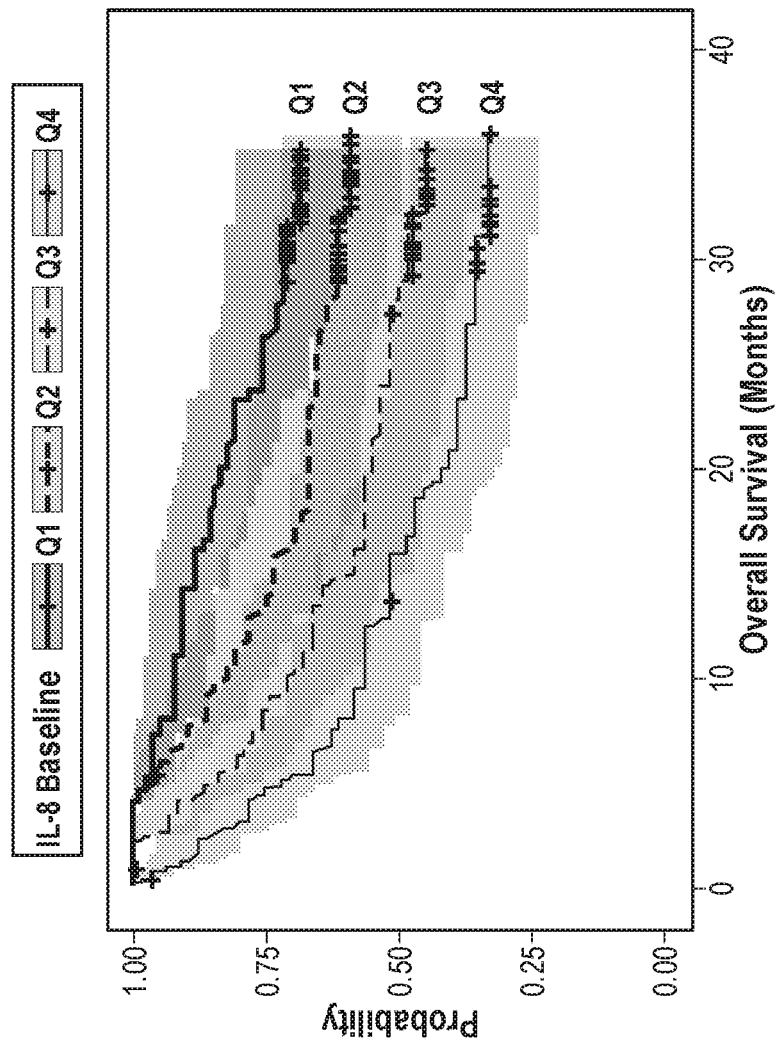
Figure 1C:
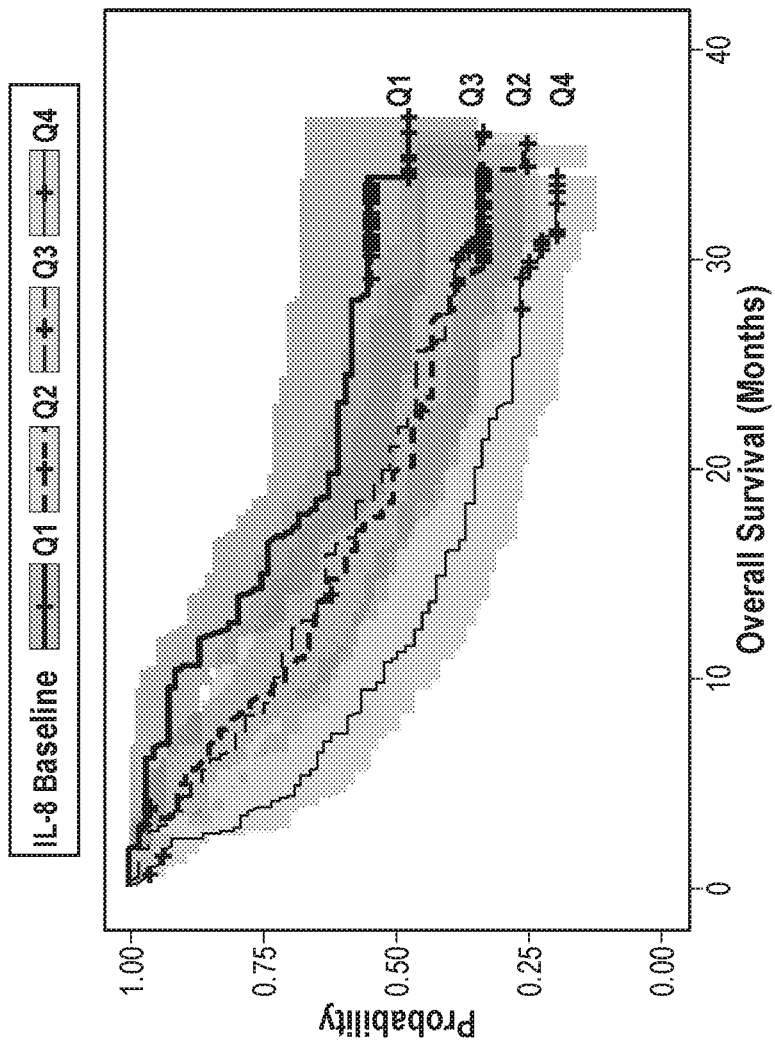
Figure 1D:
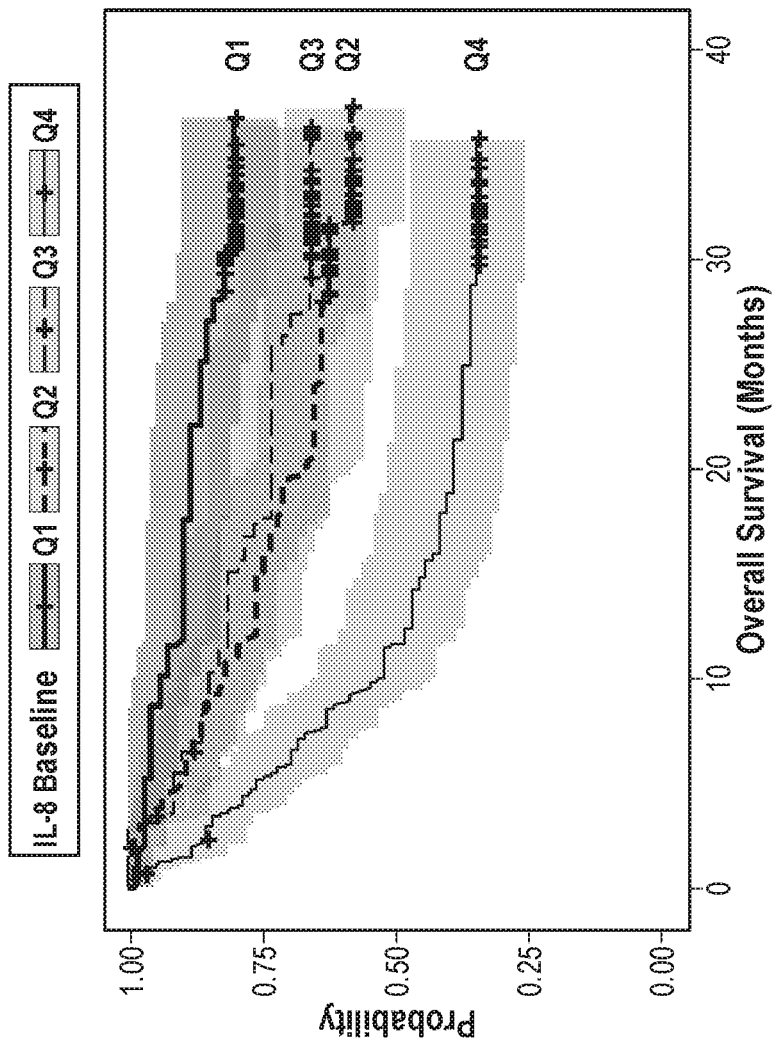
Figure 2A:
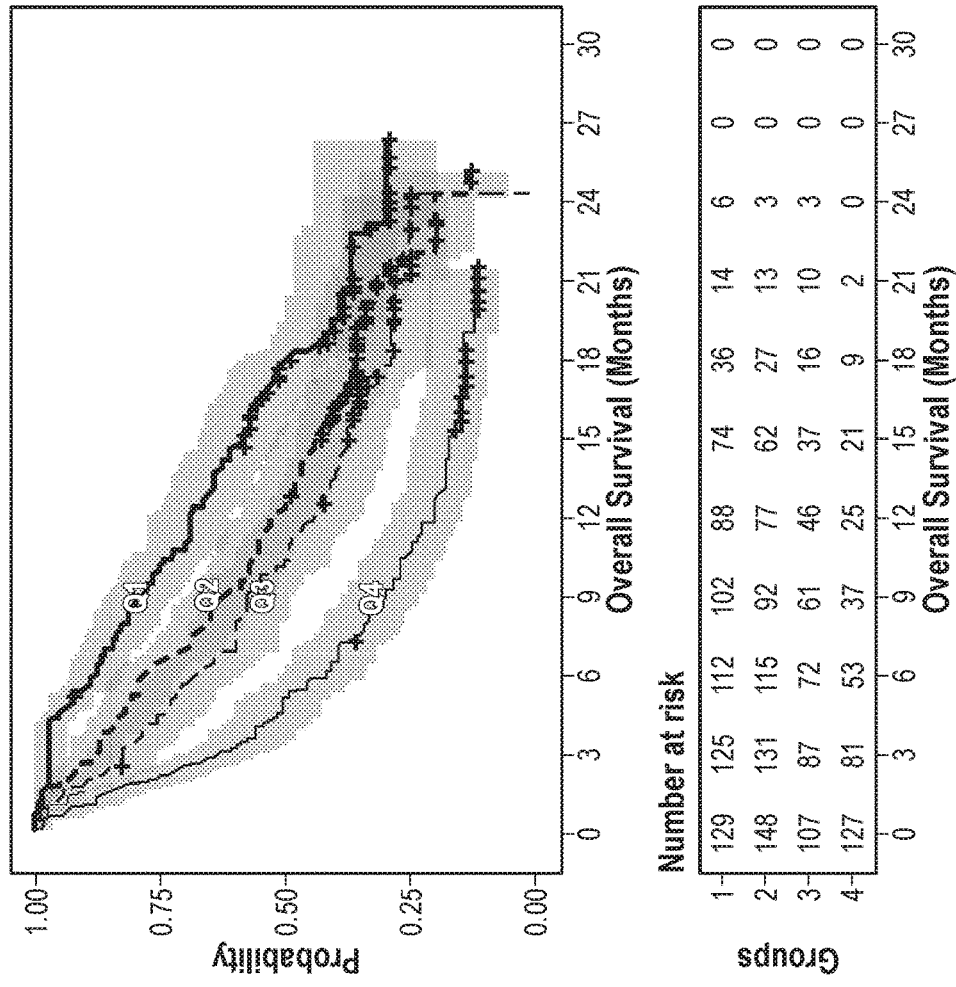
FIGS. 2A-2C are KM-Plots of overall survival (OS) by IL-8 baseline quartiles (Q1 being the lowest quartile by serum IL-8 baseline level) in study CA209-057, for all treated subjects (2A), subjects treated with nivolumab (2B), or subjects treated with Docetaxel (2C). The analysis shows that baseline IL-8 is prognostic for OS.
Figure 2B:
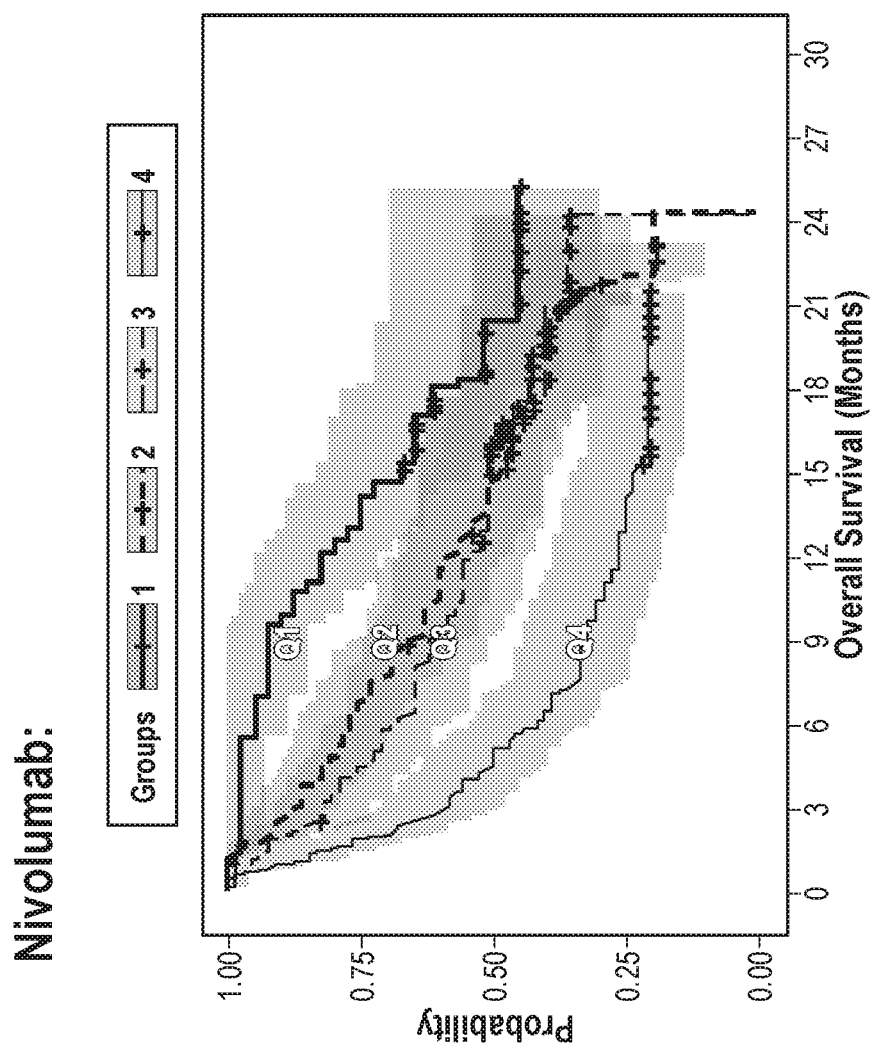
Figure 2C:
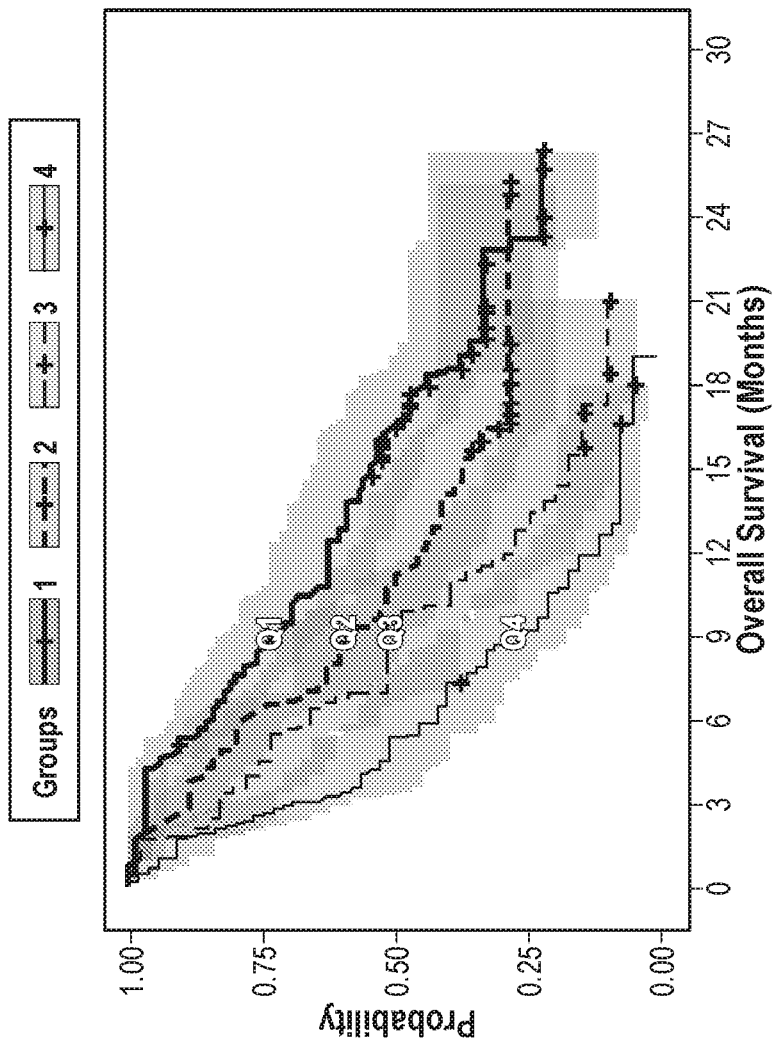
Figure 3A:
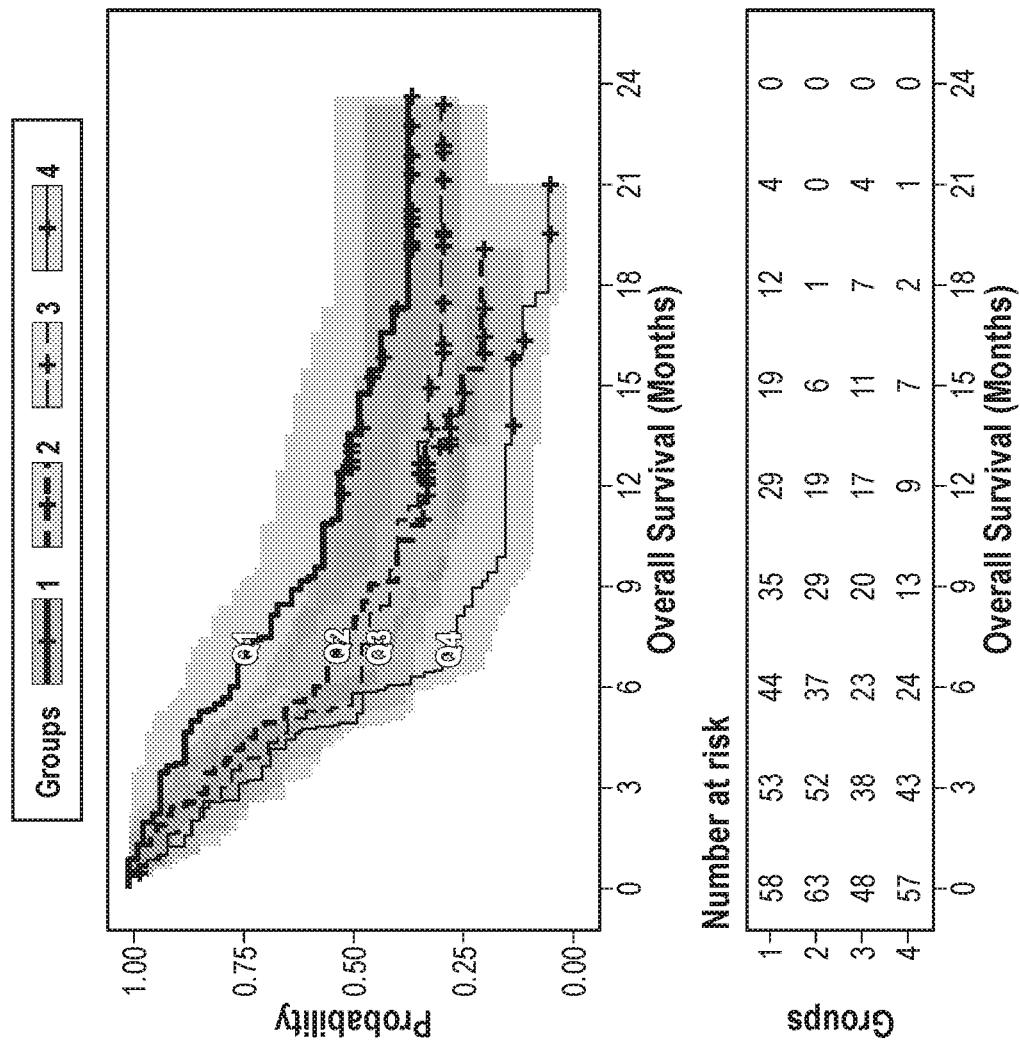
FIGS. 3A-3C are KM-Plots of overall survival (OS) by IL-8 baseline quartiles (Q1 being the lowest quartile by serum IL-8 baseline level) in study CA209-017, for all treated subjects (A), subjects treated with nivolumab (B), or subjects treated with Docetaxel (C). The analysis shows that baseline IL-8 is prognostic for OS.
Figure 3B:
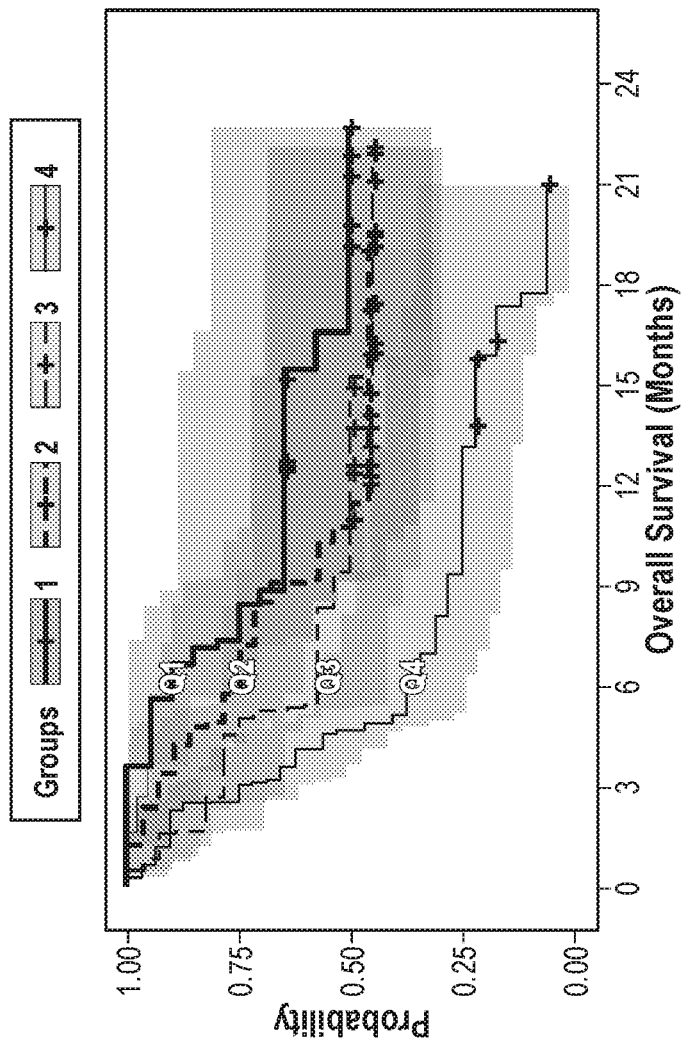
Figure 3C:
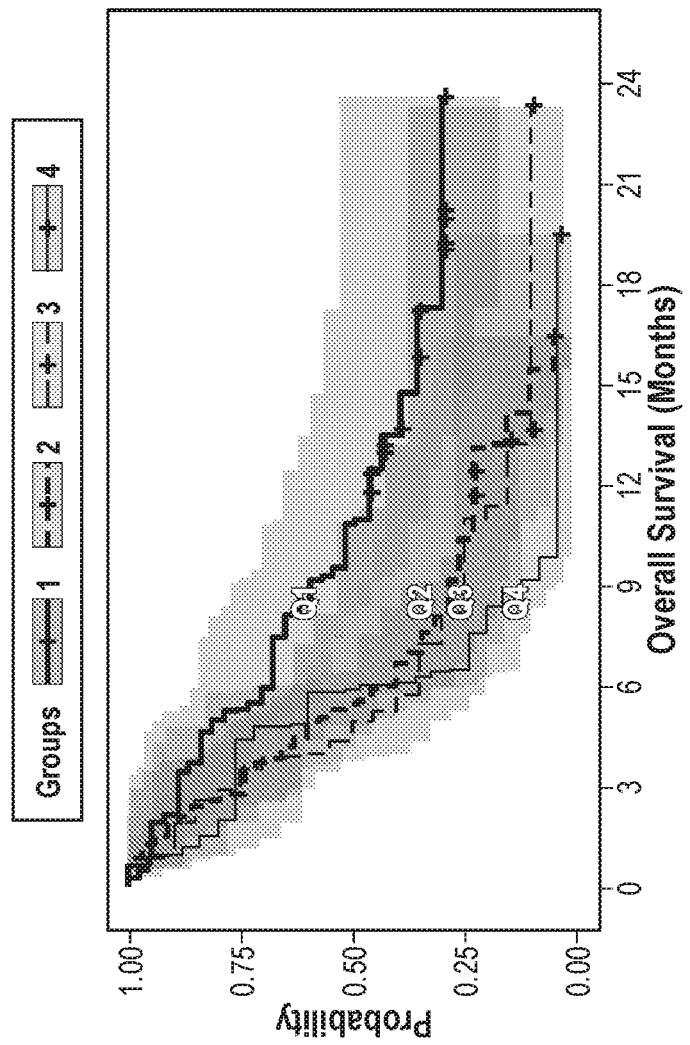
Figure 4A:
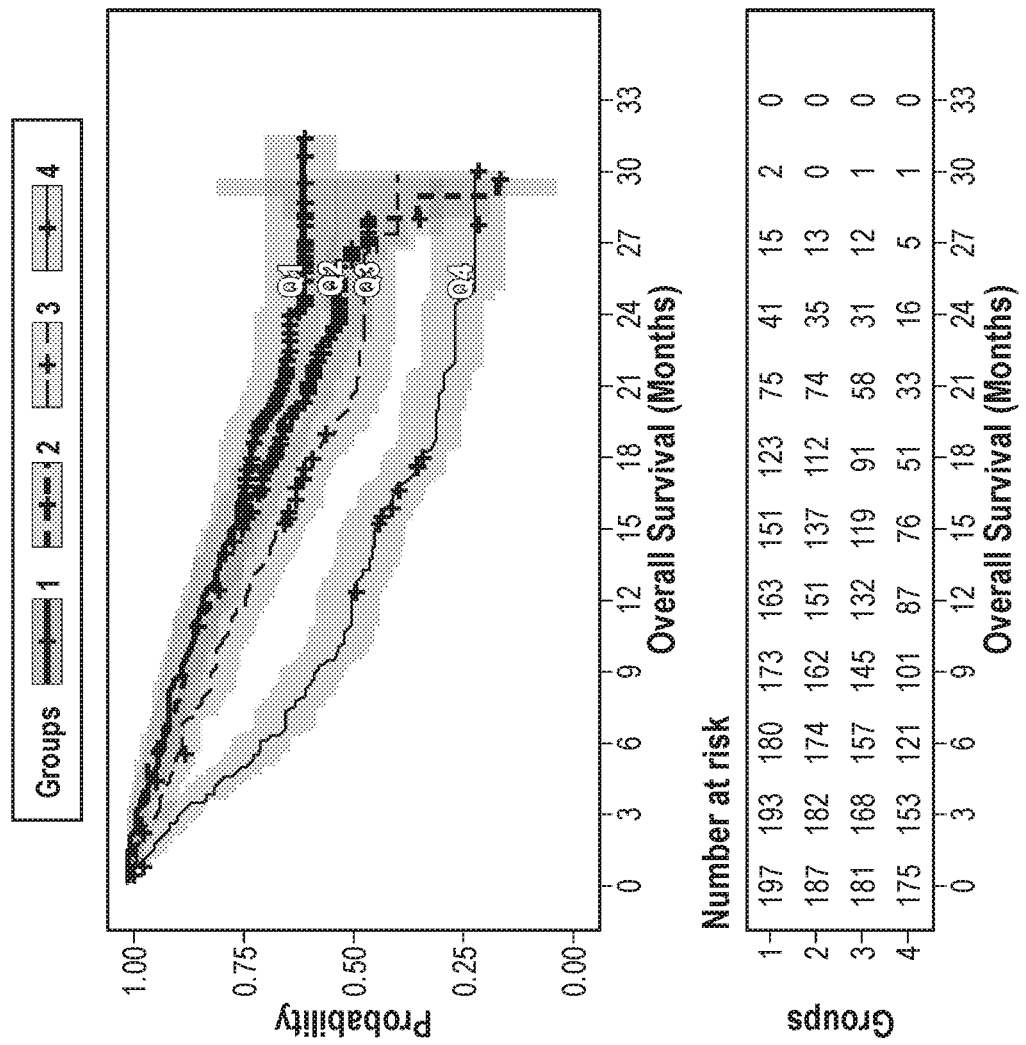
FIGS. 4A-4C are KM-Plots of overall survival (OS) by IL-8 baseline quartiles (Q1 being the lowest quartile by serum IL-8 baseline level) in study CA209-025, for all treated subjects (FIG. 4A), subjects treated with nivolumab (FIG. 4B), or subjects treated with Everolimus (FIG. 4C). The analysis shows that baseline IL-8 is prognostic for OS.
Figure 4B:
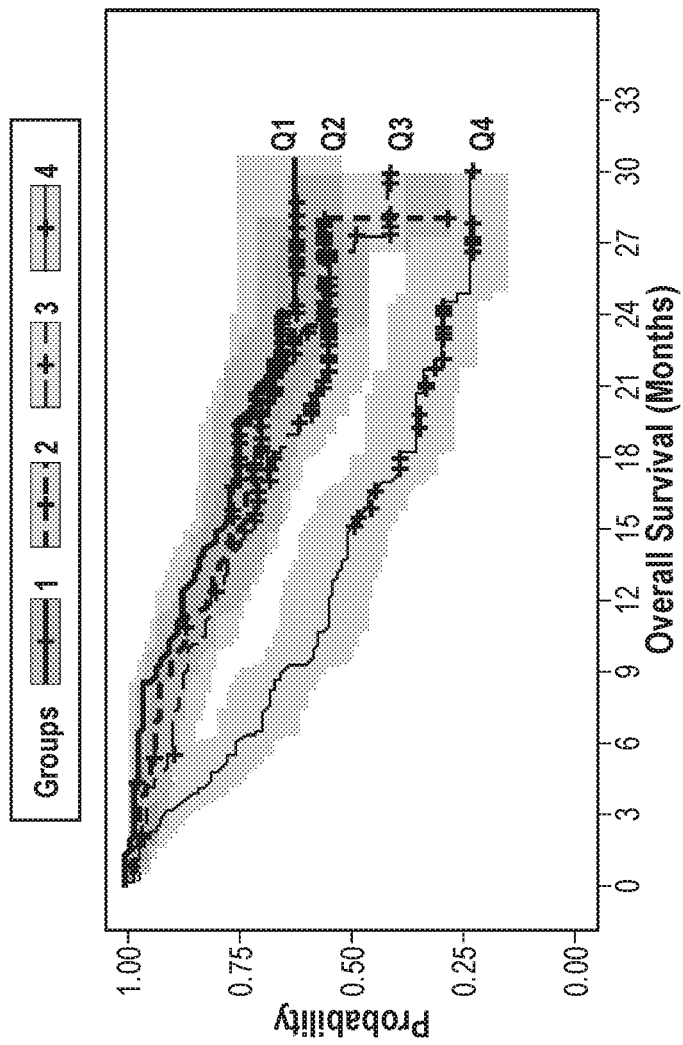
Figure 4C:
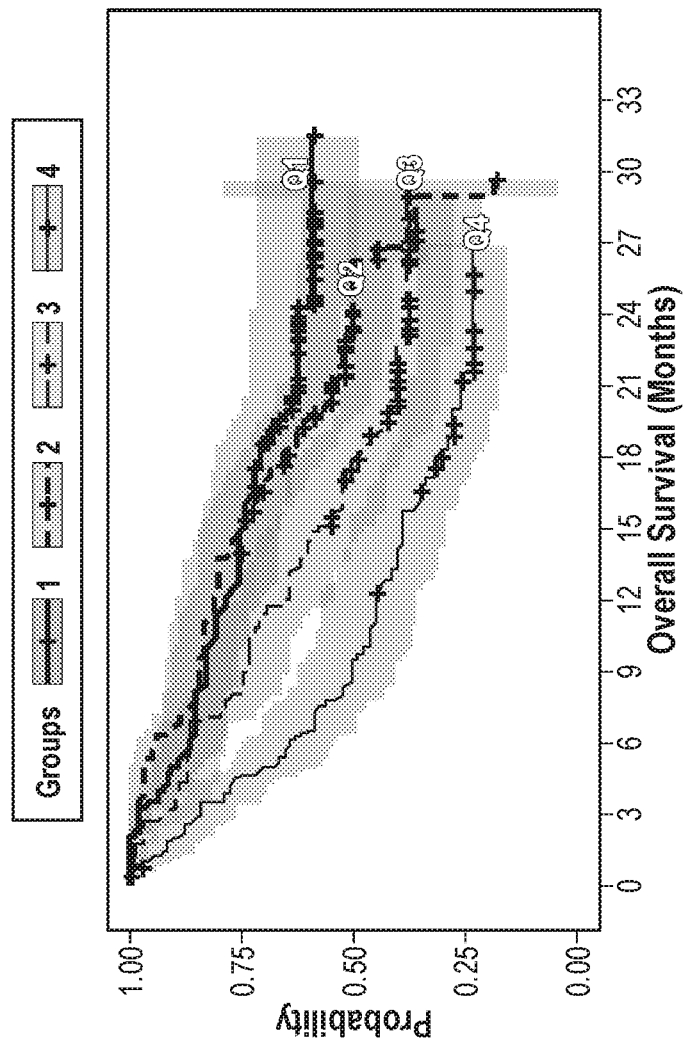
Figure 5:
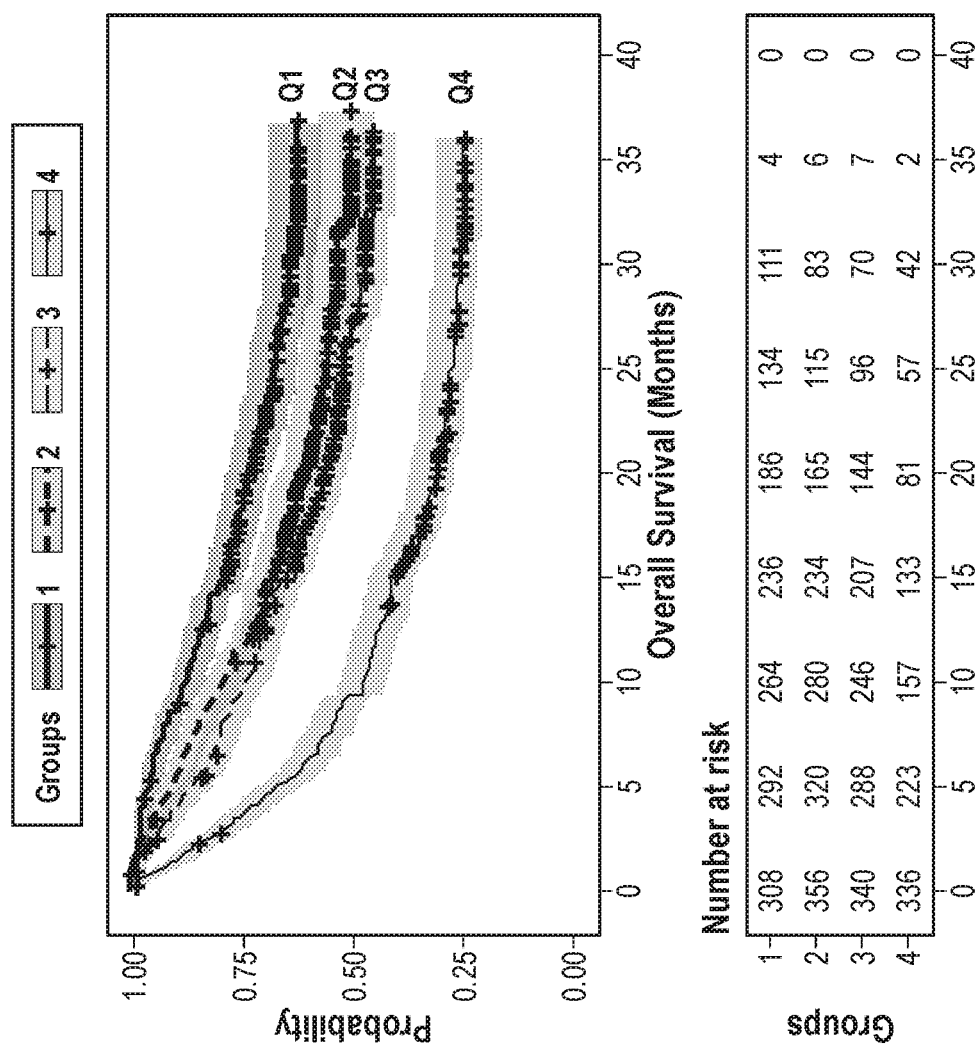
FIG. 5 is a KM-Plot of overall survival (OS) by IL-8 baseline quartiles (Q1 being the lowest quartile by serum IL-8 baseline level) for all pooled subjects treated with nivolumab containing therapy only. The analysis shows that baseline IL-8 is prognostic for OS.

Provided herein are methods of treatment of cancer with anti-IL-8 antibodies (e.g., HuMax-IL8) and anti-PD-1 antibodies (e.g., nivolumab) in patients with certain baseline levels of serum IL-8.

Definitions

In order that the present description may be more readily understood, certain terms are first defined. Additional definitions are set forth throughout the detailed description.

The terms "IL-8" as used herein refers to interleukin-8, which is also referred to in the art as neutrophil-activating protein, neutrophil chemotactic factor, and T-cell chemotactic factor. The term also refers to and includes any variants or isoforms which are naturally expressed by cells or are expressed by cells transfected with the IL-8 gene.

The term "antibody" as used to herein includes whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., IgG1, exist in several allotypes, which differ from each other in at most a few amino acids. "Antibody" includes, by way of example, both naturally occurring and non-naturally occurring antibodies; monoclonal and polyclonal antibodies; chimeric and humanized antibodies; human and nonhuman antibodies; wholly synthetic antibodies; and single chain antibodies. An antibody can be part of an antibody multimer (or multimeric antibody), e.g., dimer, trimer, tetramer, pentamer and hexamer.

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

An "isolated antibody," as used herein, is intended to refer to an antibody which is substantially free of other antibodies having different antigenic specificities.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that down-regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE 2000 instrument using the predetermined antigen, as the analyte and the antibody as the ligand, or Scatchard analysis of binding of the antibody to antigen positive cells, and (ii) binds to the predetermined antigen with an affinity that is at least twofold greater than its affinity for binding to a non-specific antigen (e.g., BSA, casein) other than the predetermined antigen or a closely-related antigen.

Also provided are "conservative sequence modifications" of the sequences set forth herein, i.e., sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into a sequence by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10): 879-884 (1999); and Burks et al. *Proc. Natl. Acad. Sci. USA* 94:412-417 (1997)).

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences (i.e., % homology=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

As used herein, "administering" refers to the physical introduction of a composition comprising a therapeutic agent to a subject, using any of the various methods and delivery systems known to those skilled in the art, e.g., intravenous. Routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient, and/or to prolong survival of the patient, such as progression-free survival or overall survival. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In other preferred embodiments described herein, tumor regression may be observed and continue for a period of at least about 20 days, more preferably at least about 40 days, or even more preferably at least about 60 days.

The term "patient" includes human and other mammalian subjects that receive either prophylactic or therapeutic treatment.

As used herein, the term "subject" includes any human or non-human animal. For example, the methods and compositions described herein can be used to treat a subject having cancer.

As used herein, the term "about" refers to any value which lies within the range defined by a number up to ±10% of the value.

Anti-IL-8 Antibodies

The anti-IL-8 antibodies suitable for use in the methods described herein may be monoclonal antibodies. Antigen binding fragments of such antibodies may also be used. Exemplary anti-IL-8 antibodies, or antigen-binding fragments thereof, which can be used in the methods described herein include, but are not limited to, those disclosed in U.S. Pat. No. 7,282,568 (the contents of which are herein incorporated by reference). Other art-recognized anti-IL-8 antibodies can also be used, for example, the anti-IL8 antibodies disclosed in patent application publications such as WO2009026117, WO2013166099, WO2014149733, WO2015017146, WO2015010100, WO2013106489, WO2013106485, U.S. Pat. No. 5,831,032, WO2006113643, US20050142136, WO2002077172, WO199858671, WO2003080117, WO200009560, WO199602576, WO1996022785, WO1997001354, WO199837200, and WO199937779, which are incorporated herein by reference. Also contemplated for use in the methods described herein are antibodies that compete with any of the art-recognized anti-IL-8 antibodies for binding to IL-8.

In one embodiment, the anti-IL-8 antibody, or antigen-binding portion thereof, may be 10F8 disclosed in U.S. Pat. No. 7,282,568 (also referred to as HuMax-IL8). Accordingly, in one embodiment, the anti-IL-8 antibody, or antigen binding fragment thereof, comprises the CDR1, CDR2, and CDR3 domains of a heavy chain variable region having the sequence set forth in SEQ ID NO: 7, and the CDR1, CDR2, and CDR3 domains of a light chain variable region having the sequence set forth in SEQ ID NO: 8.

In another embodiment, the anti-IL-8 antibody, or antigen binding fragment thereof, comprises heavy chain CDR1, CDR2, and CDR3 sequences set forth SEQ ID NOs: 1-3, and light chain CDR1, CDR2, and CDR3 sequences set forth in SEQ ID NOs: 4-6.

In certain embodiments, the anti-IL-8 antibody has one or more of the following characteristics:

(a) inhibits IL-8 binding to its receptors (CXCR1 and CXCR2);

(b) inhibits IL-8 induced proinflammatory effects;

(c) inhibits IL-8 induced chemotactic activity for neutrophils;

(d) inhibits IL-8 induced calcium influx;

(e) inhibits IL-8 induced changes in expression levels of adhesion molecules on neutrophils;

(f) inhibits IL-8 induced increased expression of CD11b (Mac-1) and inhibits IL-8 induced decreased expression of L-selectin on neutrophils;

(g) does not cross-react with related chemokines selected from the group consisting of human GRO-alpha, human GRO-beta, human IP-10, and human NAP-2;

(h) significantly inhibits chemotaxis induced by biological fluids which contain multiple chemotactic factors including IL-8.

In another embodiment, the anti-IL-8 antibody, or antigen binding fragment thereof, comprises a heavy chain variable region comprising the sequence set forth in SEQ ID NO: 7, and a light chain variable region comprising the sequence set forth in SEQ ID NO: 8.

In another embodiment, the anti-IL-8 antibody, or antigen binding fragment thereof, comprises a heavy chain comprising the sequence set forth in SEQ ID NO: 9, and a light chain comprising the sequence set forth in SEQ ID NO: 10.

In certain embodiments, the anti-IL-8 antibody comprises heavy and light chain variable region sequences that are at least 85%, 90%, 95%, 98%, or 99% identical with the heavy and light chain variable region sequences set forth in SEQ ID NOs: 7 and 8, respectively.

In certain embodiments, the anti-IL-8 antibody comprises heavy and light chain sequences that are at least 85%, 90%, 95%, 98%, or 99% identical with the heavy and light chain sequences set forth in SEQ ID NOs: 9 and 10, respectively.

In certain embodiments, the anti-IL-8 antibody is of an isotype selected from IgG1, IgG2, IgG3, IgG4, IgM, IgA1, IgA2, secretory IgA, IgD, and IgE.

In certain embodiments, the anti-IL-8 antibody has an Fc region with one or more art-recognized alterations in order to change functional or pharmacokinetic properties of the antibody (e.g., decreased or increased Clq binding, complement-dependent toxicity (CDC), FcγR binding, antibody-dependent cellular toxicity (ADCC), and FcRn binding).

Antibodies and antigen binding fragments thereof may be obtained using hybridoma and recombinant procedures well known in the art, such as those described in U.S. Pat. Nos. 4,376,110; 5,427,098; 5,508,717; 5,780,279; 5,571,698; 6,040,136; 7,427,665; 7,435,412; 7,408,041, Kohler and Milstein (1975) Nature 256:495-497; Harlow and Lane, Antibodies: a Laboratory Manual (1988) Cold Spring Harbor; Smith et al., Science 1985; 225:1315-7; Parmley and Smith Gene 1988; 73:305-18; De La Cruz et al., JBC 1988; 263:4318-22; David et al., Cancer Metastasis Rev 1999; 18:421-5; Taylor et al., Nucleic Acids research 1992; 20:6287-95; Tomizuka et al., PNAS 2000; 97:722-7 (the contents of each of the above are herein incorporated by reference). For instance, the antibodies described herein can be produced by culturing a host cell (e.g., *E. coli* or a eukaryotic cells such as CHO cells, NS/0 cells, HEK293 cells, plant cells, fungi, yeast cells), which has been transformed with an expression vector that includes one or more expression cassettes containing a promoter operably linked to a first DNA sequence encoding a signal peptide linked in proper reading frame to a second DNA sequence encoding the antibody protein. The antibody protein can then be collected and isolated. Detailed methods for producing human IL-8 antibodies (e.g., 10F8) using transgenic mice such as HuMAb mice, are extensively described in U.S. Pat. No. 7,282,568, the entire contents of which are herein incorporated by reference.

Anti-PD-1 and PD-L1 Antibodies

An anti-IL-8 antibody may be administered with an anti-PD-1 antibody or an anti-PD-L1 antibody. PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

HuMAbs that bind specifically to PD-1 with high affinity have been disclosed in U.S. Pat. Nos. 8,008,449 and 8,779,105. Other anti-PD-1 monoclonal antibodies have been described in, for example, U.S. Pat. Nos. 6,808,710, 7,488,802, 8,168,757 and 8,354,509, and PCT Publication No. WO 2012/145493. Each of the anti-PD-1 HuMAbs disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies useful for the present invention include antibodies that bind specifically to human PD-1 and exhibit at least one, preferably at least five, of the preceding characteristics.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9): 846-56). Nivolumab can also be referred to as BMS-936558, MDX-1106 ONO-4538, or by its CAS Registry No. 946414-94-4, and is disclosed as antibody 5C4 in WO 2006/121168, incorporated herein by reference in its entirety and for all purposes. Nivolumab is a human monoclonal antibody that specifically binds to PD-1 and comprises a heavy chain variable region provided as SEQ ID NO: 17, and a light chain variable region provided as SEQ ID NO: 18. Nivolumab may also be described as an antibody comprising a heavy chain CDR1 having amino acids 24-34 of SEQ ID NO: 17, a heavy chain CDR2 having amino acids 50-56 of SEQ ID NO: 17, and a heavy chain CDR3 having amino acids 89-97 of SEQ ID NO: 17; and comprising a light chain CDR1 having amino acids 31-35 of SEQ ID NO: 18, a light chain CDR2 having amino acids 50-66 of SEQ ID NO: 18, and a light chain CDR3 having amino acids 99-102 of SEQ ID NO: 18. The heavy and light chain sequences of nivolumab are set forth in SEQ ID NOs: 19 and 20. Also contemplated are anti-PD-1 antibodies comprising heavy and light chain variable region sequences that are at least 85%, 90%, 95%, 98%, or 99% identical with the heavy and light chain variable region sequences set forth in SEQ ID NOs: 17 and 18, respectively. In certain embodiments, the anti-PD-1 antibody comprises heavy and light chain sequences that are at least 85%, 90%, 95%, 98%, or 99% identical with the heavy and light chain sequences set forth in SEQ ID NOs: 19 and 20, respectively. Pharmaceutical compositions of nivolumab include all pharmaceutically acceptable compositions comprising nivolumab and one or more diluents, vehicles and/or excipients. Nivolumab may be administered by I.V.

In one embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also http://www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody is MEDI0608 (formerly AMP-514), which is a monoclonal antibody. MEDI0608 is described, for example, in U.S. Pat. No. 8,609,089B2 or in http://www.cancer.gov/drugdictionary?cdrid=756047 (last accessed Dec. 14, 2014).

In some embodiments, the anti-PD-1 antibody is Pidilizumab (CT-011), which is a humanized monoclonal antibody. Pidilizumab is described in U.S. Pat. No. 8,686,119 B2 or WO 2013/014668 A1. The specificity of CT-011 for PD-1 binding has been questioned.

Anti-PD-1 antibodies useful for the disclosed compositions also include isolated antibodies that bind specifically to human PD-1 and compete or cross-compete for binding to human PD-1 with nivolumab (see, e.g., U.S. Pat. Nos. 8,008,449 and 8,779,105; WO 2013/173223) or other anti-PD-1 antibodies.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibodies or antigen-binding portion thereof cross-competes with nivolumab for binding to human PD-1. In other embodiments, the anti-PD-1 antibodies or antigen-binding portion thereof is a chimeric, humanized or human monoclonal antibodies or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014). In yet other embodiments, the antibody comprises a light chain constant region which is a human kappa or lambda constant region. In other embodiments, the anti-PD-1 antibody or antigen-binding portion thereof is a monoclonal antibody or an antigen-binding portion thereof. In certain embodiments of any of the therapeutic methods described herein comprising administration of an anti-PD-1 antibody, the anti-PD-1 antibody is nivolumab. In other embodiments, the anti-PD-1 Ab is pembrolizumab. In other embodiments, the anti-PD-1 antibody is chosen from the human antibodies 17D8, 2D3, 4H1, 4A11, 7D3 and 5F[4] described in U.S. Pat. No. 8,008,449. In still other embodiments, the anti-PD-1 Ab is MEDI0608 (formerly AMP-514), AMP-224, or Pidilizumab (CT-011).

In certain embodiments, the antibody to be administered with an anti-IL-8 antibody is an anti-PD-L1 antibody. Because anti-PD-1 and anti-PD-L1 target the same signaling pathway and have been shown in clinical trials to exhibit similar levels of efficacy in a variety of cancers, an anti-PD-L1 antibody can be substituted for the anti-PD-1 antibody in any of the therapeutic methods or compositions disclosed herein. In one embodiment, the anti-PD-L1 antibody is BMS-936559 (formerly 12A4 or MDX-1105) (see, e.g., U.S. Pat. No. 7,943,743; WO 2013/173223), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In certain embodiments, an anti-PD-L1 antibody is MEDI4736 (also known as Anti-B7-H1), MPDL3280A (also known as RG7446, atezolizumab and TECENTRIQ), MSB0010718C (WO2013/79174), or rHigM12B7. Any of the anti-PD-L1 antibodies disclosed in WO2013/173223, WO2011/066389, WO2012/145493, U.S. Pat. Nos. 7,635,757 and 8,217,149 and U.S. Publication No. 2009/145493 may also be used. Anti-PD-L1 antibodies that compete with and/or bind to the same epitope as that of any of these antibodies may also be used in the treatments described herein.

Thus, generally, a PD-1/PD-L1 antagonist agent that may be used in the methods described herein include nivolumab, pembrolizumab, atelozilumab, durvalumab, REGN2810, PDR001, AMP-514 (MEDI0608), AMP-224, BGB-A317 or a PD-1 or PD-L1 antagonist described in any one of the following publications: WO 2009/014708, WO 03/099196, WO 2009/114335 and WO 2011/161699.

Pharmaceutical Compositions

Further provided are compositions, e.g., a pharmaceutical compositions, containing anti-IL-8 antibodies in combination with anti-PD-1 antibodies (e.g., nivolumab), formulated together or separately with a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion).

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein may also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Methods of Treating Cancer/Treatment Protocols

Provided herein are methods of treating a subject having cancer (e.g., an advanced solid tumor) with a combination therapy comprising an anti-IL-8 antibody and an anti-PD-1 antibody, wherein the baseline serum IL-8 levels in the subject is above the lower limit of quantitation (LLOQ). Serum IL-8 levels can be detected using standard assays known in the art, such as commercial ELISA that detects both the monomer and dimer form of IL-8 (e.g., Human IL-8 ELISA set; BD Bioescience Pharmingen). In some embodiments, the subjects have baseline serum IL-8 levels of at least or >10 pg/ml, 9 pg/mL, 8 pg/mL, 7 pg/mL, 6 pg/mL, 5 pg/mL, 4 pg/mL, 3 pg/mL, 2 pg/mL, or 1 pg/mL, e.g., as assessed by ELISA (e.g., sandwich ELISA). In some embodiments, the subjects have baseline serum IL-8 levels >10 pg/ml.

In certain embodiments, an anti-IL-8 antibody may be administered to a subject having cancer, e.g., an advanced solid tumor, as a combination therapy with an anti-PD-1 antibody at a flat dose of 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, or 3000 mg of an anti-IL-8 antibody, once every week, once every two weeks, once every 3 weeks, once every 4 weeks, once every 5 weeks, once every 6 weeks, once every 7 weeks, or once every 8 weeks. The treatment may be administered in, e.g., 2-week cycles or 4-week cycles, e.g., one 4-week cycle, two 4-week cycles, three 4-week cycles, four 4-week cycles, five 4-week cycles, six 4-week cycles, or more, for example, up to, e.g., 26 4-week cycles. In certain embodiments, one cycle is 28 days long.

In certain embodiments, the anti-IL-8 antibody and anti-PD-1 antibody may be administered on Day 1 of each cycle.

In some embodiments, the anti-PD-1 antibody may be administered at a flat dose of, e.g., 100-500 mg, 200 mg-500 mg, 300-500 mg, 400-500 mg, 450-500 mg, 460-490 mg, 470-490 mg, 240 mg, 360 mg, or 480 mg.

Exemplary combination therapies comprise an anti-IL-8 antibody and an anti-PD-1 antibody. In certain embodiments, an anti-IL-8 antibody may be administered first, followed by an administration of a PD-1 antibody. For example, an anti-IL-8 antibody, may be administered by infusion for a period of 60-120 minutes, followed by an infusion of an anti-PD-1 antibody over a period of 30-60 minutes. In certain embodiments, an anti-PD-1 antibody may be administered by infusion for a period of 30-60 minutes, followed by an infusion of an anti-IL-8 antibody over a period of 60-120 minutes.

In one embodiment, an anti-IL-8 antibody may be administered at a flat dose of 2400 mg or about 2400 mg by infusion for 120 minutes. In another embodiment, an anti-IL-8 antibody may be administered at a flat dose of 1200 mg or about 1200 mg by infusion for 60 minutes. In another embodiment, an anti-IL-8 antibody may be administered at a flat dose of 600 mg or about 600 mg by infusion for 60 minutes. In some embodiments, an anti-PD-1 antibody may be administered at a flat dose of 480 mg or about 480 mg by infusion for 30 minutes.

In one embodiment, an anti-IL-8 antibody (e.g., 10F8 or HuMax-IL8) may be administered at a flat dose of 2400 mg or about 2400 mg by infusion for 120 minutes, followed by an observation period of 30 minutes, and then an anti-PD-1 antibody (e.g., nivolumab) may be administered at a flat dose of 480 mg by infusion for 30 minutes.

In one embodiment, an anti-IL-8 antibody (e.g., 10F8 or HuMax-IL8) may be administered at a flat dose of 1200 mg or about 1200 mg by infusion for 60 minutes, followed by an observation period of 30 minutes, and then an anti-PD-1 antibody (e.g., nivolumab) may be administered at a flat dose of 480 mg by infusion for 30 minutes.

In one embodiment, an anti-IL-8 antibody (e.g., 10F8 or HuMax-IL8) may be administered at a flat dose of 600 mg or about 600 mg by infusion for 60 minutes, followed by an observation period of 30 minutes, and then an anti-PD-1 antibody (e.g., nivolumab) may be administered at a flat dose of 480 mg by infusion for 30 minutes.

In certain embodiments, the anti-IL-8 antibody and anti-PD-1 antibody may be administered at the same time, and may be coformulated.

An exemplary combination therapy comprises administering an anti-IL-8 antibody in combination with nivolumab. Nivolumab may be administered at a flat dose of 240 mg, 360 mg, or 480 mg every two or four weeks.

An anti-IL-8 antibody (e.g., 10F8 or HuMax-IL8) for administration by infusion may be provided as a formulation of 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml or more. In a certain embodiment, the anti-IL-8 antibody may be provided as a formulation of 20 mg/ml.

An anti-PD-1 antibody (e.g., nivolumab) for administration by infusion, may be provided as a formulation of 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml or more. In a certain embodiment, the anti-PD-1 antibody may be provided as a formulation of 10 mg/ml.

An exemplary combination treatment comprises administering to a subject having an advanced solid tumor a 600 mg flat dose of an anti-IL-8 antibody and an anti-PD-1 antibody (e.g., nivolumab) at a flat dose of 480 mg, administered together or separately, as one or two IV infusions, e.g., over 30-60 minutes each, every 2 or 4 weeks.

A treatment may comprise administering to a subject having an advanced solid tumor a 1200 mg flat dose of an anti-IL-8 antibody and an anti-PD-1 antibody at a flat dose of 480 mg, administered together or separately, as one or two IV infusions, e.g., over 30-60 minutes each, every 2 or 4 weeks.

A treatment may comprise administering to a subject having an advanced solid tumor a 2400 mg flat dose of an anti-IL-8 antibody and an anti-PD-1 antibody at a flat dose of 480 mg, administered together or separately, as one or two IV infusions, e.g., over 30-120 minutes each, every 2 or 4 weeks.

Suitable protocols for treating a solid tumor (e.g., an advanced solid tumor) in a human subject with detectable levels of serum IL-8 include, for example, administering to a subject an effective amount of each of:

(a) an anti-IL-8 antibody comprising CDR1, CDR2 and CDR3 domains of the heavy chain variable region having the sequence set forth in SEQ ID NO: 7, and CDR1, CDR2 and CDR3 domains of the light chain variable region having the sequence set forth in SEQ ID NO: 8, and (b) an anti-PD-1 antibody comprising CDR1, CDR2 and CDR3 domains of the heavy chain variable region having the sequence set forth in SEQ ID NO: 17, and CDR1, CDR2 and CDR3 domains of the light chain variable region having the sequence set forth in SEQ ID NO: 18.

In some embodiments, the method may comprise at least one administration cycle. In some embodiments, the at least one administration cycle may be a period of one week or 7 days, 2 weeks or 14 days, 3 weeks or 21 days, 4 weeks or 28 days, 5 weeks or 35 days, or 6 weeks or 42 days. In some embodiments, for each of the at least one cycles, one dose of the anti-IL-8 antibody may be administered at a fixed dose ranging from 100 mg to 10,000 mg, from 200 mg to 400 mg, from 400 mg to 600 mg, from 600 mg to 800 mg, from 800 mg to 1000 mg, from 1000 mg to 1200 mg, from 1200 mg to 1400 mg, from 1400 mg to 1600 mg, from 1600 mg to 1800 mg, from 1800 mg to 2000 mg, from 2000 mg to 2200 mg, from 2200 mg to 2400 mg, from 2400 mg to 3000 mg, from 3000 mg to 3600 mg, or from 3600 mg to 5000 mg. In some embodiments, one dose of the anti-IL-8 antibody may be administered at a fixed dose of 600 mg, 1200 mg, or 2400 mg, or a fixed dose of about 600 mg, 1200 mg, or 2400 mg. In some embodiments, one dose of the anti-PD-1 antibody may be administered at a dose ranging from 120 mg to 600 mg, from 240 mg to 360 mg, or from 360 to 480 mg. In some embodiments, one dose of the anti-PD-1 antibody may be administered at flat dose of 120 mg, 240 mg, 360 mg, or 480 mg, or a flat dose of about 120 mg, 240 mg, 360 mg, or 480 mg.

In some embodiments, the treatment consists of up to 13 cycles. In some embodiments, the treatment consists of up to 26 cycles. In some embodiments, the treatment consists of up to 52 cycles.

In certain embodiments, the cancer in the patient has progressed or relapsed after an anti-PD-1 or anti-PD-L1 therapy. Accordingly, in some embodiments, the anti-IL-8 antibody and anti-PD-1 antibody may be administered as a second line of treatment (e.g., after the initial or first treatment, including after relapse and/or where the first treatment has failed, e.g., after first line PD-(L)1 treatment).

In some embodiments, the anti-IL-8 antibody and anti-PD-1 antibody may be administered at the following doses:

(a) 2400 mg anti-IL-8 antibody and 240 mg, 360 mg, or 480 mg of anti-PD-1 antibody;

(b) 1200 mg anti-IL-8 antibody and 240 mg, 360 mg, or 480 mg of anti-PD-1 antibody; or (c) 600 mg anti-IL-8 antibody and 240 mg, 360 mg, or 480 mg of anti-PD-1 antibody.

In some embodiments, the dose of the anti-IL-8 and/or anti-PD-1 antibody may be varied over time. For example, the anti-IL-8 and/or anti-PD-1 antibody may be initially administered at a high dose and may be lowered over time. In another embodiment, the anti-IL-8 and/or anti-PD-1 antibody may be initially administered at a low dose and increased over time.

In another aspect, the invention features any of the aforementioned embodiments, wherein the anti-PD-1 antibody is replaced by, or combined with, an anti-PD-L1 or anti-PD-L2 antibody.

In certain embodiments, the anti-IL-8 antibody comprises a heavy chain variable region CDR1 comprising the sequence set forth in SEQ ID NO: 1, a heavy chain variable region CDR2 comprising the sequence set forth in SEQ ID NO: 2, a heavy chain variable region CDR3 comprising the sequence set forth in SEQ ID NO: 3, a light chain variable region CDR1 comprising the sequence set forth in SEQ ID NO: 4, a light chain variable region CDR2 comprising the sequence set forth in SEQ ID NO: 5, and a light chain variable region CDR3 comprising the sequence set forth in SEQ ID NO: 6. In certain embodiments, the anti-IL-8 antibody comprises heavy and light chain variable regions comprising the sequences set forth in SEQ ID NOs: 7 and 8, respectively. In certain embodiments, the anti-IL-8 antibody comprises heavy and light chain sequences comprising the sequences set forth in SEQ ID NOs: 9 and 10, respectively. In certain embodiments, the anti-IL-8 antibody comprises heavy and light chain variable region sequences that are at least 85%, 90%, 95%, 98%, or 99% identical with the heavy and light chain variable region sequences set forth in SEQ ID NOs: 7 and 8, respectively. In certain embodiments, the anti-IL-8 antibody comprises heavy and light chain sequences that are at least 85%, 90%, 95%, 98%, or 99% identical with the heavy and light chain sequences set forth in SEQ ID NOs: 9 and 10, respectively.

In certain embodiments, the anti-PD-1 antibody comprises a heavy chain variable region CDR1, CDR2, and CDR3 comprising the sequences set forth in SEQ ID NOs: 11-13, respectively, and light chain variable region CDR1, CDR2, and CDR3 comprising the sequences set forth in SEQ ID NOs: 14-16, respectively. In certain embodiments, the anti-PD-1 antibody comprises heavy and light chain variable regions sequences set forth in SEQ ID NOs: 17 and 18, respectively. In certain embodiments, the anti-PD-1 antibody comprises heavy and light chain sequences set forth in SEQ ID NOs: 19 and 20, respectively. In certain embodiments, the anti-PD-1 antibody comprises heavy and light chain variable region sequences that are at least 85%, 90%, 95%, 98%, or 99% identical with the heavy and light chain variable region sequences set forth in SEQ ID NOs: 17 and 18, respectively. In certain embodiments, the anti-PD-1 antibody comprises heavy and light chain sequences that are at least 85%, 90%, 95%, 98%, or 99% identical with the heavy and light chain sequences set forth in SEQ ID NOs: 19 and 20, respectively.

In certain embodiments, an anti-IL-8 antibody may be administered to subjects who have a solid tumor associated with a cancer selected from the group consisting of: melanoma, non-small cell lung carcinoma (NSCLC), renal cell carcinoma (RCC), triple negative breast cancer (TNBC), colorectal cancer (CRC), pancreatic ductal adenocarcinoma (PDA), and hepatocellular carcinoma (HCC).

In some embodiments, the solid tumor may be selected from melanoma, non-small cell lung carcinoma (NSCLC), squamous NSCLC, non-squamous NSCLC, renal cell carcinoma, triple negative breast cancer, colorectal cancer, pancreatic ductal adenocarcinoma, and hepatocellular carcinoma, esophageal cancer, gastric cancer, rectal cancer, squamous cell carcinoma of the head and neck (SCCHN), small cell lung cancer (SCLC), prostate cancer, e.g., metastatic castration-resistant prostate cancer (mCRPC) or castration-sensitive prostate cancer (CSPC), glioblastoma multiforme (GBM), bladder cancer, neoplasm of the central nervous system (CNS), primary CNS lymphoma, spinal axis tumor, brain cancer, brain stem glioma, head and neck cancer, pancreatic cancer (PAC), liver cancer, hepatoma, stomach cancer, kidney cancer, colon carcinoma, germ cell tumor, pediatric sarcoma, sinonasal natural killer, skin cancer, bone cancer, breast cancer, cervical cancer, carcinoma of the cervix, uterine cancer, carcinoma of the fallopian tubes, ovarian cancer, endometrial cancer, carcinoma of the endometrium, carcinoma of the vagina, carcinoma of the vulva, cancer of the anal region, testicular cancer, gastrointestinal cancer, cancer of the esophagus, cancer of the small intestine, cancer of the endocrine system, thyroid cancer, cancer of the parathyroid gland, cancer of the adrenal gland, sarcoma of soft tissue, cancer of the urethra, cancer of the ureter, cancer of the penis, carcinoma of the renal pelvis, pituitary adenoma, rhabdomyosarcoma, Kaposi's sarcoma, epidermoid cancer, squamous cell cancer, solid tumors of childhood, environmentally-induced cancers, virus-related cancers, cancers of viral origin, and any combination of these cancers. In certain embodiments, the cancer is an advanced, unresectable, metastatic, refractory cancer, and/or recurrent cancer.

In some embodiments, the methods described herein may be used to treat a cancer which is a hematological malignancy. Hematological malignancies include liquid tumors derived from either of the two major blood cell lineages, i.e., the myeloid cell line (which produces granulocytes, erythrocytes, thrombocytes, macrophages and mast cells) or the lymphoid cell line (which produces B, T, NK and plasma cells), including all types of leukemias, lymphomas, and myelomas. Hematological malignancies that may be treated using the present combination therapy methods include, for example, cancers selected from acute lymphoblastic leukemia (ALL), acute myelogenous leukemia (AML), chronic lymphocytic leukemia (CLL), chronic myelogenous leukemia (CML), Hodgkin's lymphoma (HL), non-Hodgkin's lymphomas (NHLs), multiple myeloma, smoldering myeloma, monoclonal gammopathy of undetermined significance (MGUS), advanced, metastatic, refractory and/or recurrent hematological malignancies, and any combinations of said hematological malignancies. In some embodiments, the hematological malignancy is a cancer selected from acute, chronic, lymphocytic (lymphoblastic) and/or myelogenous leukemias, such as ALL, AML, CLL, and CML; lymphomas, such as HL, NHLs, of which about 85% are B cell lymphomas, including diffuse large B-cell lymphoma (DLBCL), follicular lymphoma (FL), chronic lymphocytic leukemia (CLL)/small lymphocytic lymphoma (SLL), mantle cell lymphoma, marginal zone B-cell lymphomas (mucosa-associated lymphoid tissue (MALT) lymphoma, nodal marginal zone B-cell lymphoma, and splenic marginal zone B-cell lymphoma), Burkitt lymphoma, lymphoplasmacytoid lymphoma (LPL; also known as Waldenström's macroglobulinemia (WM)), hairy cell lymphoma, and primary central nervous system (CNS) lymphoma, NHLs that are T cell lymphomas, including precursor T-lymphoblastic lymphoma/leukemia, T-lymphoblastic lymphoma/leukemia (T-Lbly/T-ALL), peripheral T-cell lymphomas such as cutaneous T-cell lymphoma (CTLC, i.e., mycosis fungoides, Sezary syndrome and others), adult T-cell lymphoma/leukemia, angioimmunoblastic T-cell lymphoma, extranodal natural killer/T-cell lymphoma nasal type, enteropathy-associated intestinal T-cell lymphoma (EATL), anaplastic large-cell lymphoma (ALCL), and peripheral T-cell lymphoma unspecified, acute myeloid lymphoma, lymphoplasmacytoid lymphoma, monocytoid B cell lymphoma, angiocentric lymphoma, intestinal T-cell lymphoma, primary mediastinal B-cell lymphoma, post-transplantation lymphoproliferative disorder, true histiocytic lymphoma, primary effusion lymphoma, diffuse histiocytic lymphoma (DHL), immunoblastic large cell lymphoma, and precursor B-lymphoblastic lymphoma; myelomas, such as multiple myeloma, smoldering myeloma (also called indolent myeloma), monoclonal gammopathy of undetermined significance (MGUS), solitary plasmocytoma, IgG myeloma, light chain myeloma, nonsecretory myeloma, and amyloidosis; and any combinations of said hematological malignancies. The present methods are also applicable to treatment of advanced, metastatic, refractory and/or recurrent hematological malignancies.

In some embodiments, the tumor is metastatic. In some embodiments, the tumor is recurrent. In some embodiments, the tumor is unresectable. In some embodiments, the tumor is metastatic, recurrent, and/or unresectable.

In some embodiments, the subject has a cancer selected from non-small cell lung cancer (NSCLC), head and neck squamous cell carcinoma (HNSCC), melanoma, bladder cancer, pancreatic cancer, gastric cancer, colon cancer, renal cell carcinoma (RCC), small-cell lung cancer (SCLC), triple negative breast cancer (TNBC), colorectal cancer (CRC), hepatocellular carcinoma (HCC), mesothelioma, prostate cancer, e.g., metastatic castration-resistant prostate cancer (mCRPC) or castration-sensitive prostate cancer (CSPC), multiple myeloma, and combinations of said cancers. In some embodiments, the subject has a cancer selected from NSCLC, melanoma, RCC, TNBC, CRC, HCC, pancreatic cancer, and combinations of said cancers. In some embodiments, the subject has a cancer selected from NSCLC, melanoma and RCC and combinations of said cancers. In some embodiments, the subject has prostate cancer, e.g., metastatic castration-resistant prostate cancer (mCRPC) or castration-sensitive prostate cancer (CSPC).

In some embodiments, an anti-IL-8 antibody may be administered in combination with an anti-PD-1 antibody (e.g., nivolumab). In some embodiments, an anti-IL-8 antibody may be administered in combination with an anti-PD-1 antibody (e.g., nivolumab) in subjects with histologic or cytologic confirmation of a solid tumor that is advanced (metastatic, recurrent and/or unresectable) with measurable disease per RECIST v1.1, and have an Eastern Cooperative Oncology Group Performance Status of 0 or 1.

In certain embodiments in which subjects having a solid tumor, e.g., advanced solid tumor, such as NSCLC, are treated with an anti-IL-8 antibody as combination therapy with an anti-PD-1 antibody (e.g., nivolumab), the subjects have histologically or cytologically confirmed, advanced (i.e., unresectable or metastatic) NSCLC of either squamous or non-squamous histology; the subjects have had radiologically documented progressive or recurrent disease either during or within 3 months after anti-PD-(L)1 therapy (administered as monotherapy or as part of a combination); the subjects have not had intervening systemic therapy between anti-PD-(L)1 treatment and the combination treatment; the subjects have documented PD-(L)1 status; the subjects have received platinum-based chemotherapy in the recurrent or metastatic setting; the subjects have a known EGFR and ALK status; and/or the subjects have prior progression or intolerance to an approved therapy if they harbor a genetic alteration.

In certain embodiments in which subjects having a solid tumor, e.g., advanced solid tumor, such as RCC (e.g., with a clear cell component), are treated with an anti-IL-8 antibody as combination therapy with an anti-PD-1 antibody (e.g., nivolumab), the subjects have radiologically documented progressive or recurrent disease either during or within 3 months after anti-PD-(L)1 therapy (administered as monotherapy or as part of a combination); the subjects have had no intervening systemic therapy between anti-PD-(L)1 treatment and the combination treatment; and/or subjects have received at least 1 but not more than 2 prior anti-angiogenic therapy regimens (including but not limited to bevacizumab, axitinib, cabozantinib, pazopanib, sorafenib, sunitinib and tivozanib) in the advanced or metastatic setting.

In certain embodiments in which subjects having a solid tumor, e.g., advanced solid tumor, such as melanoma, are treated with an anti-IL-8 antibody, as combination therapy with an anti-PD-1 or anti-PD-L1 antibody, e.g., nivolumab, the subjects have histologically confirmed, unresectable Stage III or Stage IV melanoma, as specified in the American Joint Committee on Cancer staging system; the subjects have a documented PD-L1 status; the subjects have radiologically documented progressive or recurrent disease either during or within 3 months after anti-PD-(L)1 monotherapy or after anti-PD-(L)1 component of the combination therapy with other agent including but not limited to anti-CTLA-4; and/or the subjects have a known BRAF (V600) mutation status.

In certain embodiments in which subjects having a solid tumor, e.g., advanced solid tumor, such as triple negative breast cancer (TNBC), are treated with an anti-IL-8 antibody as combination therapy with an anti-PD-1 or anti-PD-L1 antibody, e.g., nivolumab, the subjects have histologically documented, locally advanced, unresectable, or metastatic TNBC; the subjects have a negative estrogen receptor/progesterone receptor and HER2 status; and/or the subjects have radiologically documented progression on, or after, or been intolerant to (or are not candidates for) at least 1 line of standard therapy.

In certain embodiments in which subjects having a solid tumor, e.g., advanced solid tumor, such as colorectal cancer (CRC), are treated with an anti-IL-8 antibody as combination therapy with an anti-PD-1 or anti-PD-L1 antibody, e.g., nivolumab, the subjects have histologically documented, locally advanced, unresectable, or metastatic CRC; the subjects have known microsatellite instability status (MSS) (e.g., expression of MLH1, MSH2, MSH6, and PMS2 by immunohistochemistry (IHC) or absence of instability in microsatellite markers by polymerase chain reaction (PCR)); the subjects have radiologically documented progression on, or after, or been intolerant to (or are not candidates for) at least 1 line of standard therapy.

In certain embodiments in which subjects having a solid tumor, e.g., advanced solid tumor, such as pancreatic ductal carcinoma (PDC), are treated with an anti-IL-8 antibody as combination therapy with an anti-PD-1 or anti-PD-L1 antibody, e.g., nivolumab, the subjects have histologically documented, locally advanced, unresectable, or metastatic PDC; and/or the subjects have radiologically documented progression on, or after, or been intolerant to (or are not candidates for) at least 1 line of standard therapy.

In certain embodiments in which subjects having a solid tumor, e.g., advanced solid tumor, such as hepatocellular carcinoma (HCC), are treated with an anti-IL-8 antibody, as combination therapy with an anti-PD-1 or anti-PD-L1 antibody, e.g., nivolumab, the subjects have histologically documented HCC that is ineligible for ablative techniques or liver transplant; the subjects, who progressed after locoregional therapy for HCC, have completed the locoregional therapy for HCC at least 4 weeks prior to the baseline scan; the subjects have resolved all acute toxic effects of any prior local treatment to National Cancer Institute (NCI) Common Terminology Criteria for Adverse Events (CTCAE) v4.03 Grade >1 or been deemed irreversible; the subjects have previous progressive disease, or been intolerant to, at least 1 line of therapy or refused treatment with sorafenib; the subjects have a Child-Pugh Class A (6 points or less); the subjects have a known status for hepatitis B surface antigen, hepatitis B surface antibody, hepatitis B core antibody, hepatitis B deoxyribonucleic acid (DNA) PCR, hepatitis C antibody and hepatitis C ribonucleic acid (RNA) PCR; the subjects, who have hepatitis B infection, have a hepatitis B DNA viral load <100 IU/mL and are on anti-viral therapy; the subjects, who have hepatitis B infection, have no co-infection with hepatitis C or hepatitis D; the subjects, who have HCV infection, are on anti-viral therapy.

In certain embodiments of the methods described herein, the subjects may be treated with an anti-IL-8 antibody, as combination therapy with an anti-PD-1 or anti-PD-L1 antibody, e.g., nivolumab, and an anti-CTLA-4 antibody, e.g., ipilimumab.

In certain embodiments of the methods described herein, the subjects have serum IL-8 levels above the LLOQ. In some embodiments, the subjects have baseline serum IL-8 levels >10 pg/ml as assessed, e.g., by sandwich ELISA. In some embodiments, the subjects have baseline serum IL-8 levels >0.1 pg/mL, >1 pg/mL, >2 pg/mL, >3 pg/mL, >4 pg/mL, >5 pg/ml, >6 pg/ml, >7 pg/ml, >8 pg/ml, >9 pg/ml, >10 pg/ml, >11 pg/ml, >12 pg/ml, >13 pg/ml, >14 pg/ml, >15 pg/ml, >16 pg/ml, >17 pg/ml, >18 pg/ml, >19 pg/ml, >20 pg/ml, >21 pg/ml, >22 pg/ml, >23 pg/ml, >24 pg/ml, >25 pg/ml, >26 pg/ml, >27 pg/ml, >28 pg/ml, >29 pg/ml, >30 pg/ml, >31 pg/ml, >32 pg/ml, >33 pg/ml, >34 pg/ml, >35 pg/ml, >40 pg/ml, >45 pg/ml, or >50 pg/ml. In some embodiments, the subjects have baseline serum IL-8 levels of at least 1 pg/ml, 2 pg/ml, 3 pg/ml, 4 pg/ml, 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, 20 pg/ml, 21 pg/ml, 22 pg/ml, 23 pg/ml, 24 pg/ml, 25 pg/ml, 26 pg/ml, 27 pg/ml, 28 pg/ml, 29 pg/ml, 30 pg/ml, 31 pg/ml, 32 pg/ml, 33 pg/ml, 34 pg/ml, 35 pg/ml, 40 pg/ml, 45 pg/ml, 50 pg/ml, 55 pg/ml, 60 pg/ml, 65 pg/ml, 70 pg/ml, 75 pg/ml, or 80 pg/ml. In some embodiments, the subjects have baseline serum IL-8 levels of at least 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, 20 pg/ml, 21 pg/ml, 22 pg/ml, 23 pg/ml, 24 pg/ml, 25 pg/ml, 26 pg/ml, 27 pg/ml, 28 pg/ml, 29 pg/ml, or 30 pg/ml. In some embodiments, the subjects have baseline serum IL-8 levels of at least 20 pg/ml, 21 pg/ml, 22 pg/ml, 23 pg/ml, 24 pg/ml, or 25 pg/ml. In some embodiments, the subjects have baseline serum IL-8 levels of at least 26 pg/ml, 27 pg/ml, 28 pg/ml, 29 pg/ml, or 30 pg/ml. In some embodiments, the subjects have baseline serum IL-8 levels of less than or equal to 15 pg/ml, 16 pg/ml, 17 pg/ml, 18 pg/ml, 19 pg/ml, 20 pg/ml, 21 pg/ml, 22 pg/ml, 23 pg/ml, 24 pg/ml, 25 pg/ml, 26 pg/ml, 27 pg/ml, 28 pg/ml, 29 pg/ml, 30 pg/ml, 32 pg/ml, 34 pg/ml, 36 pg/ml, 38 pg/ml, 40 pg/ml, 42 pg/ml, 44 pg/ml, 46 pg/ml, 48 pg/ml, or 50 pg/ml. In some embodiments, the subjects have baseline serum IL-8 levels of less than or equal to 23 pg/ml, 24 pg/ml, 25 pg/ml, 26 pg/ml, 27 pg/ml, 28 pg/ml, 29 pg/ml, or 30 pg/ml. In some embodiments, the subjects have baseline serum IL-8 levels of less than or equal to 23 pg/ml. In some embodiments, the subjects have baseline serum IL-8 levels of 1-300 pg/ml, 5-300 pg/ml, 5-150 pg/ml, 10-150 pg/ml, 10-120 pg/ml, 10-100 pg/ml, 10-80 pg/ml, 10-60 pg/ml, 10-40 pg/ml, 10-30 pg/ml, or 10-20 pg/ml. In some embodiments, the subjects have baseline serum IL-8 levels of 10-30 pg/ml, 10-25 pg/ml, 10-23 pg/ml, 10-20 pg/ml, 10-15 pg/ml, 12-30 pg/ml, 12-25 pg/ml, 12-23 pg/ml, 12-20 pg/ml, 12-15 pg/ml, 15-30 pg/ml, 15-25 pg/ml, 15-23 pg/ml, 20-30 pg/ml, 25-35 pg/ml, 30-40 pg/ml, 35-45 pg/ml, 15-20 pg/ml, 20-25 pg/ml, 25-30 pg/ml, 30-35 pg/ml, or 35-50 pg/ml. In some embodiments, the subjects have baseline serum IL-8 levels of 10-15 pg/ml, 10-16 pg/ml, 10-17 pg/ml, 10-18 pg/ml, 10-19 pg/ml, 10-20 pg/ml, 10-21 pg/ml, 10-22 pg/ml, 10-23 pg/ml, 10-24 pg/ml, 10-25 pg/ml, 15-18 pg/ml, 15-20 pg/ml, 15-23, pg/ml, 15-25 pg/ml, 18-20 pg/ml, 18-23 pg/ml, 18-25 pg/ml, 20-22 pg/ml, 22-24 pg/ml, 24-26 pg/ml, 26-28 pg/ml, or 28-30 pg/ml. In some embodiments, the subjects have baseline serum IL-8 levels of 10-50 pg/ml, 10-40 pg/ml, 10-30 pg/ml, 10-25 pg/ml, 10-23 pg/ml, or 10-20 pg/ml.

In certain embodiments, the subjects have baseline serum IL-8 levels >10 pg/mL; adequate hematologic function defined as 1) Neutrophils ≥1,500 μ/L, 2) Platelets ≥80×10³/μL, and 3) Hemoglobin ≥8 g/dL; adequate hepatic function defined as 1) ALT and AST ≤3×ULN limit of normal (ULN), 2) Total bilirubin ≤1.5×ULN (except subjects with Gilbert's Syndrome who must have normal direct bilirubin), 3) Prothrombin time-international normalized ratio ≤2.3 or prothrombin time ≤6 seconds above control for those with HCC, 4) Adequate hepatic function as documented by (a) Serum albumin ≥2.8 g/dL, (b) Total bilirubin ≤3 mg/dL, (c) AST and ALT ≤5× the institutional ULN for those with HCC; normal thyroid function or stable on hormone supplementation; and/or Serum creatinine ≤1.5×ULN or creatinine clearance (CrCl)≥40 ml/min (measured using the Cockcroft-Gault formula below): Female CrCl=(140−age in years)× weight in kg×0.85 72×serum creatinine in mg/dL Male CrCl=(140−age in years)×weight in kg×1.00 72×serum creatinine in mg/dL.

A patient receiving a treatment described herein may be a patient having one or more of the inclusion criteria set forth in Example 1, or not having one or more of the exclusion criteria set forth in Example 1.

In certain embodiments in which subjects having a solid tumor, e.g., advanced solid tumor, such as melanoma, non-small cell lung carcinoma (NSCLC), renal cell carcinoma (RCC), triple negative breast cancer (TNBC), colorectal cancer (CRC), pancreatic ductal adenocarcinoma (PDA), and hepatocellular carcinoma (HCC), are treated with an anti-IL-8 antibody as combination therapy with an anti-PD-1 antibody (e.g., nivolumab), the subjects have no known or suspected primary CNS malignancies, or tumors with CNS metastases as the only site of disease, except that the subject may have controlled brain metastases (i.e., no radiographic progression for at least 4 weeks following radiation and/or surgical treatment (or 4 weeks of observation if no intervention is clinically indicated), and off of steroids for at least 2 weeks, and no new or progressive neurological signs and symptoms.

Anti-tumor activity of an anti-IL-8 antibody (e.g., 10F8 or HuMax-IL8) in combination with an anti-PD-1 antibody (e.g., nivolumab), and optionally an anti-CTLA-4 antibody (e.g., ipilimumab), may be evidenced by an increase in overall survival relative to a subject treated with a placebo. Efficacy of treatment may be determined by measurement of the objective response rate (ORR). ORR and corresponding 2-sided exact 95% exact confidence interval by the Clopper and Pearson method may be determined. Median duration of response and corresponding two-sided 95% confidence interval may be determined. Duration of response may be analyzed using the Kaplan-Meier method and corresponding two-sided 95% CI using Brookmeyer and Crowley methodology.

Outcomes

With respect to target lesions, responses to therapy may include:

| | |
|---|---|
| Complete Response (CR) (RECIST V1.1) | Disappearance of all target lesions. Any pathological lymph nodes (whether target or non-target) must have reduction in short axis to <10 mm. |

| | |
|---|---|
| Partial Response (PR) (RECIST V1.1) | At least a 30% decrease in the sum of the diameters of target lesions, taking as reference the baseline sum diameters. |
| Progressive Disease (PD) (RECIST V1.1) | At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) (RECIST V1.1) | Neither sufficient shrinkage to qualify for PR nor sufficient increase to qualify for PD, taking as reference the smallest sum diameters while on study. |
| Immune-related Complete Response (irCR) (irRECIST) | Disappearance of all target lesions. Any pathological lymph nodes (whether target or non-target) must have reduction in short axis to <10 mm. |
| Immune-related Partial Response (irPR) (irRECIST) | At least a 30% decrease in the sum of diameters of target lesions and all new measurable lesions (ie Percentage Change in Tumor Burden), taking as reference the baseline sum diameters. Note: the appearance of new measurable lesions is factored into the overall Tumor Burden, but does not automatically qualify as progressive disease until the sum of the diameters increases by ≥20% when compared to nadir. |
| Immune-related Progressive Disease (irPD) (irRECIST) | At least a 20% increase in Tumor Burden (ie the sum of diameters of target lesions, and any new measurable lesions) taking as reference the smallest sum on study (this includes the baseline sum if that is the smallest on study). In addition to the relative increase of 20%, the sum must also demonstrate an absolute increase of at least 5 mm. Tumor assessments using immune-related criteria for progressive disease incorporates the contribution of new measurable lesions. Each net percentage change in tumor burden per assessment accounts for the size and growth kinetics of both old and new lesions as they appear. |
| Immune-related Stable Disease (irSD) (irRECIST) | Neither sufficient shrinkage to qualify for irPR nor sufficient increase to qualify for irPD, taking as reference the smallest sum diameters while on study. |

With respect to non-target lesions, responses to therapy may include:

| | |
|---|---|
| Complete Response (CR) (RECIST V1.1) | Disappearance of all non-target lesions. All lymph nodes must be non-pathological in size (<10 mm short axis). |
| Non-CR/Non-PD (RECIST V1.1) | Persistence of one or more non-target lesion(s). |
| Progressive Disease (PD) (RECIST V1.1) | Unequivocal progression of existing non-target lesions. The appearance of one or more new lesions is also considered progression. |
| Immune-related Complete Response (irCR) (irRECIST) | Disappearance of all non-target lesions. All lymph nodes must be non-pathological in size (<10 mm short axis). |
| Immune-related Progressive Disease (irPD) (irRECIST) | Increases in number or size of non-target lesion(s) does not constitute progressive disease unless/until Tumor Burden increases by 20% (ie the sum of the diameters at nadir of target lesions and any new measurable lesions increases by the required amount). Non-target lesions are not considered in the definition of Stable Disease and Partial Response. |

Subjects treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the subject treated exhibits a complete response (CR), a partial response (PR), stable disease (SD), immune-related complete disease (irCR), immune-related partial response (irPR), or immune-related stable disease (irSD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent. In some embodiments, the methods described herein produce at least one therapeutic effect chosen from prolonged survival, such as progress free survival or overall survival, optionally compared to another therapy or placebo.

In other embodiments, administration of effective amounts of the anti-IL-8 antibody and anti-PD-1 antibody, and optionally anti-CTLA-4 antibody, according to any of the methods provided herein produces at least one therapeutic effect selected from the group consisting of reduction in size of a tumor, reduction in number of metastatic lesions appearing over time, complete remission, partial remission, or stable disease. In still other embodiments, the methods of treatment produce a comparable clinical benefit rate (CBR=CR+PR+SD ≥6 months) better than that achieved by an anti-IL-8 antibody or anti-PD-1 antibody alone. In other embodiments, the improvement of clinical benefit rate is about 20% 20%, 30%, 40%, 50%, 60%, 70%, 80% or more compared to an anti-IL-8 antibody or anti-PD-1 antibody alone.

Kits

Also provided herein are kits which include a pharmaceutical composition containing an anti-IL-8 antibody, such as 10F8 or HuMax-IL8, and an anti-PD-1 antibody, and a pharmaceutically-acceptable carrier, in a therapeutically effective amount adapted for use in the methods described herein. In some embodiments, the kit further comprises an anti-CTLA-4 antibody, such as ipilimumab. The kits optionally also can include instructions, e.g., comprising administration schedules, to allow a practitioner (e.g., a physician, nurse, or patient) to administer the composition contained therein to administer the composition to a patient having cancer (e.g., a solid tumor). The kit also can include a syringe.

Optionally, the kits include multiple packages of the single-dose pharmaceutical compositions each containing an effective amount of the anti-IL-8 or anti-PD-1 antibody for a single administration in accordance with the methods provided above. Instruments or devices necessary for administering the pharmaceutical composition(s) also may be included in the kits. For instance, a kit may provide one or more pre-filled syringes containing an amount of the anti-IL-8 or anti-PD-1 antibody.

In one embodiment, provided herein is a kit for treating a solid tumor in a human subject, the kit comprising:

(a) a dose of an anti-IL-8 antibody comprising CDR1, CDR2 and CDR3 domains of the heavy chain variable region having the sequence set forth in SEQ ID NO: 7, and CDR1, CDR2 and CDR3 domains of the light chain variable region having the sequence set forth in SEQ ID NO: 8;

(b) a dose of an anti-PD-1 antibody comprising CDR1, CDR2 and CDR3 domains of the heavy chain variable region having the sequence set forth in SEQ ID NO: 9, and CDR1, CDR2 and CDR3 domains of the light chain variable region having the sequence set forth in SEQ ID NO: 10; and (c) instructions for using the anti-IL-8 antibody and anti-PD-1 antibody in the methods described herein.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1: Phase 1b/2 Trial in Patients Having Advanced Solid Tumors

A phase 1b/2 trial of an anti-IL-8 antibody (HuMax-IL8) and an anti-PD-1 antibody (nivolumab) is conducted in patients having advanced solid tumors to demonstrate the efficacy of administering the two therapeutics as a combination treatment.

Study Population

Subjects must be at least 18 years of age and have histologic or cytologic confirmation of a solid tumor that is advanced (i.e., metastatic, recurrent, and/or unresectable) with measurable disease per Response Evaluation Criteria in Solid Tumors (RECIST) v1.1, and have at least 1 lesion accessible for biopsy. Subjects must have a detectable serum level of IL-8 at baseline.

Objectives

The primary objective is to characterize the safety, tolerability, and DLTs, and to determine the RP2D of HuMax-IL8 administered in combination with nivolumab in subjects with advanced solid tumors.

Secondary objectives include evaluating the preliminary efficacy of HuMax-IL8 in combination with nivolumab in subjects with advanced solid tumors, characterizing the PK and immunogenicity of HuMax-IL8 administered in combination with nivolumab in subjects with advanced solids tumors, and assessing serum IL-8 levels at baseline (i.e., screening) and changes in IL-8 levels on treatment.

Exploratory objectives include measuring MDSC, assessing MDSC changes over time and in association with response, characterizing selected biomarker measures in the tumor and peripheral blood and explore their potential association with anti-tumor activity prior to treatment and following administration of HuMax-IL8 in combination with nivolumab, exploring associations between HuMax-IL8 serum PK, safety, efficacy, and clinical biomarkers, assessing PFS and OS in subjects treated with HuMax-IL8 in combination with nivolumab, characterizing the PK and immunogenicity of nivolumab when administered in combination with HuMax-IL8, and assessing the potential effect of HuMax-IL8 on QTc interval.

Study Design

This is a Phase 1b/2, open-label study of HuMax-IL8 administered in combination with nivolumab in subjects with advanced solid tumors (i.e., metastatic, recurrent, and/or unresectable) who have detectable levels of serum IL-8. The study is comprised of 2 parts. The first part includes a safety evaluation lead-in followed by a randomized dose-finding phase. The second part includes a dose expansion phase.

Part 1: Safety Evaluation Lead-in and Randomized Dose-Finding Phase The safety of HuMax-IL8 in combination with nivolumab is evaluated in subjects with refractory melanoma non-small cell lung cancer (NSCLC) or renal cell carcinoma (RCC) who have progressed on or relapsed after anti-PD-(L)1 therapy. The safety evaluation lead-in (Part 1A) begins with a cohort of subjects who receive a 2,400 mg flat dose of HuMax-IL8 combined with a 480 mg flat dose of nivolumab every 4 weeks (Q4W). A slightly higher dose (32 mg/kg or 2,560 mg administered every 2 weeks [Q2W]; yielding an overall dose of 64 mg/kg or 5,120 mg per month) of HuMax-IL8 monotherapy has been shown to be safe and well tolerated. Safety is confirmed based on use of the Bayesian Logistic Regression Model-Copula method and assessment of available safety data for the first 4 participants. After review of the clinical safety assessment of the first 4 participants, the dose-limiting toxicity (DLT) and the totality of available data, the randomized, dose-finding phase (Part 1B) is initiated. Up to 56 additional subjects are enrolled into Part 1B to determine the recommended Phase 2 dose (RP2D) of HuMax-IL8. Subjects are assigned in a 1:1:1 ratio to Cohorts B1, B2, and B3, respectively, so that approximately 20 subjects are treated in parallel in each cohort. Dosing for each cohort is as follows:

Cohort B1: 2,400 mg of BMS-986253 and 480 mg of nivolumab Q4W

Cohort B2: 1,200 mg of BMS-986253 and 480 mg of nivolumab Q4W

Cohort B3: 600 mg of BMS-986253 and 480 mg of nivolumab Q4W

In the event that the safety lead-in cohort of Part 1A recommends evaluation of a lower dose of BMS-986253 (1,200 mg) prior to starting the randomized dose-finding phase, a cohort of 4 subjects is treated with BMS-986253 (1,200 mg) in combination with 480 mg of nivolumab Q4W. If there are no safety concerns after the clinical safety assessment, then subjects will be randomized in a 1:1 ratio to Cohorts B2 and B3, respectively, so that up to approximately 20 subjects are eventually be treated in Cohorts B2 and B3. The RP2D is determined based on the totality of data available from the dose ranges evaluated in Part 1A and 1B to define the safe and most biologically active dose.

Part 2: Dose Expansion Phase

After determination of the RP2D from Part 1, the dose expansion phase (Part 2) is initiated to gather additional safety, tolerability, preliminary efficacy, pharmacokinetic (PK), and pharmacodynamic (PD) information in specific patient populations. Subjects with anti-PD-(L)1 refractory melanoma, RCC, or NSCLC, as well as subjects with advanced triple-negative breast cancer, colorectal cancer, pancreatic ductal adenocarcinoma, or HCC who have failed prior therapies are enrolled in up to 7 independent cohorts. Each anti-PD-(L)1 refractory cohort consists of up to 40 subjects treated at the RP2D of HuMax-IL8 in combination with nivolumab, and each signal seeking cohort consists of up to 20 subjects treated at the RP2D of HuMax-IL8 in combination with nivolumab. Subjects with serum 11-8 above the lower limit of quantitation are enrolled into one of each of the cohorts based on tumor type.

Treatment

HuMax-IL8 is administered in combination with nivolumab once Q4W (or 28 days), defined as 1 cycle of the treatment period. All subjects are treated for up to 104 weeks (2 years) (corresponding to 26 cycles of 28 days each) or until disease progression, intolerance to treatment, meeting discontinuation criteria, or withdrawal of consent.

Doses are determined as follows. In the safety evaluation lead-in phase (Part 1A), a starting dose of 2,400 mg of HuMax-IL8 is administered in combination with 480 mg of nivolumab Q4W. If the 2,400 mg dose is intolerable, a lower dose of HuMax-IL8 (1,200 mg) combined with 480 mg of nivolumab is administered. In the randomized dose-finding phase of study (Part 1B), up to 3 dose levels of HuMax-IL8 (2,400 mg, 1,200 mg, or 600 mg) combined with 480 mg of nivolumab are evaluated in parallel. The highest dose evaluated in Part 1B will not exceed the tolerable dose determined by the safety evaluation phase (Part 1A). In the dose expansion phase (Part 2), the dose will be the RP2D determined in Part 1. The study treatment is shown in Table 1, and the dose and schedule are summarized in Tables 2 and 3.

TABLE 1

| Medication/dosage form | Potency |
| --- | --- |
| BMS-986253 | 20 mg/mL |
| Nivolumab | 10 mg/mL |

TABLE 2

| Study part | Dose | Dose schedule |
| --- | --- | --- |
| Part 1A: Safety Evaluation Lead-in | BMS-986253 2400 mg + nivolumab 480 mg | Q4W |
| Part 1B: Randomized Dose-finding | BMS-986253 2400 mg, 1200 mg, 600 mg + nivolumab 480 mg | Q4W |
| Part 2: Dose Expansion | BMS-986253 RP2D + nivolumab 480 mg | Q4W |

TABLE 3

| Treatment | Flat dose level | Route of administration | Infusion time (minutes) |
| --- | --- | --- | --- |
| BMS-986253 | 2400 mg | IV | 120 |
| BMS-986253 | 1200 mg, 600 mg | IV | 60* |
| Nivolumab | 480 mg | IV | 30 |

*Infusion time for 1200 mg will be 60 minutes with the exception for subjects weighting <35 kg;
if <35 kg, then infusion time will be 120 minutes.

Subjects may be treated beyond progression as long as they meet the criteria. HuMax-IL8 is infused intravenously (IV) first over the recommended time based on the randomization schedule. A 30-minute observation period follows HuMax-IL8 infusion. Nivolumab is then infused over 30 minutes. A 60-minute observation period follows the nivolumab infusion.

Follow-Up

Safety Follow-up Period: Upon completion of study treatment or a decision is made to discontinue treatment, all subjects enter a safety follow-up period. After the end of treatment (EOT) visit, all subjects are evaluated for any new adverse events (AEs) for at least 100 days after the last dose of study treatment. Follow-up visits occur at Days 30, 60, and 100 (±7 days for each visit) after the last dose, or the date of discontinuation (±7 days). All subjects are required to complete 3 clinical safety follow-up visits, regardless of whether new anti-cancer therapy is started.

Response Follow-up Period: At the time of the EOT visit or at the time of study treatment discontinuation, all subjects undergo radiologic and clinical tumor assessments every 12 weeks (Q12W) until subsequent tumor-directed therapy is initiated. Subjects who remain free of subsequent therapy continue to receive tumor assessment scans Q12W for the first year after discontinuation of study treatment/EOT visit. After the first year of follow-up, visits are per standard of care guidelines, at a minimum of every 6 months up to 2 years following the last dose of study treatment. Radiological assessments for subjects who have ongoing clinical benefit and remain free of subsequent therapy may continue to be collected after they complete the survival follow-up period.

Survival Follow-up Period: In parallel with the safety follow-up period, all subjects start the survival follow-up period. Subjects are followed up Q12W (from EOT) for 2 years or until death, loss to follow-up, withdrawal of consent, or conclusion of the study, whichever comes first. The response follow-up and survival follow-up periods occur simultaneously during the 2-year follow-up period.

Study Treatment

Subjects are administered selected IV doses of HuMax-IL8 in combination with nivolumab Q4W. Doses will be determined as follows:

In the safety evaluation lead-in phase (Part 1A), a starting dose of 2,400 mg of HuMax-IL8 is administered in combination with 480 mg of nivolumab Q4W. If the 2,400 mg dose is determined to be intolerable, a lower dose of HuMax-IL8 (1,200 mg) combined with 480 mg of nivolumab will then be evaluated.

In the randomized dose-finding phase of study (Part 1B), up to 3 dose levels of HuMax-IL8 (2,400 mg, 1,200 mg, or 600 mg) combined with 480 mg of nivolumab will be evaluated in parallel. The highest dose evaluated in Part 1B will not exceed the tolerable dose determined by the safety evaluation phase (Part 1A).

In the dose expansion phase (Part 2), the dose will be the RP2D determined in Part 1. At any point during the study, intermediate doses or shorter dosing schedules could be evaluated if necessary.

Inclusion Criteria

1. Target Population

Subjects must have histologic or cytologic confirmation of a solid tumor that is advanced (metastatic, recurrent and/or unresectable) with measurable disease per RECIST v1.1. Subjects must have an Eastern Cooperative Oncology Group Performance Status of 0 or 1. The following tumor histologies are permitted, except for subjects with primary CNS tumors, or with CNS metastases as the only site of active disease.

i) Non-Small Cell Lung Carcinoma

1. Histologically or cytologically confirmed, advanced (i.e., unresectable or metastatic) NSCLC of either squamous or non-squamous histology
2. Must have had radiologically documented progressive or recurrent disease either during or within 3 months after anti-PD-(L)1 therapy (administered as monotherapy or as part of a combination). No intervening systemic therapy is permitted between anti-PD-(L)1 treatment and enrollment.

3. PD-(L)1 status must be documented if available. PD-(L)1 status is also be re-tested using tissue acquired from the mandatory pre-treatment biopsy.
4. Subjects must have received platinum-based chemotherapy in the recurrent or metastatic setting.
5. Epidermal growth factor receptor and anaplastic lymphoma kinase status must be known. ROS and KRAS mutational status should be documented if available. For subjects harboring genetic alteration for which there is an approved therapy specific to the alteration, prior progression or intolerance to that therapy is required.

ii) Renal Cell Carcinoma with a Clear Cell Component.
1. Must have had radiologically documented progressive or recurrent disease either during or within 3 months after anti-PD-(L)1 therapy (administered as monotherapy or as part of a combination). No intervening systemic therapy is permitted between anti-PD-(L)1 treatment and enrollment on this trial.
2. Must have received at least 1 but not more than 2 prior anti-angiogenic therapy regimens (including but not limited to bevacizumab, axitinib, cabozantinib, pazopanib, sorafenib, sunitinib and tivozanib) in the advanced or metastatic setting.

iii) Melanoma
1. Histologically confirmed, unresectable Stage III or Stage IV melanoma, as specified in the American Joint Committee on Cancer staging system.
2. PD-L1 status must be documented if available. PD-L1 status will also be re-tested using tissue acquired from the mandatory pre-treatment biopsy.
3. Must have had radiologically documented progressive or recurrent disease either during or within 3 months after anti-PD-(L)1 monotherapy or after anti-PD-(L)1 component of the combination therapy with other agent including but not limited to anti-CTLA-4. Subjects may have received other systemic therapies for their disease, however anti-PD-(L)1, alone or in combination therapy must have been the most recent therapy administered.
(4) BRAF (V600) mutation status must be known. Both BRAF mutated and wild-type subjects are permitted in this cohort.

iv) Expansion Cohort Only:
1. Subjects must have histologically documented, locally advanced, unresectable, or metastatic cancer of the following histology, that has progressed on, or after, or been intolerant to (or are not candidates for) at least 1 line of standard therapy, if such therapy exists. Subjects must also have been considered for all other potentially efficacious therapies.

v) Triple Negative Breast Cancer
1. Histologically documented, locally advanced, unresectable, or metastatic TNBC.
2. Estrogen receptor/progesterone receptor and HER2 status must be documented and confirmed negative.
3. Must have radiologically documented progression on, or after, or been intolerant to (or are not candidates for) at least 1 line of standard therapy.
4. Subjects must also have been considered for all other potentially efficacious therapies.

vi) Colorectal Cancer
1. Histologically documented, locally advanced, unresectable, or metastatic CRC
2. Microsatellite instability status (MSS) must be documented. Only MSI subjects are permitted in this cohort. Note: MSS is defined as expression of MLH1, MSH2, MSH6, and PMS2 by immunohistochemistry (IHC) or absence of instability in microsatellite markers by polymerase chain reaction (PCR))
3. Must have radiologically documented progression on, or after, or been intolerant to (or are not candidates for) at least 1 line of standard therapy.
4. Subjects must also have been considered for all other potentially efficacious therapies.

vii) Pancreatic Ductal Adenocarcinoma
1. Histologically documented, locally advanced, unresectable, or metastatic
2. Must have radiologically documented progression on, or after, or been intolerant to (or are not candidates for) at least 1 line of standard therapy.
3. Subjects must also have been considered for all other potentially efficacious therapies viii) Hepatocellular Carcinoma
1. For subjects with histologically documented HCC that is ineligible for ablative techniques or liver transplant. For subjects who progressed after locoregional therapy, locoregional therapy for HCC must be completed at least 4 weeks prior to the baseline scan. All acute toxic effects of any prior local treatment must have resolved to National Cancer Institute (NCI) Common Terminology Criteria for Adverse Events (CTCAE) v4.03 Grade >1 or been deemed irreversible.
2. Subjects with radiological diagnosis may be enrolled for screening but histological confirmation is mandatory prior to initiation of study therapy.
3. Previous progressive disease, or been intolerant to, at least 1 line of therapy or refused treatment with sorafenib
4. A Child-Pugh Class A (6 points or less)
5. Must have results of testing for hepatitis B surface antigen, hepatitis B surface antibody, hepatitis B core antibody, hepatitis B deoxyribonucleic acid (DNA) PCR, hepatitis C antibody and hepatitis C ribonucleic acid (RNA) PCR;
6. For subjects with hepatitis B infection, a hepatitis B DNA viral load <100 IU/mL and the subject must be on anti-viral therapy
7. For subjects with hepatitis B infection, no co-infection with hepatitis C or hepatitis D (must obtain hepatitis D antibody testing)
8. For subjects with hepatitis C virus (HCV), active HCV infection, as defined by any detectable HCV RNA and positive antibody titer, can be enrolled providing they are on anti-viral therapy. Resolved HCV infection, as evidenced by undetectable HCV RNA and positive antibody titer, can be enrolled. Subjects on antiviral therapy for HCV are permitted and should continue treatment during the study. Subjects with active HCV who are not on antiviral therapy at screening cannot be enrolled in the study.
9. Other tumor types could be considered at the time of expansion based on scientific rationale and be added to the study by subsequent amendment.

2. Physical and Laboratory Test Findings
Subjects must have:
i) Baseline Serum IL-8 Levels >10 pg/mL
ii) Adequate hematologic function as defined by the following:
1. Neutrophils ≥1,500 µ/L
2. Platelets ≥80×10$^3$/µL (transfusion to achieve this level is not permitted within 2 weeks of first study treatment administration)

3. Hemoglobin ≥8 g/dL (transfusion to achieve this level is not permitted within 2 weeks of first study treatment administration)

iii) Adequate Hepatic Function
1. Alanine aminotransferase (ALT) and aspartate aminotransferase (AST)≤3× upper limit of normal (ULN)
2. Total bilirubin ≤1.5×ULN (except subjects with Gilbert's Syndrome who must have normal direct bilirubin)
3. Specifically for participants with HCC:
   Prothrombin time-international normalized ratio ≤2.3 or prothrombin time ≤6 seconds above control
   Adequate hepatic function as documented by (a) Serum albumin ≥2.8 g/dL; (b) Total bilirubin ≤3 mg/dL; (c) AST and ALT ≤5× the institutional ULN Study Assessments Safety Assessments: Safety assessments are based on AE reports and results of vital signs including oxygen saturation, electrocardiograms, physical examinations, and clinical laboratory tests. AEs are coded using the most current version of Medical Dictionary for Regulatory Activities and the incidence of observed AEs are tabulated and reviewed for potential significance and clinical importance. AEs are assessed continuously during the study and for 100 days after the last dose of HuMax-IL8 combined with nivolumab. Both AEs and laboratory tests are graded using the National Cancer Institute Common Terminology Criteria for Adverse Events v4.03.

PK Assessments: The PK of HuMax-IL8 and nivolumab is derived from serum concentration versus time data over single and multiple dose administrations. The PK parameters that are assessed include: maximum observed plasma concentration (Cmax), time of maximum observed serum concentration (Tmax), area under the serum concentration-time curve (AUC) from time zero to the time of the last quantifiable concentration (AUC(0-T)), AUC in 1 dosing interval (AUC(TAU)), observed serum concentration at the end of a dosing interval (Ctau), Trough observed serum concentrations (this includes pre-dose concentrations [C0] and Ctau) (Ctrough), total body clearance (CLT), average serum concentration over a dosing interval at steady state (Css-avg), accumulation index for AUC and Cmax (AI), and terminal elimination half-life (T-HALF). Individual subject PK parameter values are derived by non-compartmental methods by a validated PK analysis program. Actual times are used for the final analyses.

Immunogenicity Assessments: Serum samples for HuMax-IL8 or nivolumab anti-drug antibodies are collected from all subjects at specified time points. Samples collected from subjects in each treatment arm will be evaluated for development of ADA for HuMax-IL8/nivolumab by validated immunoassays. Samples are also analyzed for neutralizing ADA response to HuMax-IL8/nivolumab. Serum samples designated for PK or biomarker assessments may also be used for immunogenicity analysis if required (e.g., insufficient volume for complete immunogenicity assessment or to follow up on suspected immunogenicity related AE).

Biomarker Assessments: Biomarker measures of baseline and on-treatment peripheral blood, serum, and tumor samples are used to identify PD markers associated with treatment. Additional biomarkers related to mechanism of action, safety biomarkers, and associations with response to HuMax-IL8 in combination with nivolumab are explored.

Serum-based biomarkers: HuMax-IL8 binds to and neutralizes circulating IL-8 and causes significant decreases in serum IL-8 levels in vivo. Therefore, quantitation of serum IL-8 may be used not only for participant selection purposes but also on-treatment as a PD marker to ascertain binding to and neutralization of circulating IL-8 by HuMax-IL8. In addition, on-treatment serum samples may be used to quantify changes in inflammatory cytokines/chemokines in order to ascertain impact of treatment on participants' immune response and to assess cytotoxic T-cell responses. Whole blood may be used to assess the impact of treatment on absolute numbers of MDSCs and activation state of circulating T-cells using validated flow cytometry-based assays.

Tumor-based biomarkers: Tumor-based biomarkers to be explored for PD purposes may include, but not be limited to, expression of CD15 by IHC to ascertain impact of treatment on intra-tumoral neutrophils and polymorphonuclear-MDSC populations. In addition, tumor may be used to assess impact of treatment on general immune response within tumors. Biomarkers to address this may include, but not be limited to, changes in CD8, PD-1, PD-(L)1 and FoxP3 cell populations on-treatment (all via IHC). Gene expression profiling and T-cell receptor sequencing in tumor tissue may also be used to assess impact of treatment on immune cell activation. IL-8 can induce and maintain the EMT phenotype in cancer cells and can stimulate growth of endothelial cells, thus facilitating angiogenesis. Therefore, the impact of treatment on EMT and endothelial cells in tumor samples is evaluated. Biomarkers to assess this may include, but not be limited to, changes in expression of E-cadherin, vimentin, and CD31 (markers of epithelial, mesenchymal, and endothelial cells, respectively) via IHC.

Predictive biomarkers: In addition to serum levels of IL-8, molecular-based biomarkers including, but not limited to, tumor mutational burden and gene expression profiling in tumor samples obtained at screening may be explored retrospectively to assess association with participant response. Retrospective analysis of the expression of immune cell markers in tumor samples obtained at screening may also be performed to assess association with response to treatment. These markers may include, but not be limited to, CD15, CD8, PD-1, PD-(L)1 and FoxP3.

Efficacy Assessments: Efficacy assessments for the anti-tumor activity of HuMax-IL8 in combination with nivolumab are based on tumor measurements, using RECIST v1.1, with computed tomography and/or magnetic resonance imaging, as appropriate, at baseline and every 8 weeks (±1 week).

Example 2. Association Between Serum IL-8 and Response to Immuno-Oncology Therapy To explore the relationship between baseline IL-8 and clinical efficacy endpoints, including overall response rate (ORR), overall survival (OS), and progression free survival (PFS), exploratory analyses were conducted using data from four clinical trials, including:
(1) Study CA209-067, which is a phase 3, randomized, double-blind study of nivolumab monotherapy (NIVO) or nivolumab combined with ipilimumab (NIVO+IPI) versus ipilimumab monotherapy (IPI) in adult subjects with previous untreated, unresectable or metastatic melanoma. See Larkin et al., New England Journal of Medicine. 2015 Jul. 2; 373(1):23-34. About 900 subjects were randomized in a 1:1:1 ratio into three treatment arms, i.e., ipilimumab monotherapy, nivolumab monotherapy, and nivolumab in combination with ipilimumab.

(2) Study CA209-025, which is a randomized, open-label, phase 3 study that compared nivolumab with everolimus in patients with renal-cell carcinoma who had received previous treatment. See Motzer et al., New England Journal of Medicine. 2015 Nov. 5; 373(19): 1803-13. A total of 821 patients with advanced clear-cell renal-cell carcinoma for which they had received previous treatment with one or two regimens of anti-angiogenic therapy were randomly assigned (in a 1:1 ratio) to receive 3 mg of nivolumab per kilogram of body weight intravenously every 2 weeks or a 10-mg everolimus tablet orally once daily.

(3) Study CA209-017, which is a randomized, open-label, international, phase 3 study that evaluated the efficacy and safety of nivolumab, as compared with docetaxel in patients with the squamous subtype of non-small cell lung cancer. See Brahmer et al., New England Journal of Medicine. 2015 Jul. 9; 373(2):123-35. Approximately 272 patients were randomized to receive nivolumab, at a dose of 3 mg per kilogram of body weight every 2 weeks, or docetaxel, at a dose of 75 mg per square meter of body-surface area every 3 weeks.

(4) Study CA209-057, which is a randomized, open-label, international phase 3 study that assigned patients with nonsquamous non-small-cell lung cancer (NSCLC) that had progressed during or after platinum-based doublet chemotherapy to receive nivolumab at a dose of 3 mg per kilogram of body weight every 2 weeks or docetaxel at a dose of 75 mg per square meter of body-surface area every 3 weeks. See Borghaei et al., New England Journal of Medicine. 2015 Oct. 22; 373(17):1627-39.

Serum IL-8 was measured by immunoassay. Kaplan-Meier curve analyses of overall survival by baseline IL-8 quartiles were performed for each study and for all nivolumab-based therapies combined across the four studies. Time-dependent receiver operating characteristic (ROC) curve analyses (Hleagerty and Saha, Biometrics. 2000; 56(2):337-44) were conducted for 12-month OS for each study and for all nivo-based therapies combined across the four studies. ROC curves were used to determine IL-8 cutoffs associated with response. Additional tumor and peripheral correlative markers were assessed.

For CA209-067, in addition to the Kaplan-Meier curves and ROC curves mentioned above, the following analyses were performed:

(a) Scatter plots of baseline tumor burden (measured by baseline sum of the diameters of target lesions) and baseline IL-8.

(b) ROC curve analyses for ORR.

(c) Time-dependent ROC curve analyses for PFS (6 month) in addition to OS (12 month).

(d) Cox proportional hazard model of OS adjusting for baseline tumor, baseline IL-8, and other baseline covariates (including baseline PD-L1 status). For regression analyses, whenever appropriate, baseline IL-8 values and tumor burden were log-transformed.

Furthermore, for CA209-067, in addition to baseline IL-8 information, the association between post-baseline IL-8, change (in log-scale) from baseline in IL-8, and anti-tumor activities were also investigated using ROC curves and K-M curves.

Figure 6:
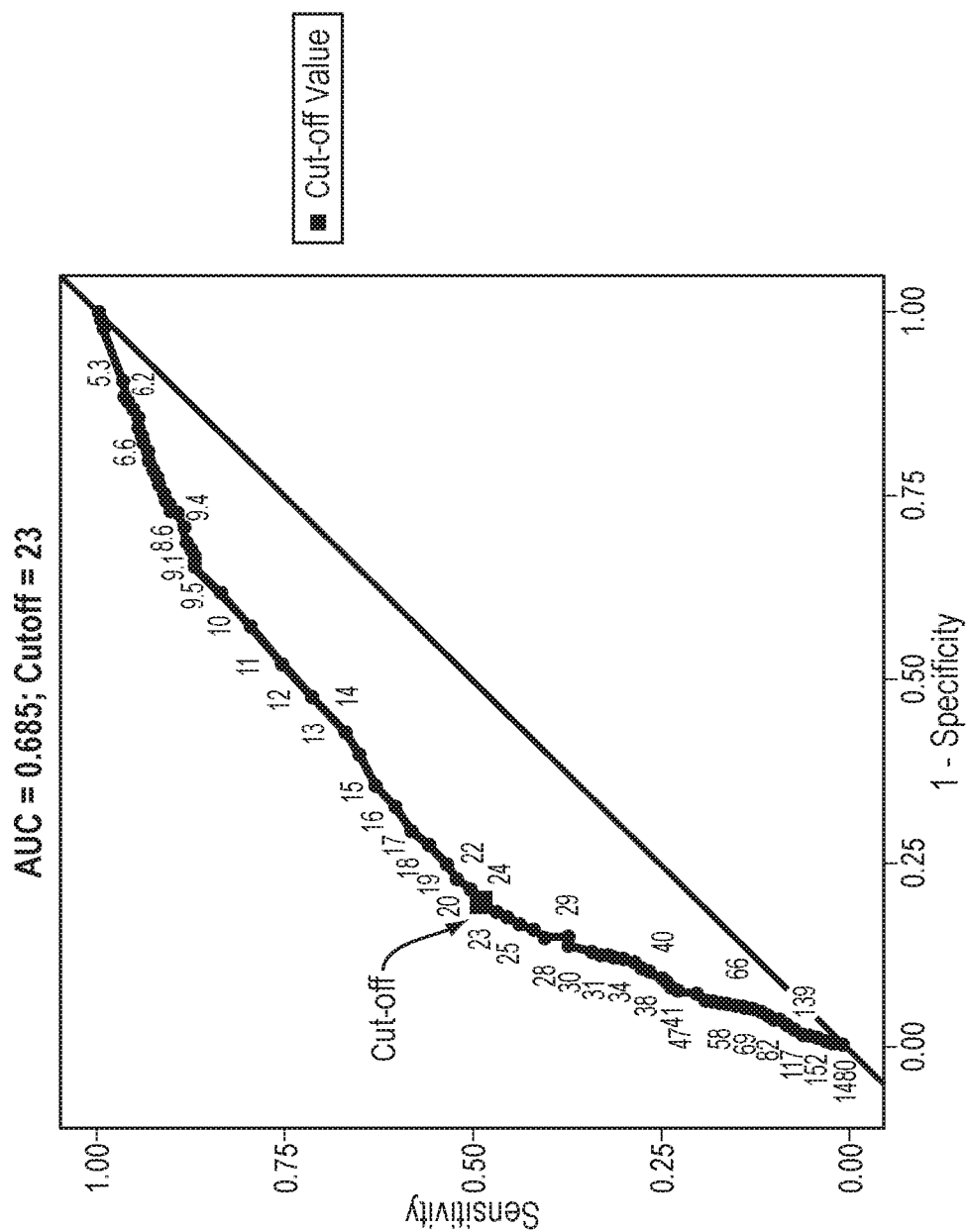
FIG. 6 is a time-dependent receiver operating characteristic (ROC) curve analysis of 12-month OS for all nivo-based therapies combined across the four studies. A cut-off value (optimal value) of 23 pg/mL of baseline IL-8 was obtained by maximizing the Youden's index, i.e., sensitivity+specificity−1.

Quartile stratification of serum IL-8 levels showed that elevated baseline IL-8 was associated with poor OS (FIGS. 1-5; Q1 being the lowest quartile by serum IL-8 baseline level). ROC analysis of nivolumab-based therapy from pooled study data identified 23 pg/mL as an IL-8 threshold that could be used to enrich for patients who may be more likely to benefit from immuno-oncology therapy (FIG. 6). Detailed analyses in patients with melanoma showed the correlation of baseline IL-8 with OS was independent of baseline tumor burden or PD-L1 tumor expression. Absolute baseline and post-baseline IL-8 levels were more strongly associated with OS, PFS, and ORR than changes from baseline.

Association of serum IL-8 with response to nivolumab-based therapy suggests that IL-8 may serve as a clinically useful biomarker to select for patients who can benefit from immuno-oncology therapy; IL-8 neutralization in patients with elevated baseline IL-8 may restore sensitivity to anti-PD-1 therapy.

Example 3. Serum IL-8 May Serve as a Biomarker of Response to Immuno-Oncology Therapy A pan-tumor, multi-trial, retrospective association analysis of serum IL-8 levels with clinical efficacy and biomarkers in patients who received nivolumab (NIVO)-based therapy was performed as follows.

Peripheral blood and tumor samples from 2,140 patients across 9 trials and multiple tumor types were analyzed (Table 4). Serum IL-8 levels were measured at baseline and on treatment using the human multianalyte profile (MAP) immunoassay platform (Myriad RBM). Change in serum IL-8 from baseline to post-baseline measurement was calculated. Verification was performed to ensure that all values relating to serum IL-8 (baseline, week 7, change from baseline, log values, quartile grouping) were derived correctly and analyses were reproducible. Baseline serum IL-8 values were pooled from multiple trials and stratified into tertile (unvalidated data) or quartile (validated data) ranges.

TABLE 4

| Nivolumab trial | Trial description | Description of analyses |
|---|---|---|
| Melanoma, N = 800 | | |
| CheckMate-038 (CA209-038) | Phase 1, PD/biomarker study of NIVO ± IPI | OS and correlative blood and tumor biomarker analyses |
| CheckMate-064 (CA209-064) | Phase 2, NIVO given sequentially with IPI | OS and correlative blood and tumor biomarker analyses |
| CheckMate-067 (CA209-067) | Phase 3, 1L NIVO ± IPI vs IPI | OS and ROC analyses |
| NSCLC, N = 730 | | |
| CheckMate-063 (CA209-063) | Phase 2 3L + NIVO in squamous cell | OS analyses |

TABLE 4-continued

| Nivolumab trial | Trial description | Description of analyses |
|---|---|---|
| CheckMate-017 (CA209-017) | Phase 3, 2L + NIVO vs docetaxel in squamous cell | OS, ROC, and correlative blood and tumor biomarkers analyses |
| CheckMate-057 (CA209-057) | Phase 3, 2L + NIVO vs docetaxel in non-squamous cell | OS, ROC, and correlative blood and tumor biomarkers analyses |
| RCC, N = 610 | | |
| CheckMate-016 (CA209-016) | Phase 1 NIVO + sunitinib or pazopanib or IPI | OS analyses |
| CheckMate-025 (CA209-025) | Phase 3, 2L to 4L NIVO vs everolimus | OS, ROC, and correlative blood and tumor biomarkers analyses |
| CheckMate-009 (CA209-009) | Phase 1, PD/biomarker study of 2L to 4L NIVO | OS and correlative blood and tumor biomarkers analyses |

1L = first line;
2L = second line;
3L = third line;
4L = fourth line;
IPI = ipilitnumab;
OS = overall survival;
PD = pharmacodynamics;
RCC = renal cell carcinoma;
ROC = receiver operating characteristic ROC analyses: The Youden Index (sensitivity+specificity−1) was used to determine the serum IL-8 threshold level for segmenting responders from nonresponders to NIVO-based therapy based on 12-month OS.

Modeling analysis of IL-8/OS correlation accounting for tumor burden and tumor PD-L1 expression: Cox proportional hazard models for OS were developed for individual studies as well as pooled data from patients treated with NIVO-based therapy, with baseline IL-8 levels, baseline tumor burden, and baseline tumor PD-L1 expression adjusted.

Gene expression analyses: Gene expression data (HTG EdgeSeq [HTG Molecular Diagnostics, Inc] or RNA sequencing) were generated from archival biopsies or biopsies obtained at screening prior to baseline serum sample acquisition. Patient data were dichotomized on the basis of optimal IL-8 threshold.

Statistical analyses: Kaplan-Meier analyses were performed on data in FIGS. 7-9. Pearson correlation coefficients were calculated for FIG. 12 between baseline serum IL-8 levels and other baseline biomarker measurements as indicated. Signature scores were calculated based on a list of genes using the median z scores of the normalized values of all genes for each sample. P values in FIG. 13 were calculated by treating IL-8 as a dichotomized variable using Welch t test; P values <0.05 were considered significant.

Figure 7:
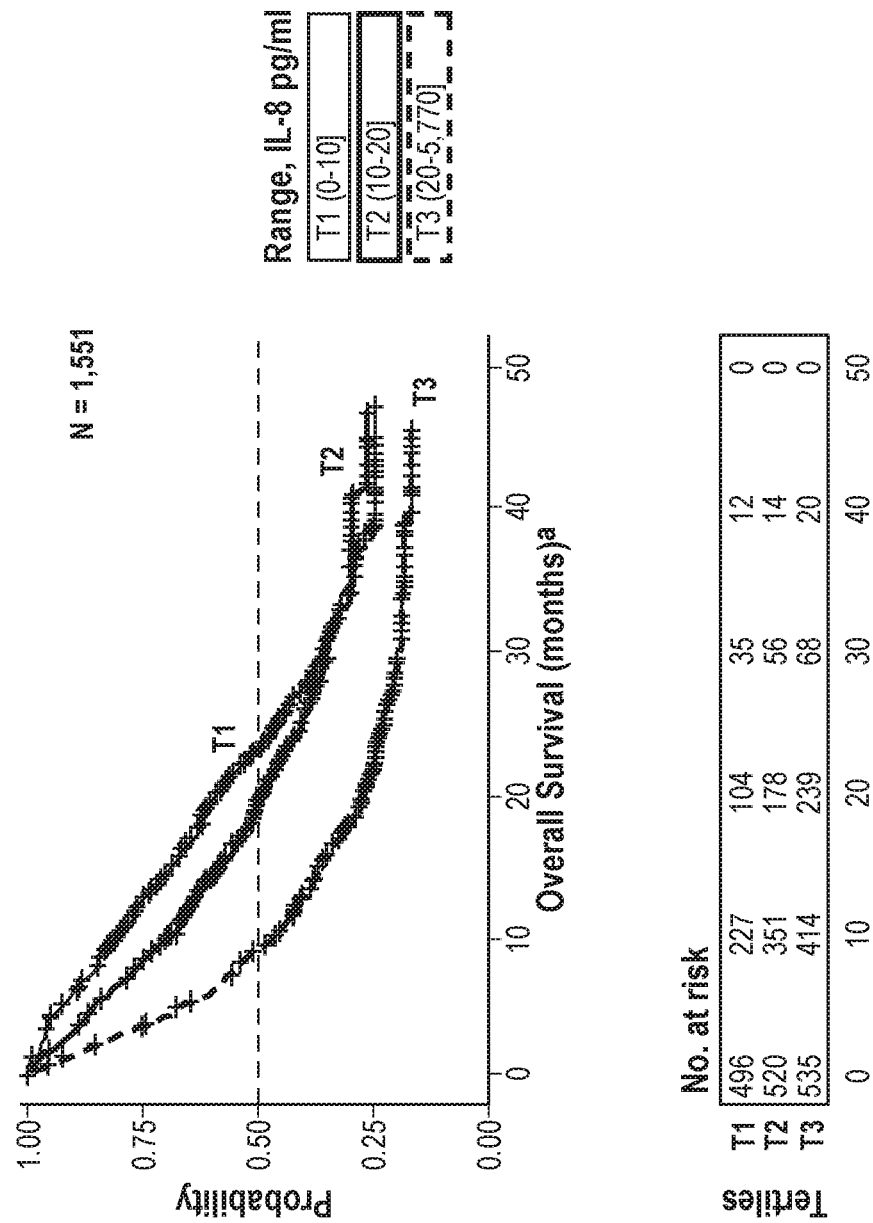
FIG. 7 is a KM-Plot of overall survival (OS) by IL-8 baseline tertile for all patients treated with nivolumab-containing therapy in CheckMate trials −038, −064, −063, −017, −057, −016, −025, and −009. Preliminary pan-tumor analysis showed that patients with elevated serum IL-8 at baseline have worse outcomes.
Figure 8:
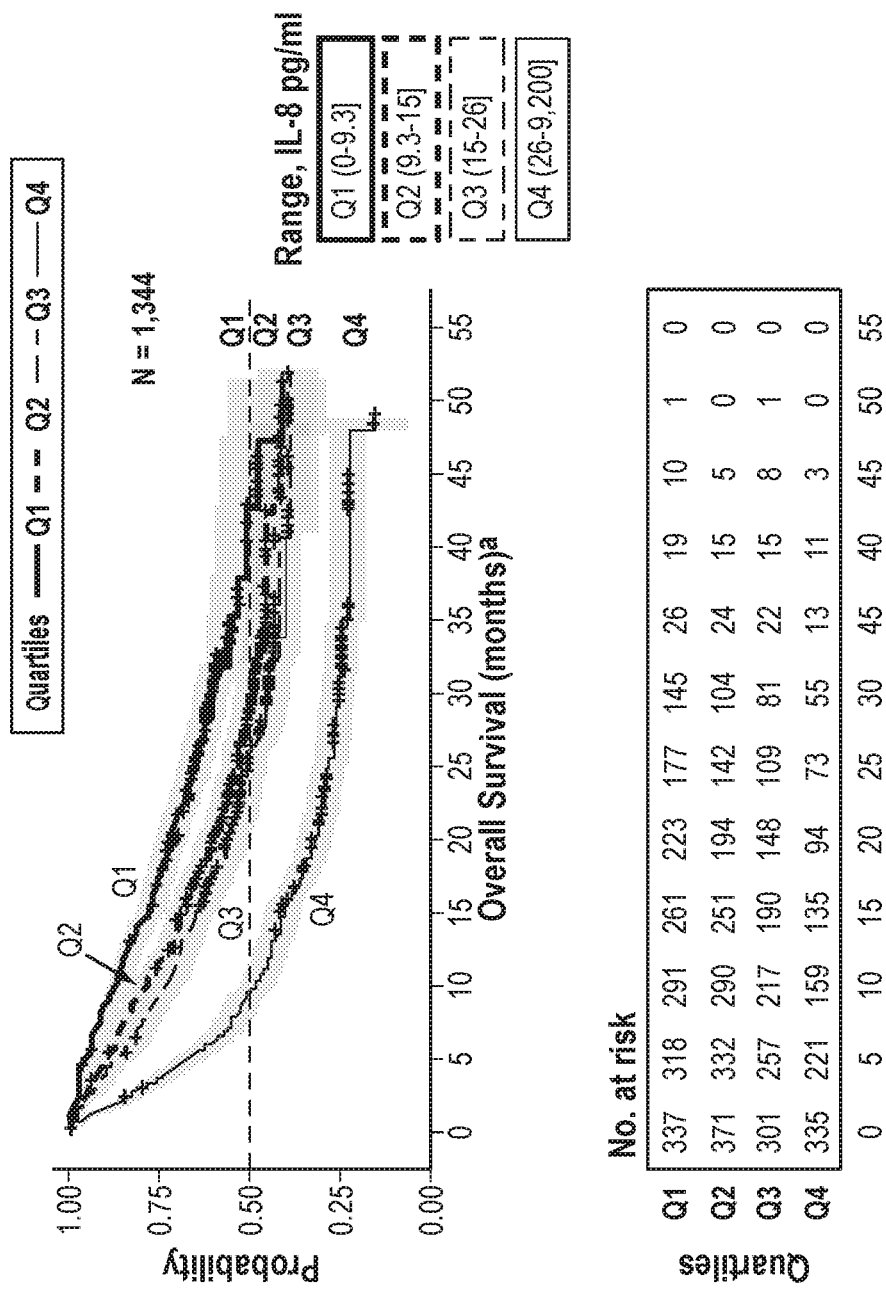
FIG. 8 is a KM-Plot of overall survival (OS) by IL-8 baseline quartile for all patients treated with nivolumab-containing therapy in CheckMate trials −017, −057, −067, and −025. Validated pan-tumor analysis confirmed reduced survival in patients with elevated serum IL-8 levels at baseline.
Figure 9:
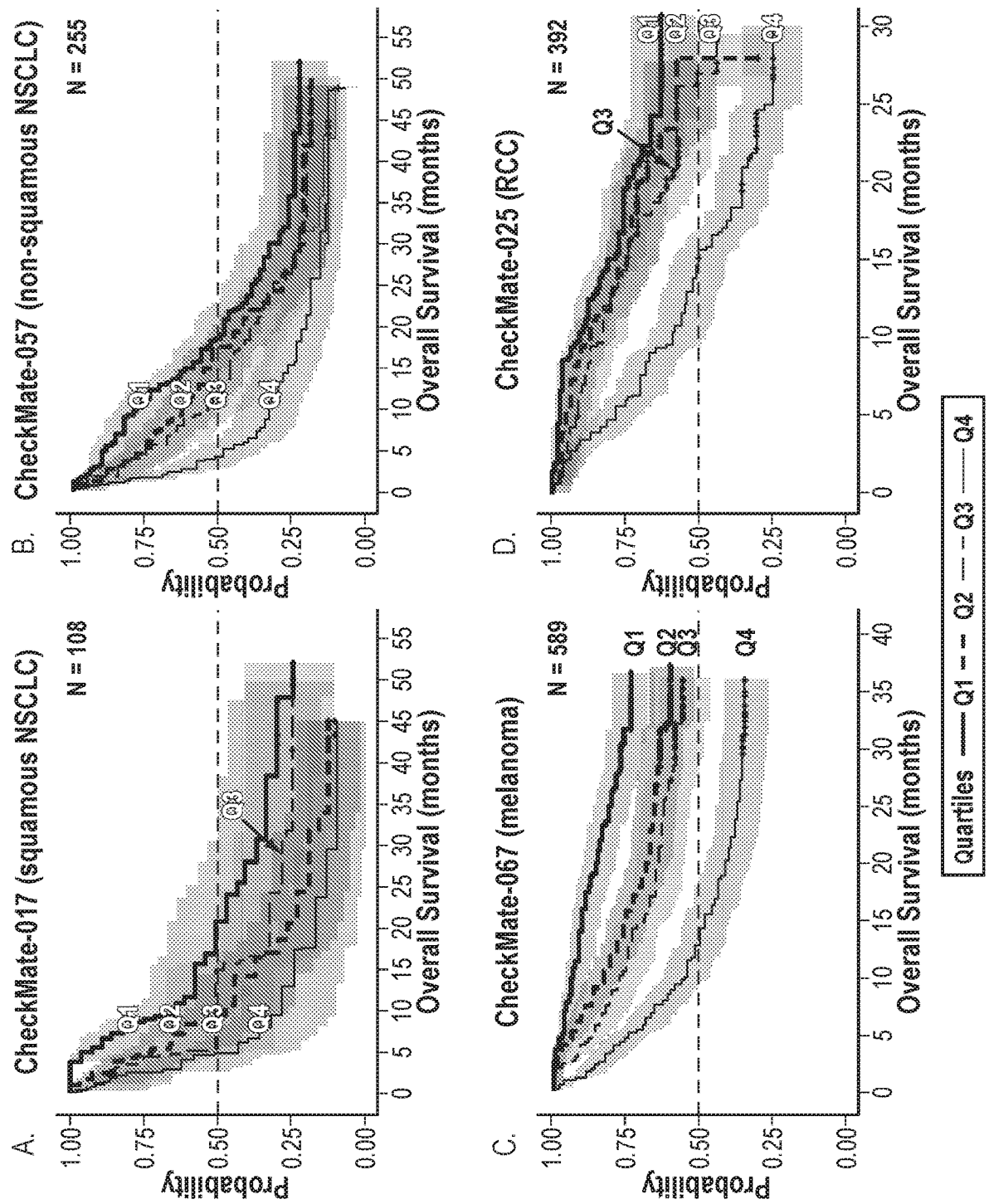
FIG. 9 shows KM-Plots of overall survival (OS) by IL-8 baseline quartile for patients treated with nivolumab-containing therapy within each phase 3 trial pooled in FIG. 8. Analysis by tumor type showed reduced survival in patients with elevated serum IL-8 levels at baseline.

Results:

Preliminary pan-tumor analysis showed that patients with elevated serum IL-8 at baseline have worse outcomes. Initial cross-trial analysis of pooled, unvalidated, baseline serum IL-8 levels from 1,551 patients indicated reduced benefit from NIVO-containing therapy in patients with higher baseline IL-8 levels (FIG. 7). Stratification of serum IL-8 into tertile ranges showed an inverse correlation between baseline serum IL-8 and OS. Validated pan-tumor analysis confirmed reduced survival in patients with elevated serum IL-8 levels at baseline. Analysis of pooled data from 1,344 patients receiving NIVO-based therapy in four phase 3 trials (CheckMate trials −017, −057, −067, −025), spanning RCC, melanoma, and squamous and non-squamous NSCLC confirmed that elevated baseline IL-8 levels were associated with decreased OS (FIG. 8). Analysis by tumor type within each NIVO phase 3 trial pooled in FIG. 8 showed reduced survival in patients with elevated serum IL-8 levels at baseline (FIG. 9). Analysis of baseline serum IL-8 level within each NIVO phase 3 trial pooled in FIG. 8 showed strong association with reduced OS, and this association of baseline serum IL-8 level with OS was independent of tumor burden and tumor PD-L1 expression; P<0.001 (FIG. 9).

Figure 10:
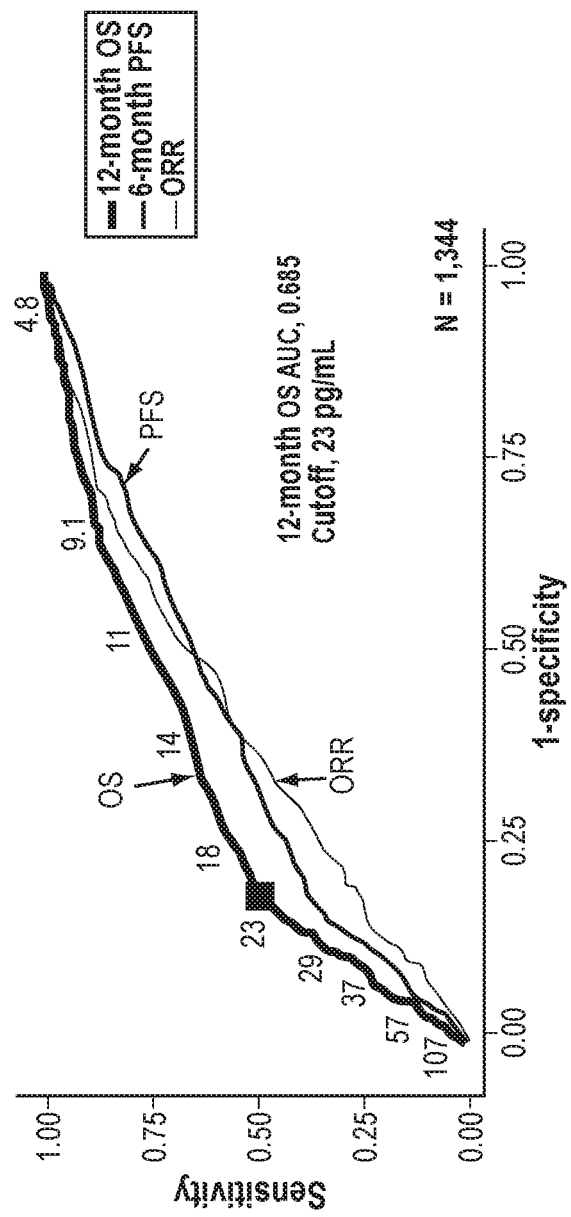
FIG. 10 shows ROC curve analyses of OS, PFS, or ORR, along with validated pooled baseline serum IL-8 data from patients treated with nivolumab-containing therapy in CheckMate trials −017, −057, −067, and −025. Sensitivity is the true-positive rate, and 1-specificity is the false-positive rate, where "positivity" is defined as OS event (within 12 months) or PFS event (within 6 months) for 12-month OS or 6-month PFS, respectively, and responder for ORR. AUC=area under curve; PFS=progression-free survival; ORR=objective response rate. Statistical analyses identifies a baseline serum IL-8 threshold below which patients were more likely to benefit from NIVO-based therapy.
Figure 11:
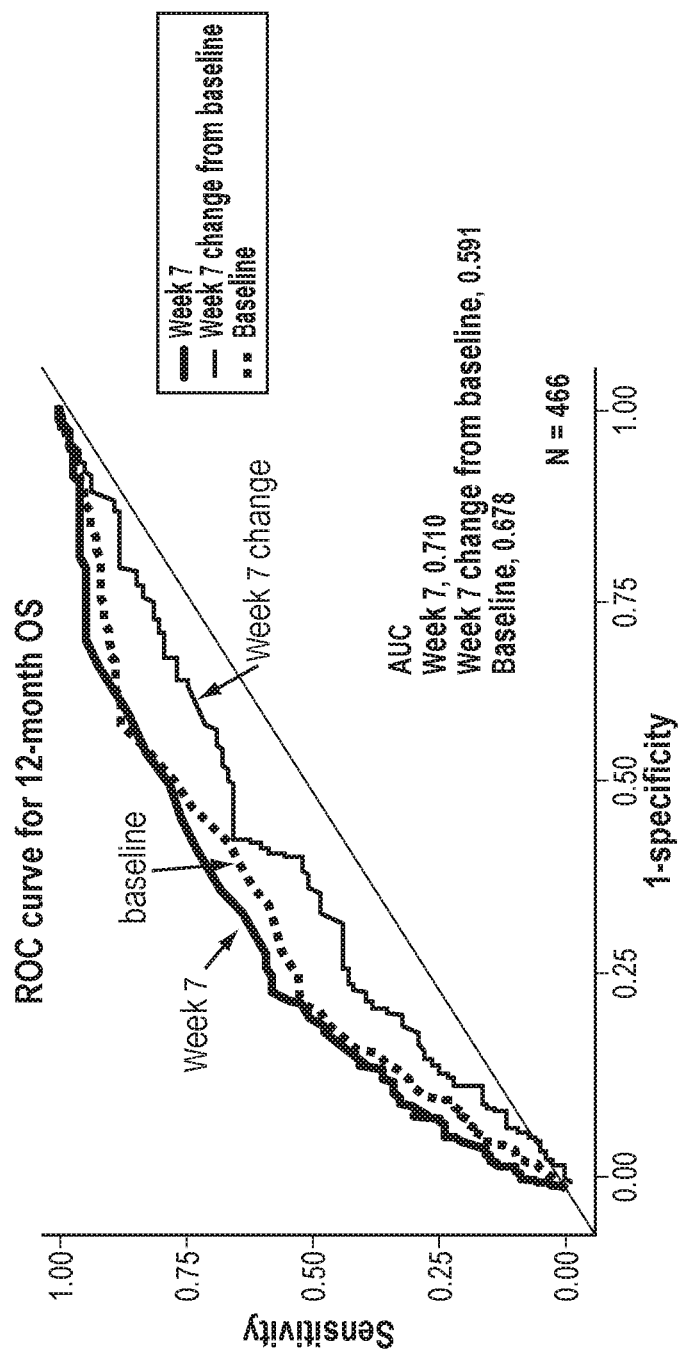
FIG. 11 shows OS ROC analysis of CheckMate-067 data to assess the relative association of OS with serum IL-8 levels at baseline, week 7, and change from baseline. IL-8 level at baseline or on-treatment at week 7 was better associated with OS than change from baseline IL-8 in patients with melanoma.

ROC curve analyses were performed using OS, PFS, or ORR, along with validated pooled baseline serum IL-8 data from four phase 3 trials (CheckMate trials −017, −057, −067, −025) (FIG. 10). OS ROC analysis identified a baseline serum IL-8 level of 23 pg/mL as a threshold to segment patients likely to respond to NIVO-based therapy (≤23 pg/mL) from those unlikely to respond (>23 pg/mL). OS ROC analysis of CheckMate-067 data was applied to assess the relative association of OS with serum IL-8 levels at baseline, week 7, and change from baseline (FIG. 11). IL-8 level at baseline or on-treatment at week 7 were better associated with OS than change from baseline IL-8 in patients with melanoma.

Figure 12:
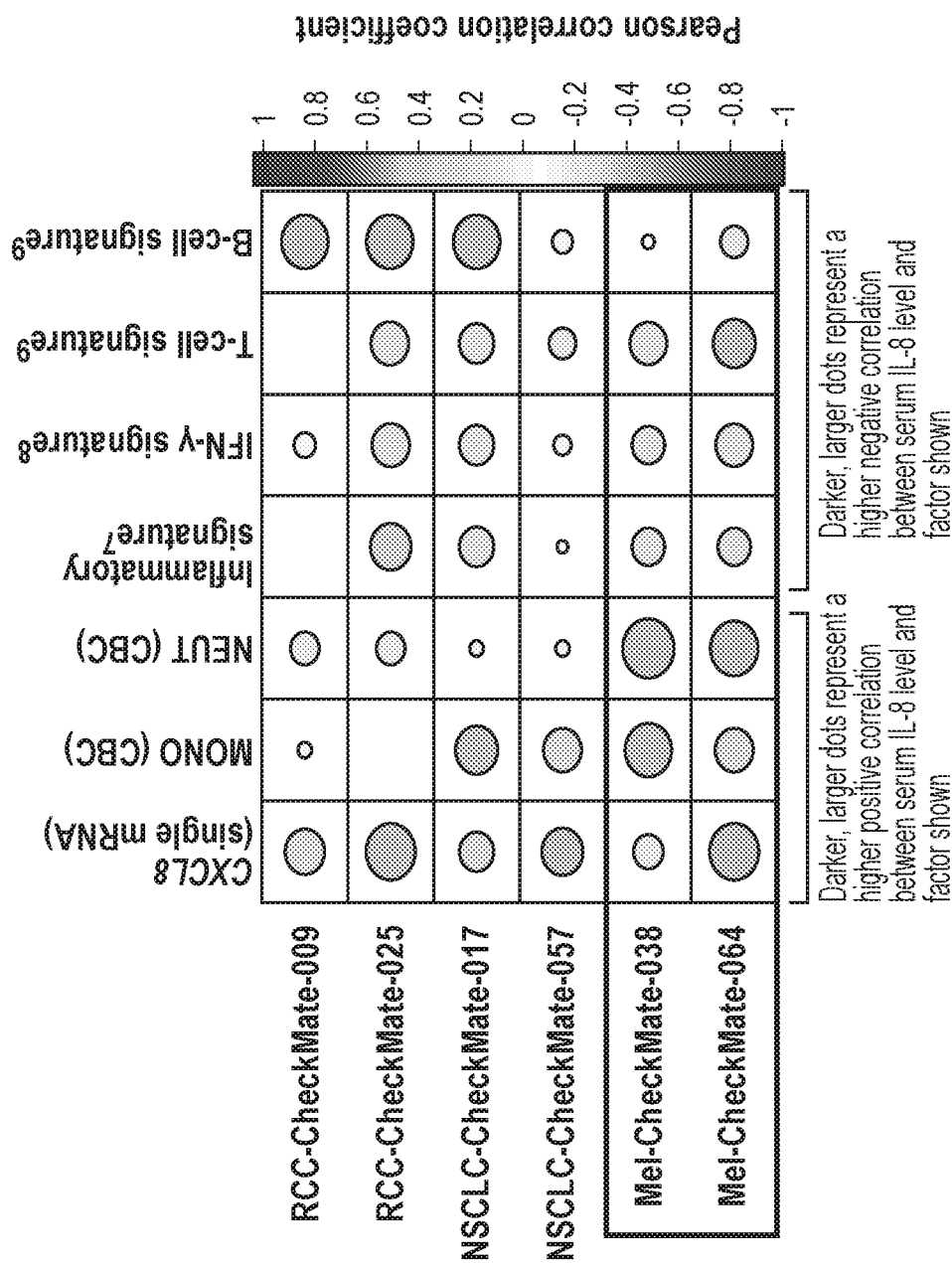
FIG. 12 shows correlation of tumoral gene expression and circulating blood biomarkers with baseline serum IL-8 levels in patients with melanoma across six trials. In columns 1-3, darker, larger dots represent a higher positive correlation between serum IL-8 level and factor shown. In columns 4-7, darker, larger dots represent a higher negative correlation between serum IL-8 level and factor shown. A positive correlation was observed between tumoral CXCL8 mRNA and serum IL-8 level across tumor types. CBC=complete blood count; IFN-γ=interferon gamma; mel=melanoma; MONO=monocyte; NEUT=neutrophil.
Figure 13A:
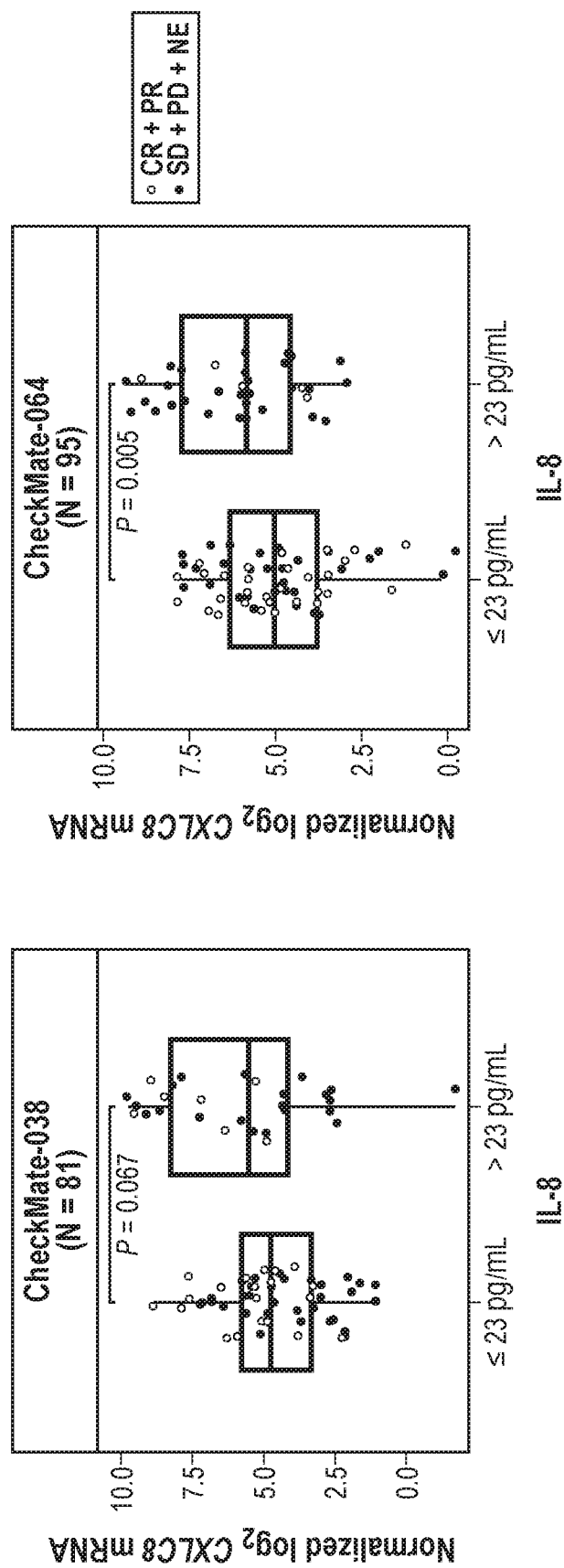
FIGS. 13A and 13B show correlative analyses in patients with melanoma using baseline serum IL-8 data dichotomized by IL-8 level (≤23 pg/mL or >23 pg/mL). 13A: Correlation between tumoral CXCL8 mRNA and baseline serum IL-8 level. 13B: Correlation between T-cell and IFN-γ inflammatory gene signatures, respectively, and baseline serum IL-8 level. CR=complete response; NE=not evaluable; PD=progressive disease; PR=partial response; SD=stable disease.
Figure 13B:
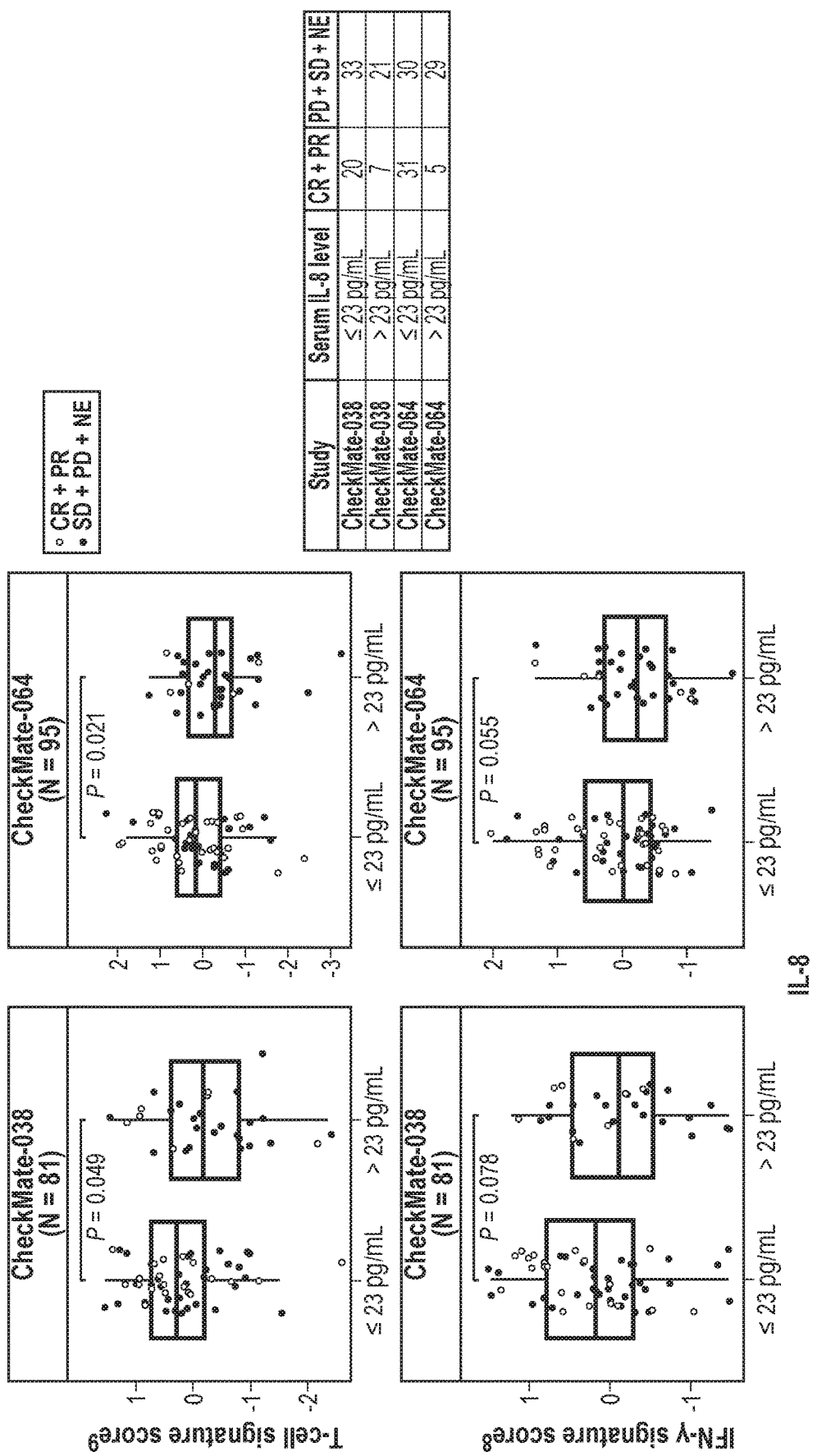

Peripheral immune cell subsets and established immune gene signatures were compared with baseline serum IL-8 levels in patients with advanced cancer across 6 NIVO trials (FIG. 12). A positive correlation was observed between tumoral CXCL8 mRNA and serum IL-8 level across tumor types. Correlative analyses in patients with melanoma were performed using baseline serum IL-8 data dichotomized by IL-8 level (≤23 pg/mL or >23 pg/mL). A positive correlation between tumoral CXCL8 mRNA and baseline serum IL-8 level was observed (FIG. 13, panel A). Serum IL-8 levels correlated negatively with T-cell and IFN-γ inflammatory gene signatures (FIG. 13, panel B.). Clinical response to NIVO-based therapy was enriched in patients with baseline serum IL-8≤23 pg/mL (FIG. 13).

This study showed that baseline serum IL-8 may serve as a surrogate marker for an immunosuppressive tumor microenvironment and a combination of anti-IL8 antibody and anti-PD-1 antibody may be efficacious in cancer patients with elevated baseline IL-8.

TABLE 5

Summary of sequences

| SEQ ID | Description | Sequence |
|---|---|---|
| 1 | HuMax-IL-8 VHCDR1 | HYGMY |
| 2 | HuMax-IL-8 VHCDR2 | VIWYDGSYEYNADSVK |
| 3 | HuMax-IL-8 VHCDR3 | DRVGLFDY |
| 4 | HuMax-IL-8 VLCDR1 | RASQSISSSYLA |
| 5 | HuMax-IL-8 VLCDR2 | GPSSRAT |
| 6 | HuMax-IL-8 VLCDR3 | QQYAGSLT |
| 7 | HuMax-IL-8 VH | QVQLVESGGGVVQPGRSLRLSCTASGFTFSHYG MYWVRQAPGKGLEWVAVIWYDGSYEYNADSVKG RFTISRDNSKNTLYLQMNSLRAEDTAVYYCARD RVGLFDYWGQGTLVTVSS |
| 8 | HuMax-IL-8 VL | EIVLTQSPGTLSLSPGERATLSCRASQSISSSY LAWYQQKPGQAPRLLIYGPSSRATGIPDRFSGS GSGTDFTLTISRLEPEDFAVYYCQQYAGSLTFG PGTKVDIK |
| 9 | HuMax-IL-8 HC | QVQLVESGGGVVQPGRSLRLSCTASGFTFSHYG MYWVRQAPGKGLEWVAVIWYDGSYEYNADSVKG RFTISRDNSKNTLYLQMNSLRAEDTAVYYCARD RVGLFDYWGQGTLVTVSSASTKGPSVFPLAPSS KSTSGGTAALGCLVKDYFPEPVTVSWNSGALTS GVHTFPAVLQSSGLYSLSSVVTVPSSSLGTQTY ICNVNHKPSNTKVDKRVEPKSCDKTHTCPPCPA PELLGGPSVFLFPPKPKDTLMISRTPEVTCVVV DVSHEDPEVKFNWYVDGVEVHNAKTKPREEQYN STYRVVSVLTVLHQDWLNGKEYKCKVSNKALPA PIEKTISKAKGQPREPQVYTLPPSREEMTKNQV SLTCLVKGFYPSDIAVEWESNGQPENNYKTTPP VLDSDGSFFLYSKLTVDKSRWQQGNVFSCSVMH EALHNHYTQKSLSLSPGK |
| 10 | HuMax-IL-8 LC | EIVLTQSPGTLSLSPGERATLSCRASQSISSSY LAWYQQKPGQAPRLLIYGPSSRATGIPDRFSGS GSGTDFTLTISRLEPEDFAVYYCQQYAGSLTFG PGTKVDIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 11 | Nivolumab VHCDR1 | NSGMH |
| 12 | Nivolumab VHCDR2 | VIWYDGSKRYYADSVKG |
| 13 | Nivolumab VHCDR3 | NDDY |
| 14 | Nivolumab VLCDR1 | RASQSVSSYLA |
| 15 | Nivolumab VLCDR2 | DASNRAT |
| 16 | Nivolumab VLCDR3 | QQSSNWPRT |
| 17 | Nivolumab VH | QVQLVESGGGVVQPGRSLRLDCKASGITFSNSG MHWVRQAPGKGLEWVAVIWYDGSKRYYADSVKG RFTISRDNSKNTLFLQMNSLRAEDTAVYYCATN DDYWGQGTLVTVSS |
| 18 | Nivolumab VL | EIVLTQSPATLSLSPGERATLSCRASQSVSSYL AWYQQKPGQAPRLLIYDASNRATGIPARFSGSG SGTDFTLTISSLEPEDFAVYYCQQSSNWPRTFG QGTKVEIK |
| 19 | Nivolumab HC | QVQLVESGGGVVQPGRSLRLDCKASGITFSNSG MHWVRQAPGKGLEWVAVIWYDGSKRYYADSVKG RFTISRDNSKNTLFLQMNSLRAEDTAVYYCATN DDYWGQGTLVTVSSASTKGPSVFPLAPCSRSTS ESTAALGCLVKDYFPEPVTVSWNSGALTSGVHT FPAVLQSSGLYSLSSVVTVPSSSLGTKTYTCNV DHKPSNTKVDKRVESKYGPPCPPCPAPEFLGGP SVFLFPPKPKDTLMISRTPEVTCVVVDVSQEDP EVQFNWYVDGVEVHNAKTKPREEQFNSTYRVVS VLTVLHQDWLNGKEYKCKVSNKGLPSSIEKTIS KAKGQPREPQVYTLPPSQEEMTKNQVSLTCLVK GFYPSDIAVEWESNGQPENNYKTTPPVLDSDGS FFLYSRLTVDKSRWQEGNVFSCSVMHEALHNHY TQKSLSLSLGK |
| 20 | Nivolumab LC | EIVLTQSPATLSLSPGERATLSCRASQSVSSYL AWYQQKPGQAPRLLIYDASNRATGIPARFSGSG SGTDFTLTISSLEPEDFAVYYCQQSSNWPRTFG QGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. A method of treating a solid tumor in a human subject, the method comprising administering to the subject an effective amount of each of:
   (a) an anti-IL-8 antibody comprising CDR1, CDR2, and CDR3 domains of the heavy chain variable region having the sequence set forth in SEQ ID NO: 7, and CDR1, CDR2, and CDR3 domains of the light chain variable region having the sequence set forth in SEQ ID NO: 8,
   (b) an anti-PD-1 antibody comprising CDR1, CDR2, and CDR3 domains of the heavy chain variable region having the sequence set forth in SEQ ID NO: 17, and CDR1, CDR2, and CDR3 domains of the light chain variable region having the sequence set forth in SEQ ID NO: 18, wherein the anti-IL-8 antibody is administered at a fixed dose of 2400 mg to 5000 mg.

2. The method of claim 1, wherein the anti-IL-8 antibody is administered to the subject once every (a) 2 weeks or 14 days or (b) 4 weeks or 28 days.

3. The method of claim 1, wherein the anti-IL-8 antibody is administered at a fixed dose of 3600 mg.

4. The method of claim 1, wherein the anti-PD-1 antibody is administered at a fixed dose of 240 mg, 360 mg, or 480 mg, or a dose of about 240 mg, 360 mg, or 480 mg.

5. The method of claim 1, wherein baseline serum IL-8 level in the subject is (a) >10 pg/mL, (b) between 10 pg/mL and 100 pg/mL, (c) between 10 pg/mL and 50 pg/mL, (d) between 10 pg/mL and 30 pg/mL, or (e) between 10 pg/mL and 23 pg/mL.

6. The method of claim 1, wherein the solid tumor has progressed or relapsed after anti-PD-1 or anti-PD-L1 therapy.

7. The method of claim 1, wherein, the anti-IL-8 antibody and anti-PD-1 antibody are administered at the following fixed doses:
   (a) 2400 mg to 3600 mg anti-IL-8 antibody and 240 mg, 360 mg, or 480 mg of anti-PD-1 antibody;
   (b) 3600 mg to 5000 mg anti-IL-8 antibody and 240 mg, 360 mg, or 480 mg of anti-PD-1 antibody; or
   (c) 3600 mg anti-IL-8 antibody and 480 mg of anti-PD-1 antibody.

8. The method of claim 1, wherein the anti-IL-8 antibody, or anti-IL8 antibody and anti-PD-1 antibody, are formulated for intravenous administration.

9. The method of claim 1, wherein the anti-IL-8 antibody and anti-PD-1 antibody are formulated together or formulated separately.

10. The method of claim 1, wherein the anti-IL-8 antibody and anti-PD-1 antibody are administered in two-week or four-week cycles for a total of up to 13 or 26 cycles.

11. The method of claim 1, wherein the treatment produces at least one therapeutic effect chosen from a reduction in size of a tumor, reduction in number of metastatic lesions over time, complete response, partial response, and stable disease.

12. The method of claim 1, wherein the solid tumor is associated with a cancer selected from the group consisting of: melanoma, non-small cell lung carcinoma, renal cell carcinoma, triple negative breast cancer, colorectal cancer, pancreatic ductal adenocarcinoma, prostate cancer, and hepatocellular carcinoma.

13. The method of claim 1, wherein the tumor is metastatic.

14. The method of claim 1, wherein the tumor is recurrent.

15. The method of claim 1, wherein the tumor is unresectable.

16. The method of claim 1, wherein the anti-IL-8 antibody comprises (a) heavy chain and light chain variable region CDRs comprising the amino acid sequences set forth in SEQ ID NOs: 1-3 and 4-6, respectively, (b) heavy and light chain variable region sequences set forth in SEQ ID NOs: 7 and 8, respectively, or (c) heavy and light chain sequences set forth in SEQ ID NOs: 9 and 10, respectively.

17. The method of claim 1, wherein the anti-PD-1 antibody comprises (a) heavy chain and light chain variable region CDRs comprising the amino acid sequences set forth in SEQ ID NOs: 11-13 and 14-16, respectively, (b) heavy and light chain variable region sequences set forth in SEQ ID NOs: 17 and 18, respectively, or (c) heavy and light chain sequences set forth in SEQ ID NOs: 19 and 20, respectively.

18. The method of claim 1, further comprising administering to the subject an effective amount of an anti-CTLA-4 antibody.

19. The method of claim 18, wherein the anti-CTLA-4 antibody is selected from ipilimumab and tremelimumab.

20. The method of claim 1, wherein:
   (a) the anti-IL-8 antibody comprises heavy and light chain variable region sequences set forth in SEQ ID NOs: 7 and 8, respectively; and
   (b) the anti-PD-1 antibody comprises heavy and light chain variable region sequences set forth in SEQ ID NOs: 17 and 18, respectively.

21. The method of claim 20, wherein:
(a) the anti-IL-8 antibody comprises heavy and light chain sequences set forth in SEQ ID NOs: 9 and 10, respectively; and
(b) the anti-PD-1 antibody comprises heavy and light chain sequences set forth in SEQ ID NOs: 19 and 20, respectively.

22. The method of claim 20, wherein the anti-IL-8 antibody is administered at a fixed dose of 3600 mg.

23. The method of claim 22, wherein the anti-IL-8 antibody is administered every 2 weeks or 14 days.

24. The method of claim 22, wherein the anti-PD-1 antibody is administered at a fixed dose of 240 mg, 360 mg, or 480 mg.

25. The method of claim 22, wherein the anti-PD-1 antibody is administered at a fixed dose of 480 mg.

26. The method of claim 20, further comprising administering to the subject an effective amount of an anti-CTLA-4 antibody.

27. The method of claim 24, further comprising administering to the subject an effective amount of an anti-CTLA-4 antibody.

28. The method of claim 27, wherein the anti-CTLA-4 antibody is ipilimumab.

* * * * *